United States Patent
Lee et al.

(10) Patent No.: US 11,548,939 B2
(45) Date of Patent: Jan. 10, 2023

(54) THERAPEUTIC COMBINATIONS USING IGF1R PATHWAY INHIBITORS, AND METHODS TO PREDICT ANTI-IGF1R THERAPEUTIC EFFICACY

(71) Applicant: UNIVERSITY OF PITTSBURGH-OF THE COMMONWEALTH SYSTEM OF HIGHER EDUCATION, Pittsburgh, PA (US)

(72) Inventors: Adrian Lee, Pittsburgh, PA (US); Alison Nagle, Pittsburgh, PA (US); Steffi Oesterreich, Pittsburgh, PA (US)

(73) Assignee: University Of Pittsburgh-Of The Commonwealth System Of Higher Education, Pittsburgh, PA (US)

( * ) Notice: Subject to any disclaimer, the term of this patent is extended or adjusted under 35 U.S.C. 154(b) by 788 days.

(21) Appl. No.: 16/286,021

(22) Filed: Feb. 26, 2019

(65) Prior Publication Data
US 2019/0315847 A1 Oct. 17, 2019

Related U.S. Application Data

(60) Provisional application No. 62/635,241, filed on Feb. 26, 2018.

(51) Int. Cl.
| | | |
|---|---|---|
| C07K 16/22 | (2006.01) | |
| A61K 31/437 | (2006.01) | |
| A61K 31/53 | (2006.01) | |
| A61K 31/4985 | (2006.01) | |
| A61P 35/00 | (2006.01) | |
| A61K 31/138 | (2006.01) | |
| A61K 31/7105 | (2006.01) | |
| G01N 33/50 | (2006.01) | |
| A61K 31/566 | (2006.01) | |

(52) U.S. Cl.
CPC ............ *C07K 16/22* (2013.01); *A61K 31/138* (2013.01); *A61K 31/437* (2013.01); *A61K 31/4985* (2013.01); *A61K 31/53* (2013.01); *A61K 31/566* (2013.01); *A61K 31/7105* (2013.01); *A61P 35/00* (2018.01); *G01N 33/5011* (2013.01)

(58) Field of Classification Search
CPC ...................................................... C07K 16/22
USPC ...................................................... 424/133.1
See application file for complete search history.

(56) References Cited

U.S. PATENT DOCUMENTS

2015/0291933 A1   10/2015   Mohamet et al.

OTHER PUBLICATIONS

Moody et al (J Endocrinol, 2014, 221(1): 145-155).*
Lau et al (Cancer Letters, 2012, 326: 191-198).*
De Leeuw et al (Journal of Pathology, 1997, 183: 404-411).*
Chen et al (Molecular Medicine Reports, 2013, 7: 1579-1584).*
Hou et al. (Cancer Res, 2011, 71(24): 7597-7607).*
Chakraborty et al. (Breast Res Treat, 2017, 163: 37-50).*
Adachi, Y. et al. Comparison of clinical outcomes between luminal invasive ductal carcinoma and luminal invasive lobular carcinoma. BMC Cancer 16, 1-9 (2016).
Andersen, C. L. et al. Active estrogen receptor-alpha signaling in ovarian cancer models and clinical specimens. Clin. Cancer Res. 23(14) clincanres.1501.2016 (2017). doi:10.1158/1078-0432.CCR-16-1501.
Barroso-Sousa, R. & Metzger-Filho, O. Differences between invasive lobular and invasive ductal carcinoma of the breast: results and therapeutic implications. Ther. Adv. Med. Oncol. 8, 261-266 (2016).
Baserga, R., Peruzzi, F. & Reiss, K. The IGF-1 receptor in cancer biology. Int. J. Cancer 107, 873-877 (2003).
Becker, M. a, Ibrahim, Y. H., Cui, X., Lee, A. V & Yee, D. The IGF pathway regulates ERα through a S6K1-dependent mechanism in breast cancer cells. Mol. Endocrinol. 25, 516-28 (2011).
Bertucci, F. et al. Lobular and ductal carcinomas of the breast have distinct genomic and expression profiles. Oncogene 27, 5359-5372 (2008).
Boone, D. N. & Lee, A. V. Targeting the Insulin-like Growth Factor Receptor Developing Biomarkers from Gene Expression Profiling. Crit Rev Oncog 17, 161-173 (2012).
Carboni, J. M. et al. Tumor Development by Transgenic Expression of a Constitutively Active Insulin-Like Growth Factor I Receptor. 3781-3788 (2005).
Centenera, M. M., Raj, G. V, Knudsen, K. E., Tilley, W. D. & Butler, L. M. Ex vivo culture of human prostate tissue and drug development. Nat. Rev. Urol. 10, 483-487 (2013).
Chen, Z. et al. Invasive lobular carcinoma of the breast: A special histological type compared with invasive ductal carcinoma. PLoS One 12, 1-17 (2017).
Chou, T. C. & Talalay, P. Quantitative analysis of dose-effect relationships: the combined effects of multiple drugs or enzyme inhibitors. Adv. Enzyme Regul. 22, 27-55 (1984).
Ciriello, G. et al. Comprehensive Molecular Portraits of Invasive Lobular Breast Cancer. Cell 163, 506-519 (2015).
Cox, O. T. et al. IGF-1 Receptor and Adhesion Signaling: An Important Axis in Determining Cancer Cell Phenotype and Therapy Resistance. Front. Endocrinol. (Lausanne). 6, 106 (2015).

(Continued)

*Primary Examiner* — Sean E Aeder
(74) *Attorney, Agent, or Firm* — Meunier Carlin & Curfman LLC

(57) ABSTRACT

Disclosed herein are methods of treating a subject with an estrogen receptor-positive (ER+) breast cancer comprising obtaining a sample of the breast cancer from the subject; determining a level of E-cadherin in the sample is reduced compared to a control; and administering a therapeutically effective amount of an IGF1R pathway inhibitor and an endocrine therapeutic. Also disclosed herein are methods to treat a cancer in a subject comprising administering a therapeutically effective amount of an IGF1R pathway inhibitor and an E-cadherin inhibitor. Also disclosed are methods to predict the likelihood a subject with a breast cancer will respond therapeutically to a treatment comprising administering an IGF1R pathway inhibitor, the method comprising obtaining a sample of the cancer from the subject; and determining a level of E-cadherin in the sample.

24 Claims, 40 Drawing Sheets

Specification includes a Sequence Listing.

(56) References Cited

OTHER PUBLICATIONS

Creighton, C. J. et al. Insulin-like growth factor-I activates gene transcription programs strongly associated with poor breast cancer prognosis. J. Clin. Oncol. 26, 4078-85 (2008).
Crudden, C., Girnita, A. & Girnita, L. Targeting the IGF-1R: The Tale of the Tortoise and the Hare. Front. Endocrinol. (Lausanne). 6, 64 (2015).
Curto, M., Cole, B. K., Lallemand, D., Liu, C. H. & McClatchey, A. I. Contact-dependent inhibition of EGFR signaling by Nf2/Merlin. J. Cell Biol. 177, 893-903 (2007).
Dean, J. L. et al. Therapeutic response to CDK4/6 inhibition in breast cancer defined by ex vivo analyses of human tumors. Cell Cycle 11, 2756-2761 (2012).
de-Freitas-Junior, J. C. M. et al. Insulin/IGF-I Signaling Pathways Enhances Tumor Cell Invasion through Bisecting GlcNAc N-glycans Modulation. An Interplay with E-Cadherin. PLoS One 8, e81579 (2013).
Derksen, P. W. B et al. Somatic inactivation of E-cadherin and p53 in mice leads to metastatic lobular mammary carcinoma through induction of anoikis resistance and angiogenesis. Cancer Cell 10, 437-449 (2006).
Ekyalongo, R. C. & Yee, D. Revisiting the IGF-1R as a breast cancer target, npj Precis. Oncol. 1, 14 (2017).
Erdem, C. et al. Proteomic Screening and Lasso Regression Reveal Differential Signaling in Insulin and Insulin-like Growth Factor I (IGF1) Pathways. Mol. Cell. Proteomics 15, 3045-3057 (2016).
Farabaugh, S. M., Boone, D. N. & Lee, A. V. Role of IGF1R in Breast Cancer Subtypes, Stemness, and Lineage Differentiation. Front. Endocrinol. (Lausanne). 6, 59 (2015).
Filho, O. M. et al. Relative effectiveness of letrozole compared with tamoxifen for patients with lobular carcinoma in the BIG 1-98 Trial. J. Clin. Oncol. 33, 2772-2778 (2015).
Friedl, P. & Alexander, S. Cancer invasion and the microenvironment: Plasticity and reciprocity. Cell 147, 992-1009 (2011).
Gualberto & Pollak, M. Emerging role of insulin-like growth factor receptor inhibitors in oncology: early clinical trial results and future directions. Oncogene 28, 3009-3021 (2009).
Guvakova, M. a & Surmacz, E. Overexpressed IGF-I receptors reduce estrogen growth requirements, enhance survival, and promote E-cadherin-mediated cell-cell adhesion in human breast cancer cells. Exp. Cell Res. 231, 149-62 (1997).
Hanahan, D. & Weinberg, R. A. Hallmarks of cancer: The next generation. Cell 144, 646-674 (2011).
Hawsawi, Y., El-Gendy, R., Twelves, C., Speirs, V. & Beattie, J. Insulin-like growth factor—oestradiol crosstalk and mammary gland tumourigenesis. Biochim. Biophys. Acta 1836, 345-53 (2013).
Jambal, P. et al. Estrogen switches pure mucinous breast cancer to invasive lobular carcinoma with mucinous features. Breast Cancer Res. Treat. 137, 431-448 (2013).
Kim, H.-J. et al., Constitutively active type I insulin-like growth factor receptor causes transformation and xenograft growth of immortalized mammary epithelial cells and is accompanied by an epithelial-to-mesenchymal transition mediated by NF-kappaB and snail. Mol. Cell. Biol. 27, 3165-75 (2007).

Lewis Cantley. PI 3-kinase links obesity, insulin resistance, and cancer. in (AACR-NCI-EORTC Molecular Targets and Cancer Therapeutics Meeting, 2017). Abstract.
Litzenburger, B. C. et al. BMS-536924 Reverses IGF-IR-induced Transformation of Mammary Epithelial Cells and Causes Growth Inhibition and Polarization of MCF7 Cells. Clin Cancer Res 15, 1-23 (2009).
Litzenburger, et al., High IGF-IR Activity in Triple-Negative Breast Cancer Cell Lines and Tumorgrafts Correlates with Sensitivity to Anti-IGF-IR Therapy, Clin Cancer Res; 17(8) Apr. 15, 2011, 15 pages.
Majumder, B. et al. Predicting clinical response to anticancer drugs using an ex vivo platform that captures tumour heterogeneity. Nat. Commun. 6, 6169 (2015).
Mauro, L. et al. Role of the IGF-I receptor in the regulation of cell-cell adhesion: Implications in cancer development and progression. J. Cell. Physiol. 194, 108-116 (2003).
Nakagawa, S. et al. Tumor microenvironment in invasive lobular carcinoma: possible therapeutic targets. Breast Cancer Res. Treat. 155, 65-75 (2016).
Onder, T. T. et al. Loss of E-cadherin promotes metastasis via multiple downstream transcriptional pathways. Cancer Res. 68, 3645-3654 (2008).
Pestalozzi, B. C. et al. Distinct clinical and prognostic features of infiltrating lobular carcinoma of the breast: Combined results of 15 International Breast Cancer Study Group clinical trials. J. Clin. Oncol. 26, 3006-3014 (2008).
Pollak, M. N. Insulin-like growth factors and neoplasia. Nat. Rev. Cancer 4(7), 505-18 (2004).
Qian, X., Karpova, T., Sheppard, A. M., McNally, J. & Lowy, D. R. E-cadherin-mediated adhesion inhibits ligand-dependent activation of diverse receptor tyrosine kinases. EMBO J. 23, 1739-1784 (2004).
Rakha, E. A. et al. Clinical and biological significance of E-cadherin protein expression in invasive lobular carcinoma of the breast. Am J Surg Pathol 34, 1472-1479 (2010).
Robertson, D. M., Zhu, M. & Wu, Y.-C. Cellular distribution of the IGF-1R in corneal epithelial cells. Exp. Eye Res. 94, 179-86 (2012).
Roxanis, I. Occurrence and significance of epithelial-mesenchymal transition in breast cancer. J. Clin. Pathol. 66, 517-21 (2013).
Sachdev, D., Hartell, J. S., Lee, A. V, Zhang, X. & Yee, D. A Dominant Negative Type I Insulin-like Growth Factor Receptor Inhibits Metastasis of Human Cancer Cells. J. Biol. Chem. 279, 5017-5024 (2004).
Shah, V. et al. PIK3CA mutations are common in lobular carcinoma in situ, but are not a biomarker of progression. Breast Cancer Res. 19, 7 (2017).
Sikora, M. J. et al. Invasive lobular carcinoma cell lines are characterized by unique estrogen-mediated gene expression patterns and altered tamoxifen response. Cancer Res. 74, 1463-1474 (2014).
Singh, P., Alex, J. M. & Bast, F. Insulin receptor (IR) and insulin-like growth factor receptor 1 (IGF-1R) signaling systems: novel treatment strategies for cancer. Med. Oncol. 31, 805 (2014).
Wang, L. et al. PI3K pathway activation results in low efficacy of both trastuzumab and lapatinib. BMC Cancer 11, 11:248 (2011).
Yee, D. & Lee, A. V. Crosstalk between the insulin-like growth factors and estrogens in breast cancer. J. Mammary Gland Biol. Neoplasia 5, 107-15 (2000).

* cited by examiner

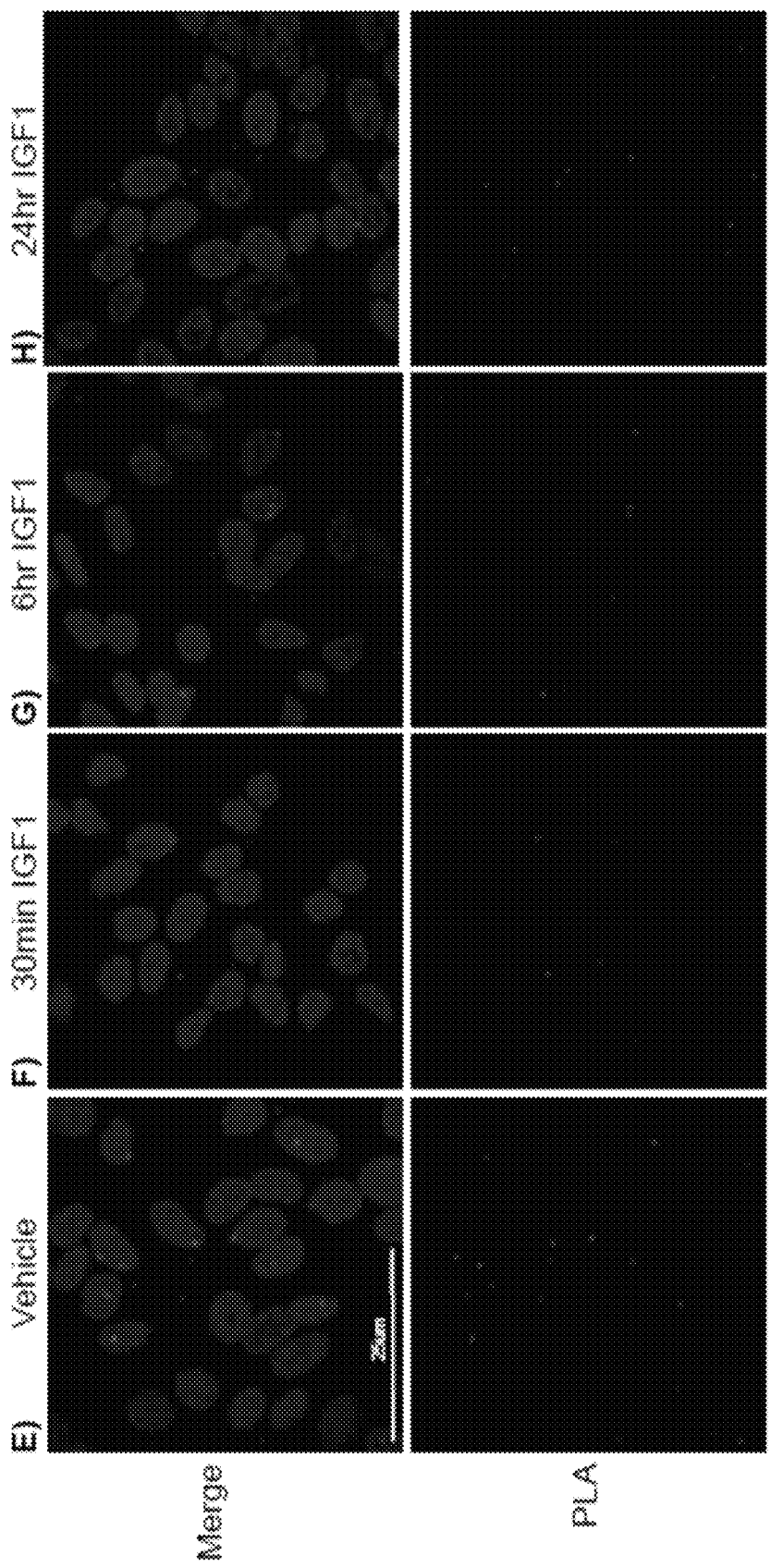

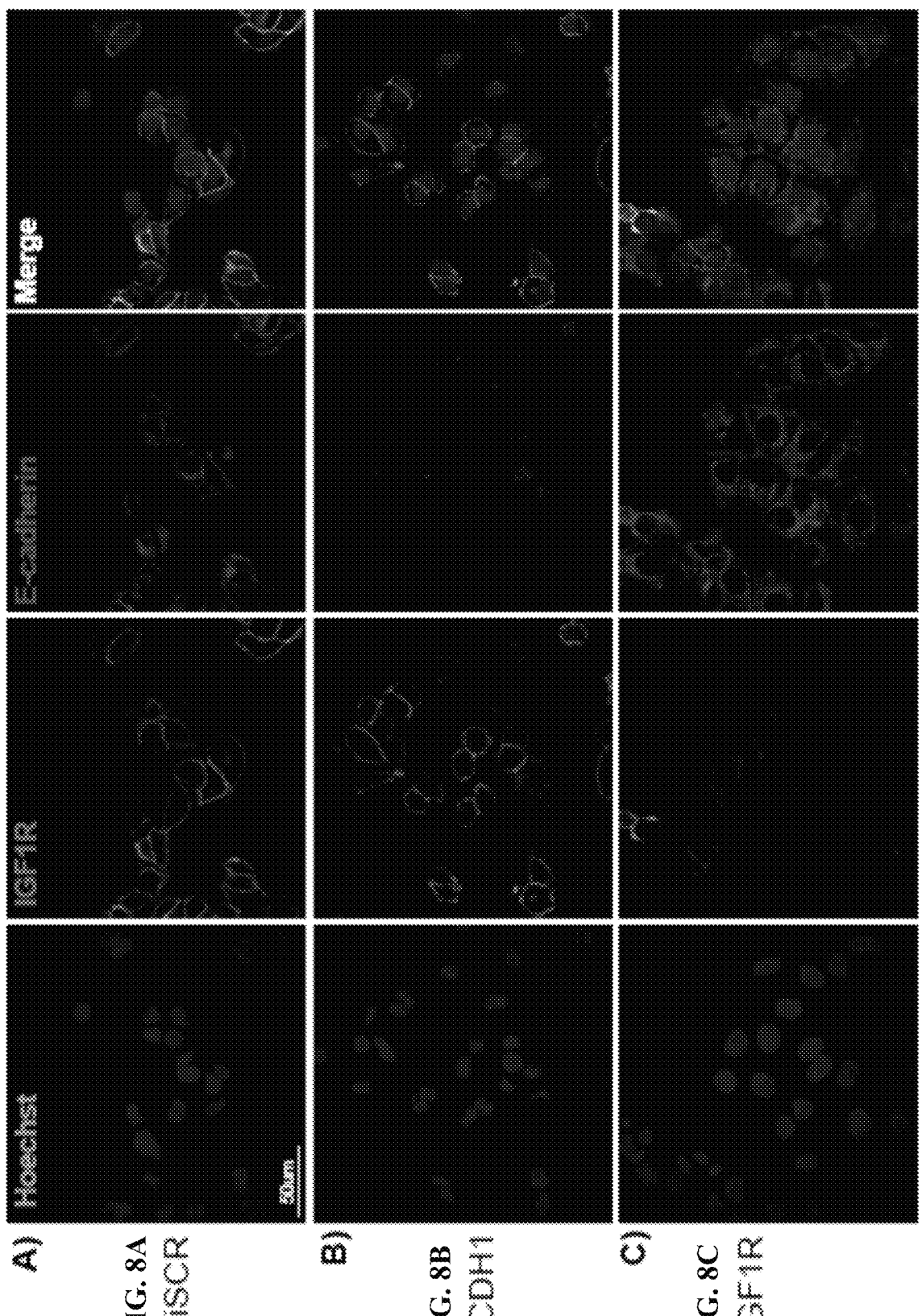
FIG. 8A siSCR
FIG. 8B siCDH1
FIG. 8C siIGF1R

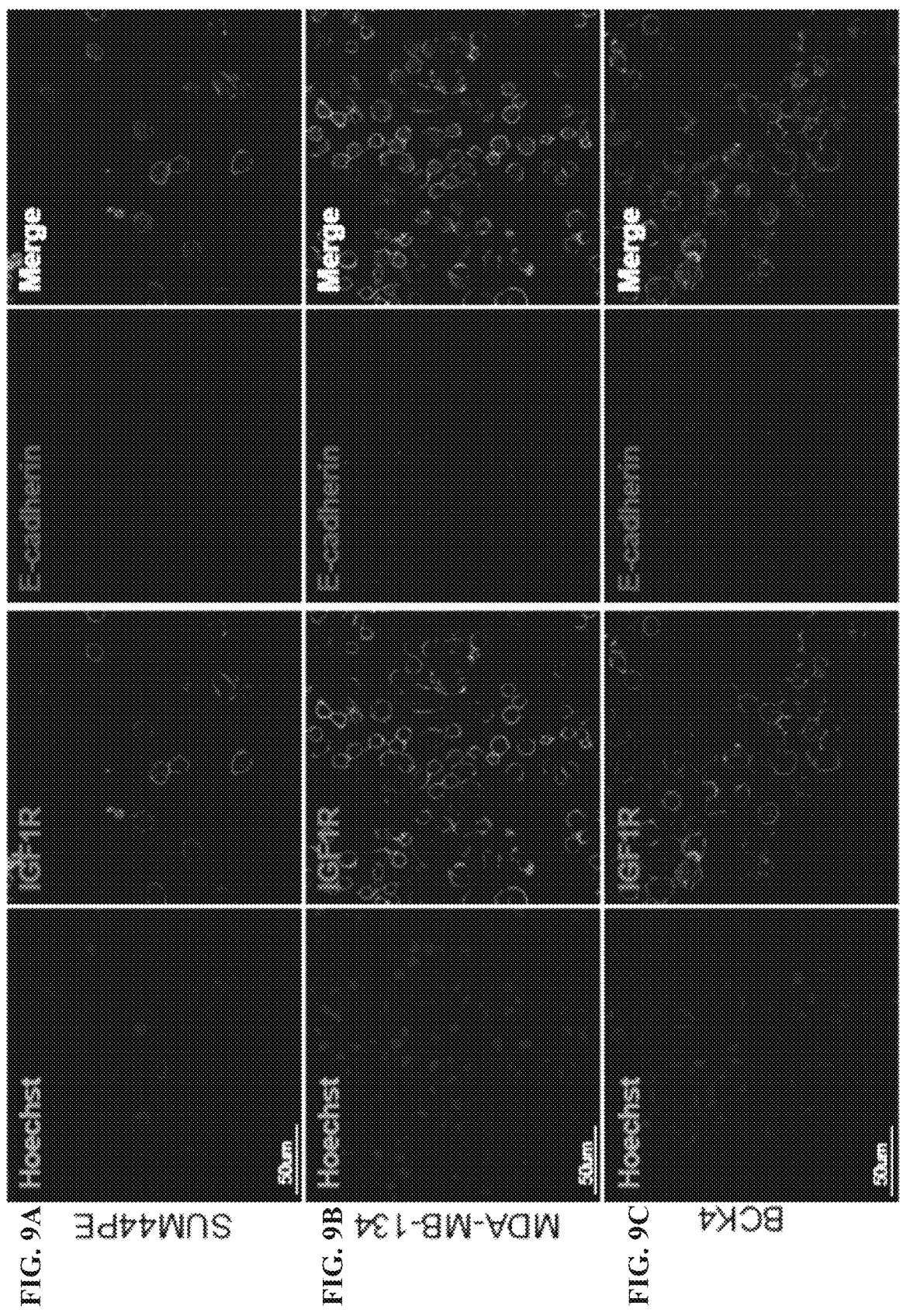

SEQUENCE LISTING

```
<160> NUMBER OF SEQ ID NOS: 6

<210> SEQ ID NO 1
<211> LENGTH: 882
<212> TYPE: PRT
<213> ORGANISM: Homo sapiens

<400> SEQUENCE: 1

Met Gly Pro Trp Ser Arg Ser Leu Ser Ala Leu Leu Leu Leu Leu Gln
1               5                   10                  15
```

```
Val Ser Ser Trp Leu Cys Gln Glu Pro Glu Pro Cys His Pro Gly Phe
             20                  25                  30

Asp Ala Glu Ser Tyr Thr Phe Thr Val Pro Arg Arg His Leu Glu Arg
             35                  40                  45

Gly Arg Val Leu Gly Arg Val Asn Phe Glu Asp Cys Thr Gly Arg Gln
 50                  55                  60

Arg Thr Ala Tyr Phe Ser Leu Asp Thr Arg Phe Lys Val Gly Thr Asp
 65                  70                  75                  80

Gly Val Ile Thr Val Lys Arg Pro Leu Arg Phe His Asn Pro Gln Ile
             85                  90                  95

His Phe Leu Val Tyr Ala Trp Asp Ser Thr Tyr Arg Lys Phe Ser Thr
             100                 105                 110

Lys Val Thr Leu Asn Thr Val Gly His His Arg Pro Pro His
             115                 120                 125

Gln Ala Ser Val Ser Gly Ile Gln Ala Glu Leu Leu Thr Phe Pro Asn
 130                 135                 140

Ser Ser Pro Gly Leu Arg Arg Gln Lys Arg Asp Trp Val Ile Pro Pro
145                 150                 155                 160

Ile Ser Cys Pro Glu Asn Glu Lys Gly Pro Phe Pro Lys Asn Leu Val
             165                 170                 175

Gln Ile Lys Ser Asn Lys Asp Lys Glu Gly Lys Val Phe Tyr Ser Ile
             180                 185                 190

Thr Gly Gln Gly Ala Asp Thr Pro Pro Val Gly Val Phe Ile Ile Glu
             195                 200                 205

Arg Glu Thr Gly Trp Leu Lys Val Thr Glu Pro Leu Asp Arg Glu Arg
             210                 215                 220

Ile Ala Thr Tyr Thr Leu Phe Ser His Ala Val Ser Ser Asn Gly Asn
225                 230                 235                 240

Ala Val Glu Asp Pro Met Glu Ile Leu Ile Thr Val Thr Asp Gln Asn
             245                 250                 255

Asp Asn Lys Pro Glu Phe Thr Gln Glu Val Phe Lys Gly Ser Val Met
             260                 265                 270

Glu Gly Ala Leu Pro Gly Thr Ser Val Met Glu Val Thr Ala Thr Asp
             275                 280                 285

Ala Asp Asp Asp Val Asn Thr Tyr Asn Ala Ala Ile Ala Tyr Thr Ile
             290                 295                 300

Leu Ser Gln Asp Pro Glu Leu Pro Asp Lys Asn Met Phe Thr Ile Asn
305                 310                 315                 320

Arg Asn Thr Gly Val Ile Ser Val Val Thr Thr Gly Leu Asp Arg Glu
             325                 330                 335

Ser Phe Pro Thr Tyr Thr Leu Val Val Gln Ala Ala Asp Leu Gln Gly
             340                 345                 350

Glu Gly Leu Ser Thr Thr Ala Thr Ala Val Ile Thr Val Thr Asp Thr
             355                 360                 365

Asn Asp Asn Pro Pro Ile Phe Asn Pro Thr Thr Tyr Lys Gly Gln Val
             370                 375                 380

Pro Glu Asn Glu Ala Asn Val Val Ile Thr Thr Leu Lys Val Thr Asp
385                 390                 395                 400

Ala Asp Ala Pro Asn Thr Pro Ala Trp Glu Ala Val Tyr Thr Ile Leu
             405                 410                 415

Asn Asp Asp Gly Gly Gln Phe Val Val Thr Thr Asn Pro Val Asn Asn
             420                 425                 430
```

```
Asp Gly Ile Leu Lys Thr Ala Lys Gly Leu Asp Phe Glu Ala Lys Gln
            435                 440                 445
Gln Tyr Ile Leu His Val Ala Val Thr Asn Val Val Pro Phe Glu Val
    450                 455                 460
Ser Leu Thr Thr Ser Thr Ala Thr Val Thr Val Asp Val Leu Asp Val
465                 470                 475                 480
Asn Glu Ala Pro Ile Phe Val Pro Pro Glu Lys Arg Val Glu Val Ser
                485                 490                 495
Glu Asp Phe Gly Val Gly Gln Glu Ile Thr Ser Tyr Thr Ala Gln Glu
            500                 505                 510
Pro Asp Thr Phe Met Glu Gln Lys Ile Thr Tyr Arg Ile Trp Arg Asp
    515                 520                 525
Thr Ala Asn Trp Leu Glu Ile Asn Pro Asp Thr Gly Ala Ile Ser Thr
530                 535                 540
Arg Ala Glu Leu Asp Arg Glu Asp Phe Glu His Val Lys Asn Ser Thr
545                 550                 555                 560
Tyr Thr Ala Leu Ile Ile Ala Thr Asp Asn Gly Ser Pro Val Ala Thr
                565                 570                 575
Gly Thr Gly Thr Leu Leu Leu Ile Leu Ser Asp Val Asn Asp Asn Ala
            580                 585                 590
Pro Ile Pro Glu Pro Arg Thr Ile Phe Phe Cys Glu Arg Asn Pro Lys
    595                 600                 605
Pro Gln Val Ile Asn Ile Ile Asp Ala Asp Leu Pro Pro Asn Thr Ser
    610                 615                 620
Pro Phe Thr Ala Glu Leu Thr His Gly Ala Ser Ala Asn Trp Thr Ile
625                 630                 635                 640
Gln Tyr Asn Asp Pro Thr Gln Glu Ser Ile Ile Leu Lys Pro Lys Met
                645                 650                 655
Ala Leu Glu Val Gly Asp Tyr Lys Ile Asn Leu Lys Leu Met Asp Asn
            660                 665                 670
Gln Asn Lys Asp Gln Val Thr Thr Leu Glu Val Ser Val Cys Asp Cys
    675                 680                 685
Glu Gly Ala Ala Gly Val Cys Arg Lys Ala Gln Pro Val Glu Ala Gly
    690                 695                 700
Leu Gln Ile Pro Ala Ile Leu Gly Ile Leu Gly Gly Ile Leu Ala Leu
705                 710                 715                 720
Leu Ile Leu Ile Leu Leu Leu Leu Leu Phe Leu Arg Arg Arg Ala Val
                725                 730                 735
Val Lys Glu Pro Leu Leu Pro Pro Glu Asp Asp Thr Arg Asp Asn Val
            740                 745                 750
Tyr Tyr Tyr Asp Glu Glu Gly Gly Gly Glu Glu Asp Gln Asp Phe Asp
    755                 760                 765
Leu Ser Gln Leu His Arg Gly Leu Asp Ala Arg Pro Glu Val Thr Arg
770                 775                 780
Asn Asp Val Ala Pro Thr Leu Met Ser Val Pro Arg Tyr Leu Pro Arg
785                 790                 795                 800
Pro Ala Asn Pro Asp Glu Ile Gly Asn Phe Ile Asp Glu Asn Leu Lys
                805                 810                 815
Ala Ala Asp Thr Asp Pro Thr Ala Pro Pro Tyr Asp Ser Leu Leu Val
            820                 825                 830
Phe Asp Tyr Glu Gly Ser Gly Ser Glu Ala Ala Ser Leu Ser Ser Leu
    835                 840                 845
Asn Ser Ser Glu Ser Asp Lys Asp Gln Asp Tyr Asp Tyr Leu Asn Glu
```

```
                        850               855                860
Trp Gly Asn Arg Phe Lys Lys Leu Ala Asp Met Tyr Gly Gly Gly Glu
865                 870                 875                 880

Asp Asp

<210> SEQ ID NO 2
<211> LENGTH: 2808
<212> TYPE: DNA
<213> ORGANISM: Homo sapiens

<400> SEQUENCE: 2
ggaaagcacc tgtgagcttg gcaagtcagt tcagagctcc agcccgctcc agcccggccc      60
gacccgaccg cacccggcgc ctgcctcgct cgggctcccc ggccagccat gggcccttgg     120
agccgcagcc tctcgggcct gctgctgctg ctgaggtctc ctcttggctc tcaggagcgg     180
agccctcctc cctgtttgac gcgagagcta cacgttcacg gtgccccggc gccacctgag     240
aagaggccgc gtctgggcag agtgaatttt gaagattgca ccggtcgaca aaggacagct     300
attttcctga caccgattcc gaaagtgggc acagatggtg tgattacagt caaaaggcct     360
ctacggtttc ataacccaac agatccattt cttggtctac gctgggactc cacctacaga     420 aagtttttcca ccaaagtcac gctgaataca gtggggcacc accaccgccc ccgcccat     480 caggcctccg tttctggaat ccaagcagaa ttgctcacat tcccaactc ctctcctggc     540 ctcagaagac agaagagaga ctgggttatt cctcccatca gctgcccaga aaatgaaaaa     600
ggcccatttc ctaaaaacct ggttcagatc aaatccaaca aagacaaaga aggcaaggtt     660
ttctacagca tcactggcca aggagctgac acaccccctg ttggtgtctt tattattgaa     720
agagaaacag gatggctgaa ggtgacgag cctctggata gagaacgcat tgccacatac      780
actctcttct ctcacgctgt gtcatccaac gggaatgcag ttgaggatcc aatggagatt     840
ttgatcacgg taaccgatca gaatgacaac aagcccgaat cacccagga ggtctttaag     900 gggtctgtca tggaaggtgc tcttccagga acctctgtga tggaggtcac agccacagac     960
gcggacgatg atgtgaacac ctacaatgcc gccatcgctt acaccatcct cagccaagat    1020
cctgagctcc ctgacaaaaa tatgttcacc attaacagga cacaggagt catcagtgtg    1080 gtcaccactg gctggaccg agagagtttc cctacgtata ccctggtggt tcaagctgct    1140
gaccttcaag gtgaggggtt aagcacaaca gcaacagctg tgatcacagt cactgacacc    1200
aacgataatc ctccgatctt caatcccacc acgtacaagg tcaggtgcc tgagaacgag    1260 gctaacgtcg taatcaccac actgaaagtg actgatgctg atgcccccaa taccccagcg    1320
tgggaggctg tataccacat attgaatgat gatggtggac aatttgtcgt caccacaaat    1380
ccagtgaaca cgatggcat tttgaaaaca gcaaagggct tggatttgga ggccaagcag    1440
cagtacattc tacacgtagc agtgacgaat gtggtacctt ttgaggtctc tctcaccacc    1500
tccacagcca ccgtcaccgt ggatgtgctg gatgtgaatg aaggccccat ctttgtgcct    1560
cctgaaaaga gagtggaagt gtccgaggac tttggcgtgg gccaggaaat cacatcctac    1620
actgcccagg agccagacac atttatggaa cagaaaataa catatcggat ttggagagac    1680
actcgcaact ggctggagat taatccggac actggtgcca tttccactcg ggctgagctg    1740
gacagggagg attttgagca cgtgaagaac agcacgtaca cagccctaat catagctaca    1800
gacaatggtt ctccagttgc tactggaaca gggacttc tgctgatcct gtctgatgtg    1860
aatgacaacg ccccataccc agaacctcga actatattct tctgtgagag gaatccaaag    1920
```

-continued

```
cctcaggtca taaacattca tgatgcagac cttcctccca atacatctcc cttcacagca    1980
gaactaacac acgggcgagt gcccaactgg accattcagt acaacgaccc aacccaagaa    2040
tctatcattt tgaagccaaa gatggcctta gaggtgggtg actacaaaat caatctcaag    2100
ctcatggata accagaataa agaccaagtg accaccttag aggtcagcgt gtgtgactgt    2160 gaagggggccg ccggcgtctg taggaaggca cagcctgtcg aagcaggatt gcaaattcct    2220
gccattctgg ggattcttgg aggaattctt gctttgctaa ttctgattct gctgctcttg    2280
ctgtttcttc ggaggagagc ggtggtcaaa gagcccttac tgcccccaga ggatgacacc    2340
cgggacaacg tttattacta tgatgaagaa ggaggcggag aagaggacca ggactttgac    2400
ttgagccagc tgcacagggg cctggacgct cggcctgaag tgactcgtaa cgacgttgca    2460
ccaaccctca tgagtgtccc ccggtatctt ccccgccctg ccaatcccga tgaaattgga    2520
aattttattg atgaaaatct gaaagcggct gatactgacc ccacagcccc gccttatgat    2580
tctctgctcg tgtttgacta tgaaggaagc ggttccgaag ctgctagtct gagctccctg    2640
aactcctcag agtcagacaa agaccaggac tatgactact tgaacgaatg gggcaatccg    2700
ttcaagaagc tggctgacat gtacggaggc ggcgaggacc actaggggac tcgagagagg    2760
cggcccagac catgtgcaga aatgcagaaa tcagcgttct ggtgtttt              2808
```

<210> SEQ ID NO 3
<211> LENGTH: 1367
<212> TYPE: PRT
<213> ORGANISM: Homo sapiens

<400> SEQUENCE: 3

```
Met Lys Ser Gly Ser Gly Gly Ser Pro Thr Ser Leu Trp Gly Leu
1               5                   10                  15

Leu Phe Leu Ser Ala Ala Leu Ser Leu Trp Pro Thr Ser Gly Glu Ile
            20                  25                  30

Cys Gly Pro Gly Ile Asp Ile Arg Asn Asp Tyr Gln Gln Leu Lys Arg
        35                  40                  45

Leu Glu Asn Cys Thr Val Ile Glu Gly Tyr Leu His Ile Leu Leu Ile
    50                  55                  60

Ser Lys Ala Glu Asp Tyr Arg Ser Tyr Arg Phe Pro Lys Leu Thr Val
65                  70                  75                  80

Ile Thr Glu Tyr Leu Leu Leu Phe Arg Val Ala Gly Leu Glu Ser Leu
                85                  90                  95

Gly Asp Leu Phe Pro Asn Leu Thr Val Ile Arg Gly Trp Lys Leu Phe
            100                 105                 110

Tyr Asn Tyr Ala Leu Val Ile Phe Glu Met Thr Asn Leu Lys Asp Ile
        115                 120                 125

Gly Leu Tyr Asn Leu Arg Asn Ile Thr Arg Gly Ala Ile Arg Ile Glu
    130                 135                 140

Lys Asn Ala Asp Leu Cys Tyr Leu Ser Thr Val Asp Trp Ser Leu Ile
145                 150                 155                 160

Leu Asp Ala Val Ser Asn Asn Tyr Ile Val Gly Asn Lys Pro Pro Lys
                165                 170                 175

Glu Cys Gly Asp Leu Cys Pro Gly Thr Met Glu Glu Lys Pro Met Cys
            180                 185                 190

Glu Lys Thr Thr Ile Asn Asn Glu Tyr Asn Tyr Arg Cys Trp Thr Thr
        195                 200                 205

Asn Arg Cys Gln Lys Met Cys Pro Ser Thr Cys Gly Lys Arg Ala Cys
    210                 215                 220
```

-continued

Thr Glu Asn Asn Glu Cys Cys His Pro Glu Cys Leu Gly Ser Cys Ser
225                 230                 235                 240

Ala Pro Asp Asn Asp Thr Ala Cys Val Ala Cys Arg His Tyr Tyr Tyr
            245                 250                 255

Ala Gly Val Cys Val Pro Ala Cys Pro Pro Asn Thr Tyr Arg Phe Glu
            260                 265                 270

Gly Trp Arg Cys Val Asp Arg Asp Phe Cys Ala Asn Ile Leu Ser Ala
            275                 280                 285

Glu Ser Ser Asp Ser Glu Gly Phe Val Ile His Asp Gly Glu Cys Met
            290                 295                 300

Gln Glu Cys Pro Ser Gly Phe Ile Arg Asn Gly Ser Gln Ser Met Tyr
305                 310                 315                 320

Cys Ile Pro Cys Glu Gly Pro Cys Pro Lys Val Cys Glu Glu Glu Lys
            325                 330                 335

Lys Thr Lys Thr Ile Asp Ser Val Thr Ser Ala Gln Met Leu Gln Gly
            340                 345                 350

Cys Thr Ile Phe Lys Gly Asn Leu Leu Ile Asn Ile Arg Arg Gly Asn
            355                 360                 365

Asn Ile Ala Ser Glu Leu Glu Asn Phe Met Gly Leu Ile Glu Val Val
370                 375                 380

Thr Gly Tyr Val Lys Ile Arg His Ser His Ala Leu Val Ser Leu Ser
385                 390                 395                 400

Phe Leu Lys Asn Leu Arg Leu Ile Leu Gly Glu Gln Leu Glu Gly
            405                 410                 415

Asn Tyr Ser Phe Tyr Val Leu Asp Asn Gln Asn Leu Gln Gln Leu Trp
            420                 425                 430

Asp Trp Asp His Arg Asn Leu Thr Ile Lys Ala Gly Lys Met Tyr Phe
            435                 440                 445

Ala Phe Asn Pro Lys Leu Cys Val Ser Glu Ile Tyr Arg Met Glu Glu
            450                 455                 460

Val Thr Gly Thr Lys Gly Arg Gln Ser Lys Gly Asp Ile Asn Thr Arg
465                 470                 475                 480

Asn Asn Gly Glu Arg Ala Ser Cys Glu Ser Asp Val Leu His Phe Thr
            485                 490                 495

Ser Thr Thr Thr Ser Lys Asn Arg Ile Ile Ile Thr Trp His Arg Tyr
            500                 505                 510

Arg Pro Pro Asp Tyr Arg Asp Leu Ile Ser Phe Thr Val Tyr Tyr Lys
            515                 520                 525

Glu Ala Pro Phe Lys Asn Val Thr Glu Tyr Asp Gly Gln Asp Ala Cys
            530                 535                 540

Gly Ser Asn Ser Trp Asn Met Val Asp Val Asp Leu Pro Pro Asn Lys
545                 550                 555                 560

Asp Val Glu Pro Gly Ile Leu Leu His Gly Leu Lys Pro Trp Thr Gln
            565                 570                 575

Tyr Ala Val Tyr Val Lys Ala Val Thr Leu Thr Met Val Glu Asn Asp
            580                 585                 590

His Ile Arg Gly Ala Lys Ser Glu Ile Leu Tyr Ile Arg Thr Asn Ala
            595                 600                 605

Ser Val Pro Ser Ile Pro Leu Asp Val Leu Ser Ala Ser Asn Ser Ser
            610                 615                 620

Ser Gln Leu Ile Val Lys Trp Asn Pro Pro Ser Leu Pro Asn Gly Asn
625                 630                 635                 640

```
Leu Ser Tyr Tyr Ile Val Arg Trp Gln Arg Gln Pro Gln Asp Gly Tyr
                645                 650                 655

Leu Tyr Arg His Asn Tyr Cys Ser Lys Asp Lys Ile Pro Ile Arg Lys
        660                 665                 670

Tyr Ala Asp Gly Thr Ile Asp Ile Glu Glu Val Thr Glu Asn Pro Lys
            675                 680                 685

Thr Glu Val Cys Gly Gly Lys Gly Pro Cys Cys Ala Cys Pro Lys
        690                 695                 700

Thr Glu Ala Glu Lys Gln Ala Lys Glu Glu Ala Glu Tyr Arg Lys
705                 710                 715                 720

Val Phe Glu Asn Phe Leu His Asn Ser Ile Phe Val Pro Arg Pro Glu
                725                 730                 735

Arg Lys Arg Arg Asp Val Met Gln Val Ala Asn Thr Thr Met Ser Ser
            740                 745                 750

Arg Ser Arg Asn Thr Thr Ala Ala Asp Thr Tyr Asn Ile Thr Asp Pro
        755                 760                 765

Glu Glu Leu Glu Thr Glu Tyr Pro Phe Phe Glu Ser Arg Val Asp Asn
    770                 775                 780

Lys Glu Arg Thr Val Ile Ser Asn Leu Arg Pro Phe Thr Leu Tyr Arg
785                 790                 795                 800

Ile Asp Ile His Ser Cys Asn His Glu Ala Glu Lys Leu Gly Cys Ser
                805                 810                 815

Ala Ser Asn Phe Val Phe Ala Arg Thr Met Pro Ala Glu Gly Ala Asp
            820                 825                 830

Asp Ile Pro Gly Pro Val Thr Trp Glu Pro Arg Pro Glu Asn Ser Ile
        835                 840                 845

Phe Leu Lys Trp Pro Glu Pro Glu Asn Pro Asn Gly Leu Ile Leu Met
    850                 855                 860

Tyr Glu Ile Lys Tyr Gly Ser Gln Val Glu Asp Gln Arg Glu Cys Val
865                 870                 875                 880

Ser Arg Gln Glu Tyr Arg Lys Tyr Gly Gly Ala Lys Leu Asn Arg Leu
                885                 890                 895

Asn Pro Gly Asn Tyr Thr Ala Arg Ile Gln Ala Thr Ser Leu Ser Gly
            900                 905                 910

Asn Gly Ser Trp Thr Asp Pro Val Phe Phe Tyr Val Gln Ala Lys Thr
        915                 920                 925

Gly Tyr Glu Asn Phe Ile His Leu Ile Ile Ala Leu Pro Val Ala Val
    930                 935                 940

Leu Leu Ile Val Gly Gly Leu Val Ile Met Leu Tyr Val Phe His Arg
945                 950                 955                 960

Lys Arg Asn Asn Ser Arg Leu Gly Asn Gly Val Leu Tyr Ala Ser Val
                965                 970                 975

Asn Pro Glu Tyr Phe Ser Ala Ala Asp Val Tyr Val Pro Asp Glu Trp
            980                 985                 990

Glu Val Ala Arg Glu Lys Ile Thr Met Ser Arg Glu Leu Gly Gln Gly
        995                 1000                1005

Ser Phe Gly Met Val Tyr Glu Gly Val Ala Lys Gly Val Val Lys
    1010                1015                1020

Asp Glu Pro Glu Thr Arg Val Ala Ile Lys Thr Val Asn Glu Ala
    1025                1030                1035

Ala Ser Met Arg Glu Arg Ile Glu Phe Leu Asn Glu Ala Ser Val
    1040                1045                1050

Met Lys Glu Phe Asn Cys His His Val Val Arg Leu Leu Gly Val
```

Val Ser Gln Gly Gln Pro Thr Leu Val Ile Met Glu Leu Met Thr
1070            1075                1080

Arg Gly Asp Leu Lys Ser Tyr Leu Arg Ser Leu Arg Pro Glu Met
1085            1090                1095

Glu Asn Asn Pro Val Leu Ala Pro Pro Ser Leu Ser Lys Met Ile
1100            1105                1110

Gln Met Ala Gly Glu Ile Ala Asp Gly Met Ala Tyr Leu Asn Ala
1115            1120                1125

Asn Lys Phe Val His Arg Asp Leu Ala Ala Arg Asn Cys Met Val
1130            1135                1140

Ala Glu Asp Phe Thr Val Lys Ile Gly Asp Phe Gly Met Thr Arg
1145            1150                1155

Asp Ile Tyr Glu Thr Asp Tyr Tyr Arg Lys Gly Gly Lys Gly Leu
1160            1165                1170

Leu Pro Val Arg Trp Met Ser Pro Glu Ser Leu Lys Asp Gly Val
1175            1180                1185

Phe Thr Thr Tyr Ser Asp Val Trp Ser Phe Gly Val Val Leu Trp
1190            1195                1200

Glu Ile Ala Thr Leu Ala Glu Gln Pro Tyr Gln Gly Leu Ser Asn
1205            1210                1215

Glu Gln Val Leu Arg Phe Val Met Glu Gly Gly Leu Leu Asp Lys
1220            1225                1230

Pro Asp Asn Cys Pro Asp Met Leu Phe Glu Leu Met Arg Met Cys
1235            1240                1245

Trp Gln Tyr Asn Pro Lys Met Arg Pro Ser Phe Leu Glu Ile Ile
1250            1255                1260

Ser Ser Ile Lys Glu Glu Met Glu Pro Gly Phe Arg Glu Val Ser
1265            1270                1275

Phe Tyr Tyr Ser Glu Glu Asn Lys Leu Pro Glu Pro Glu Glu Leu
1280            1285                1290

Asp Leu Glu Pro Glu Asn Met Glu Ser Val Pro Leu Asp Pro Ser
1295            1300                1305

Ala Ser Ser Ser Ser Leu Pro Leu Pro Asp Arg His Ser Gly His
1310            1315                1320

Lys Ala Glu Asn Gly Pro Gly Pro Gly Val Leu Val Leu Arg Ala
1325            1330                1335

Ser Phe Asp Glu Arg Gln Pro Tyr Ala His Met Asn Gly Gly Arg
1340            1345                1350

Lys Asn Glu Arg Ala Leu Pro Leu Pro Gln Ser Ser Thr Cys
1355            1360                1365

<210> SEQ ID NO 4
<211> LENGTH: 95
<212> TYPE: DNA
<213> ORGANISM: Artificial Sequence
<220> FEATURE:
<223> OTHER INFORMATION: Synthetic construct

<400> SEQUENCE: 4
tgctgttgac agtgagcgca ggaattataa tgcttatcta tagtgaagcc acagatgtat    60
agataagcat tataattcct atgcctactg cctcg    95

<210> SEQ ID NO 5
<211> LENGTH: 97

```
<212> TYPE: DNA
<213> ORGANISM: Artificial Sequence
<220> FEATURE:
<223> OTHER INFORMATION: Synthetic construct

<400> SEQUENCE: 5
tgctgttgac agtgagcgca agtgtgttca ttaatgttta tagtgaagcc acagatgtat      60
aaacattaat gaacacactt atgcctactg cctcgga                              97

<210> SEQ ID NO 6
<211> LENGTH: 97
<212> TYPE: DNA
<213> ORGANISM: Artificial Sequence
<220> FEATURE:
<223> OTHER INFORMATION: Synthetic construct

<400> SEQUENCE: 6
tgctgttgac agtgagcgac cgggacaacg tttattacta tagtgaagcc acagatgtat      60
agtaataaac gttgtcccgg gtgcctactg cctcgga                              97
```

THERAPEUTIC COMBINATIONS USING IGF1R PATHWAY INHIBITORS, AND METHODS TO PREDICT ANTI-IGF1R THERAPEUTIC EFFICACY

CLAIM TO BENEFIT OF PRIOR APPLICATION

This application claims the benefit of U.S. Provisional Application No. 62/635,241, filed on Feb. 26, 2018, which is incorporated herein by reference in its entirety.

STATEMENT REGARDING FEDERALLY SPONSORED RESEARCH

This invention was made with government support under grant numbers CA094118, GM008424, CA224567, and CA203154 awarded by the National Institutes of Health and by the grant number W81XWH-17-1-0003 awarded by the U.S. Army Medical Research and Materiel Command (ARMY/MRMC). The Government has certain rights in the invention.

FIELD

The disclosure generally relates to cancer (e.g., breast cancer), cancer treatments, and predictive methods for cancer treatments. The disclosure further relates to combination treatments, which can be synergistic, and the identification of patients who may benefit from such treatments.

BACKGROUND

Insulin-like growth factor 1 (IGF1) is a circulating endocrine hormone that is a major regulator of organismal growth and development. IGF1, in combination with estrogen, is essential for normal mammary gland development, and this pathway is deregulated in the initiation and progression of breast cancer. Many studies have shown the ability of the IGF1 receptor (IGF1R) to promote mammary tumorigenesis and metastasis. When constitutively activated, IGF1R transforms mammary epithelial cells, increases migration and invasion, and induces epithelial to mesenchymal transition (EMT) via the NFkB pathway and upregulation of Snail.

Based on these observations, both small molecule tyrosine kinase inhibitors and monoclonal antibodies against IGF1R were tested in clinical trials in breast cancer. Although as many as 50% of breast tumors express IGF1R, these trials unfortunately only identified a small subset of patients showing a therapeutic response to IGF1R targeted therapy. What is needed are new therapeutics and diagnostics for diagnosing and treating IGF1R sensitive cancers including breast cancers.

SUMMARY

The disclosed subject matter relates to methods for treating cancer (e.g., breast cancer), and methods for predicting therapeutic responses to cancer therapies. Current methods of using anti-IGF1R therapeutics for treatment of cancers have been largely unsuccessful despite an abundance of in vitro data suggesting that such treatments should be effective for cancer patients. The present disclosure improves upon the art by providing combination therapies comprising an IGF1R pathway inhibitor which are effective for treating cancer. The combination therapies are administered to subjects based in part on the discovery that E-cadherin levels influence efficacy of IGF1R pathway inhibitors in cancer patients. The combination therapies can have synergistic effects in patient populations affected by tumors having reduced E-cadherin levels. Additionally, disclosed methods provide effective combination therapies comprising an IGF1R pathway inhibitor for patient populations having E-cadherin levels which are not reduced, and in which the therapies are more effective than administration of an anti-IGF1R therapeutic alone. Also based on the discovered relationship between E-cadherin levels and efficacy of IGF1R pathway inhibitors are methods to predict therapeutic responses to IGF1R pathway inhibitors.

In some aspects, disclosed herein are methods of treating a subject with a cancer (such as, for example, an estrogen receptor-positive (ER+) breast cancer) comprising obtaining a sample of the cancer from the subject; determining a level of E-cadherin in the sample is reduced compared to a control; and administering a therapeutically effective amount of an IGF1R pathway inhibitor and an endocrine therapeutic. In some embodiments, the control comprises one or more non-cancerous mammary epithelial cells of the subject. In some embodiments, the cancer can be a ER+ breast cancer such as an invasive lobular breast cancer (ILC). In some embodiments, the IGF1R pathway inhibitor comprises OSI-906, BMS-754807, BEZ235, or a combination thereof. In some embodiments, the endocrine therapeutic comprises tamoxifen, ICI 182,780, or a combination thereof. In some embodiments, the level of E-cadherin is reduced by at least 50% compared to the control. In some embodiments, the determining step comprises determining a level of E-cadherin polypeptide expression.

Also disclosed herein are methods to treat a cancer in a subject comprising administering a therapeutically effective amount of an IGF1R pathway inhibitor and an E-cadherin inhibitor. In some embodiments, a sample of the cancer from the subject comprises a level of E-cadherin which is not reduced compared to a control. In some embodiments, the level of E-cadherin is a level of E-cadherin polypeptide expression. In some embodiments, the control comprises one or more non-cancerous cells of the subject which are of a same cell type as a cell of the sample. In some embodiments, the IGF1R pathway inhibitor comprises OSI-906, BMS-754807, BEZ235, or a combination thereof. In some embodiments, the E-cadherin inhibitor comprises a small interfering RNA (siRNA), a short hairpin RNA (shRNA), or a combination thereof. In some embodiments, the cancer comprises a breast cancer, or an invasive ductal breast carcinoma (IDC).

Also disclosed are methods to predict the likelihood a subject with a cancer (such as, for example a breast cancer or a gastrointestinal cancer) will respond therapeutically to a treatment comprising administering an IGF1R pathway inhibitor (i.e., detecting sensitivity of a cancer to IGF1R pathway inhibition), the method comprising obtaining a sample of the cancer from the subject; and determining (i.e., measuring or otherwise assaying) the level of E-cadherin in the sample; wherein a reduced level of E-cadherin compared to a control indicates the subject will respond therapeutically to the treatment (i.e., the cancer is sensitive to IGF1R pathway inhibition); and wherein a level of E-cadherin which is not reduced compared to the control indicates the subject will not respond therapeutically to the treatment. In some embodiments, the control comprises one or more non-cancerous mammary epithelial cells of the subject. In some embodiments, the determining step comprises determining a level of E-cadherin polypeptide expression. In some embodiments, the level of E-cadherin is reduced compared to the control, further comprising administering the treatment to the subject. In some embodiments, the level of E-cadherin is reduced by at least 50% compared to the control. In some embodiments, the cancer is a breast cancer such as, for example, an estrogen receptor-positive (ER+) breast cancer, and the treatment further comprises administering an endocrine therapeutic. In some embodiments, the breast cancer comprises an invasive lobular breast cancer (ILC).

Also disclosed herein are methods of increasing the sensitivity of a cancer in a subject to an IGF1 pathway inhibitor comprising administering to the subject a therapeutically effective amount of an E-cadherin inhibitor.

Additional aspects and advantages of the disclosure will be set forth, in part, in the detailed description and any claims which follow, and in part will be derived from the detailed description or can be learned by practice of the various aspects of the disclosure. The advantages described below will be realized and attained by means of the elements and combinations particularly pointed out in the appended claims. It is to be understood that both the foregoing general description and the following detailed description are exemplary and explanatory only and are not restrictive of the disclosure.

BRIEF DESCRIPTION OF THE DRAWINGS

The accompanying drawings, which are incorporated in and constitute a part of this specification, illustrate certain examples of the present disclosure and together with the description, serve to explain, without limitation, the principles of the disclosure. Like numbers represent the same element(s) throughout the figures.

In FIG. 1D, MCF-7 cells were treated with 25 μg/ml HECD-1 antibody (HECD-1) or no antibody (CTRL) for 24 hours and imaged by phase-contrast microscopy for dissociation of adherens junctions (right two panels). Cells were stimulated with Vhc or 10 nM IGF1 for 10 min and IGF1R and Akt signaling assessed by immunoblot (left panel). In FIG. 1E, MCF-7 cells were plated at sub-confluency (200 k cells in 6-well; "Sub-confluent") or high confluency (800 k cells; "Confluent") and then stimulated with either Vhc or 10 nM IGF1 for 10 min. IGF1R signaling was assessed by immunoblot (top panel). Representative phase-contrast microscopy images of the cell plating densities are shown (bottom two panels). In FIG. 1F, MCF-7 (left panel) and ZR75.1 (right panel) cells transfected with control siRNA (siSCR) or anti-CDH1 siRNA (siCDH1) were serum-starved and stimulated with 10 nM IGF1 for 17 hours and DNA stained with propidium iodide to measure cell cycle profile. The percent of cells in the IGF1/Vhc conditions in the S- and G2/M phases of the cell cycle for siSCR and siCDH1 are shown (representative experiment shown; n=2 or 3 each with 3 biological replicates).

In FIG. 3B, cells were serum-starved and stimulated with 10 nM IGF1 for 17 hours and DNA stained with propidium iodide to measure cell cycle profile. The percent of cells in the IGF1/Vhc conditions in the S- and G2/M phases of the cell cycle for empty and hE-cad are shown (one independent experiment, n=3 biological replicates).

FIG. 4A: OSI-906, 2D; FIG. 4B: OSI-906, ULA; FIG. 4C: BMS-754807, 2D; FIG. 4D: BMS-754807, ULA. The CellTiter Glo assay was used to assess cell viability (relative luminescence). EC50 values for viability were calculated by non-linear regression and statistical differences evaluated using sum-of-squares Global f-test (p<0.05; representative experiment shown; n=3 each with 6 biological replicates).

FIGS. 7A, 7B, 7C, 7D, 7E, 7F, 7G, 7H, 7I, 7J, and 7K show that proximity ligation assay reveals direct interaction between IGF1R and E-cadherin and recruitment of IG1R to adherens junctions. In situ proximity ligation assay (PLA) was used to analyze the direct interaction between IGF1R and E-cadherin in breast cancer cells. MCF-7 (FIG. 7A) and T47D (FIG. 7B) cells were plated on coverslips, fixed, and stained with IGF1R and E-cadherin antibody overnight. The Duolink (Sigma) protocol was followed and coverslips were imaged using confocal microscopy to reveal red puncta. MCF-7 cells transfected with anti-CDH1 siRNA (siCDH1; FIG. 7C) or anti-IGF1R siRNA (siIGF1R; FIG. 7D) were used as negative controls for the assay to assess primary antibody specificity. MCF-7 cells were plated on coverslips and treated with either vehicle control (Vhc) (FIG. 7E) or 10 nM IGF1 for 30 minutes (FIG. 7F), 6 hours (FIG. 7G), or 24 hours (FIG. 7H). PLA protocol for IGF1R and E-cadherin was followed as described above. In FIG. 7I, red puncta and nuclei (stained with DAPI) were quantified and displayed as a ratio of puncta/nuclei. All puncta and nuclei in 60× images were counted. One-way ANOVA was used to determine significant difference between groups (p<0.05; one independent experiment, n=5 images per slide counted). Further, IGF1R (green; second column from left) and E-cadherin (red; third column from left) were analyzed for co-localization (merge; fourth column from left) by immunofluorescence staining in MCF-7 cells transfected with siSCR (FIG. 7J) or siCDH1 (FIG. 7K). DNA was stained by Hoechst stain to identify cells (left-most column).

FIGS. 8A, 8B, 8C, 8D, 8E, and 8f show IGF1R and E-cadherin primary antibodies and Duolink secondary antibody probes used for proximity ligation assay are specific for the IGF1R-E-cadherin interaction. MCF-7 cells were reverse transfected with siSCR (FIG. 8A), siCDH1 (FIG. 8B), or siIGF1R (FIG. 8C) siRNA for 48 hours and plated on coverslips. Transfected cells were fixed and immunostained for IGF1R (green; second column from left) and E-cadherin (red; third column from left) overnight, then imaged using confocal microscopy and merged (fourth column from left) to demonstrate knockdown efficiency. DNA was stained by Hoechst stain to identify cells (left-most column). Non-transfected MCF-7 cells were plated on coverslips, fixed, and stained with either E-cadherin antibody alone (FIG. 8D), IGF1R antibody alone (FIG. 8E), or no primary antibody (FIG. 8F) overnight. The Duolink (Sigma) protocol was followed and coverslips were imaged using confocal microscopy to assess non-specific interaction of Duolink secondary antibody probes.

FIGS. 9A, 9B, 9C, 9D, 9E, 9F, and 9G show IGF1-IGF1R pathway is active in invasive lobular breast carcinoma with genetic loss of CDH1. SUM44PE (FIG. 9A), MDA-MB-134 (FIG. 9B), and BCK4 (FIG. 9C) ILC cells were immunostained for IGF1R (green; second column from left) and E-cadherin (red; third column from left) and imaged by confocal microscopy, and the results merged (fourth column from left). DNA was stained by Hoechst stain to identify cells (left-most column). Of note, BCK4 cells were imaged at an increased exposure compared to MM134 and SUM44PE cells. CDH1 mRNA (FIG. 9D), IGF1 mRNA (FIG. 9E), and pIGF1R Y1135 & Y1136 (FIG. 9F) levels in ER+ IDC compared to ER+ ILC in TCGA were plotted using RNAseq (log 2 TPM+1) and RPPA (median normalized) data. The TCGA cohort includes n=417 IDC cases and n=137 ILC cases that have matched data for RNAseq and RPPA. Man-Whitney test was used to determine significant differences in expression level between the two subtypes, p<0.05). In FIG. 9G, correlation between pIGF1R and IGF1 ligand expression is plotted for IDC (left panel) and ILC (right panel). Spearman's rank correlation was used to demonstrate the correlation between the two variables with significance as defined by p<0.05.

DETAILED DESCRIPTION

Figure 1A:
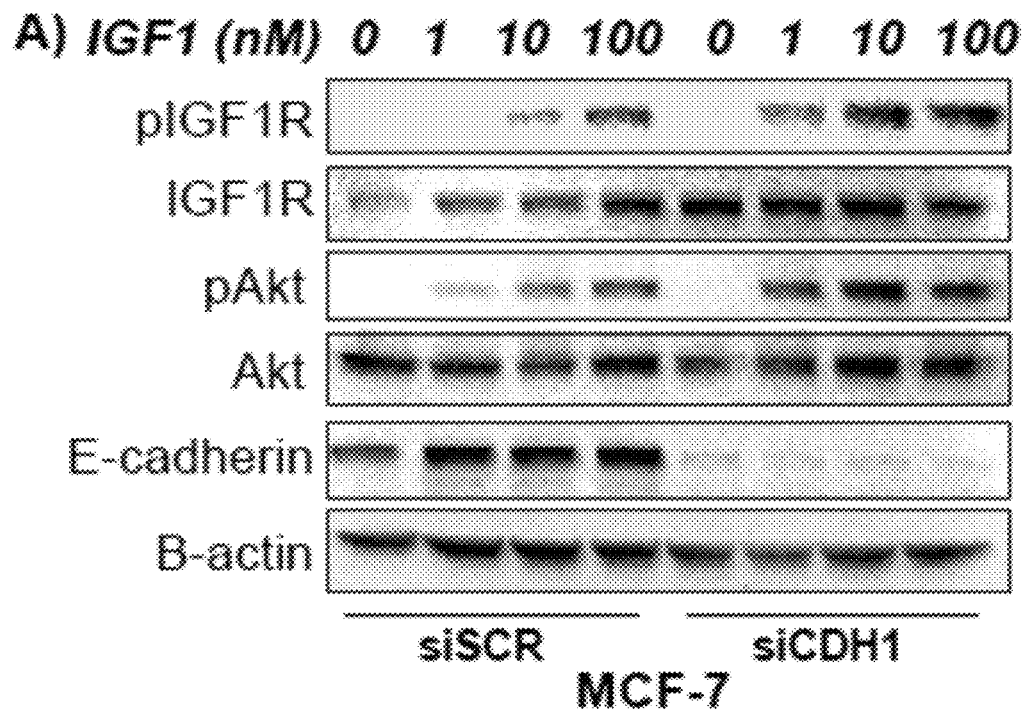
FIGS. 1A, 1B, 1C, 1D, 1E, and 1F show loss or inhibition of E-cadherin (CDH1) expression enhances IGF1R signaling. MCF-7 (FIG. 1A), ZR75.1 (FIG. 1B), and T47D (FIG. 1C) breast cancer cells transfected with SCR (siSCR) or CDH1 (siCDH1) siRNA were stimulated with increasing doses of IGF1 (0-100 nM) for 10 min. IGF1R and Akt signaling was assessed by immunoblot. IGF1R expression could routinely not be detected in ZR75.1.

The following description of the disclosure is provided as an enabling teaching of the disclosure in its best, currently known embodiment(s). To this end, those skilled in the relevant art will recognize and appreciate that many changes can be made to the various embodiments of the invention described herein, while still obtaining the beneficial results of the present disclosure. It will also be apparent that some of the desired benefits of the present disclosure can be obtained by selecting some of the features of the present disclosure without utilizing other features. Accordingly, those who work in the art will recognize that many modifications and adaptations to the present disclosure are possible and can even be desirable in certain circumstances and are a part of the present disclosure. Thus, the following description is provided as illustrative of the principles of the present disclosure and not in limitation thereof.

Terminology

Unless defined otherwise, all technical and scientific terms used herein have the same meaning as commonly understood to one of ordinary skill in the art to which this invention belongs. The following definitions are provided for the full understanding of terms used in this specification.

Disclosed are the components to be used to prepare the disclosed compositions as well as the compositions themselves to be used within the methods disclosed herein. These and other materials are disclosed herein, and it is understood that when combinations, subsets, interactions, groups, etc. of these materials are disclosed that while specific reference of each various individual and collective combinations and permutation of these compounds may not be explicitly disclosed, each is specifically contemplated and described herein. For example, if a particular compound is disclosed and discussed and a number of modifications that can be made to the compound are discussed, specifically contemplated is each and every combination and permutation of the compound and the modifications that are possible unless specifically indicated to the contrary. Thus, if a class of compounds A, B, and C are disclosed as well as a class of compounds D, E, and F and an example of a combination compound, or, for example, a combination compound comprising A-D is disclosed, then even if each is not individually recited each is individually and collectively contemplated meaning combinations, A-E, A-F, B-D, B-E, B-F, C-D, C-E, and C-F are considered disclosed. Likewise, any subset or combination of these is also disclosed. Thus, for example, the sub-group of A-E, B-F, and C-E would be considered disclosed. This concept applies to all aspects of this application including, but not limited to, steps in methods of making and using the disclosed compositions. Thus, if there are a variety of additional steps that can be performed it is understood that each of these additional steps can be performed with any specific embodiment or combination of embodiments of the disclosed methods.

It is understood that the compositions disclosed herein have certain functions. Disclosed herein are certain structural requirements for performing the disclosed functions, and it is understood that there are a variety of structures which can perform the same function which are related to the disclosed structures, and that these structures will ultimately achieve the same result.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is no way intended that an order be inferred, in any respect. This holds for any possible non-express basis for interpretation, including: matters of logic with respect to arrangement of steps or operational flow; plain meaning derived from grammatical organization or punctuation; and the number or type of embodiments described in the specification.

As used in the specification and claims, the singular form "a," "an," and "the" include plural references unless the context clearly dictates otherwise. For example, the term "an agent" includes a plurality of agents, including mixtures thereof.

As used herein, the terms "may," "optionally," and "may optionally" are used interchangeably and are meant to include cases in which the condition occurs as well as cases in which the condition does not occur. Thus, for example, the statement that a formulation "may include an excipient" encompasses cases in which the formulation includes an excipient as well as cases in which the formulation does not include an excipient.

Ranges can be expressed as from "about" one particular value, and/or to "about" another particular value. When such a range is expressed, another embodiment includes from the one particular value and/or to the other particular value. Similarly, when values are expressed as approximations, by use of the antecedent "about," it will be understood that the particular value forms another embodiment. It is also understood that the endpoints of each of the ranges are significant both in relation to the other endpoint, and independently of the other endpoint. It is also understood that there are a number of values disclosed herein, and that each value is also herein disclosed as "about" that particular value in addition to the value itself. For example, if the value "10" is disclosed, then "about 10" is also disclosed.

The terms "about" and "approximately" are defined as being "close to" as understood by one of ordinary skill in the art. In some non-limiting embodiments, the terms are defined to be within 10% of the associated value provided. In some non-limiting embodiments, the terms are defined to be within 5%. In still other non-limiting embodiments, the terms are defined to be within 1%.

Grammatical variations of "administer," "administration," and "administering" to a subject include any route of introducing or delivering to a subject an agent. Administration can be carried out by any suitable route, including oral, topical, intravenous, subcutaneous, transcutaneous, transdermal, intramuscular, intra joint, parenteral, intra-arteriole, intradermal, intraventricular, intracranial, intraperitoneal, intralesional, intranasal, rectal, vaginal, by inhalation, via an implanted reservoir, parenteral (e.g., subcutaneous, intravenous, intramuscular, intra-articular, intra-synovial, intrasternal, intrathecal, intraperitoneal, intrahepatic, intralesional, and intracranial injections or infusion techniques), and the like. "Concurrent administration", "administration in combination", "simultaneous administration" or "administered simultaneously" as used herein, means that the compounds are administered at the same point in time, overlapping in time, or one following the other. In the latter case, the two compounds are administered at times sufficiently close that the results observed are indistinguishable from those achieved when the compounds are administered at the same point in time. "Systemic administration" refers to the introducing or delivering to a subject an agent via a route which introduces or delivers the agent to extensive areas of the subject's body (e.g. greater than 50% of the body), for example through entrance into the circulatory or lymph systems. By contrast, "local administration" refers to the introducing or delivery to a subject an agent via a route which introduces or delivers the agent to the area or area immediately adjacent to the point of administration and does not introduce the agent systemically in a therapeutically significant amount. For example, locally administered agents are easily detectable in the local vicinity of the point of administration, but are undetectable or detectable at negligible amounts in distal parts of the subject's body. Administration includes self-administration and the administration by another.

"Comprising" is intended to mean that the compositions, methods, etc. include the recited elements, but do not exclude others. It is expressly understood that where the compositions, systems, or methods use the term comprising, the specification also discloses the same compositions, systems, or methods using the terms "consisting essentially of" and "consisting of" as it relates to the modified elements.

"Identical" or percent "identity," in the context of two or more nucleic acids or polypeptide sequences, refer to two or more sequences or subsequences that are the same or have a specified percentage of amino acid residues or nucleotides that are the same (e.g., about 60% identity, preferably 61%, 62%, 63%, 64%, 65%, 66%, 67%, 68%, 69%, 70%, 71%, 72%, 73%, 74%, 75%, 76%, 77%, 78%, 79%, 80%, 81%, 82%, 83%, 84%, 85%, 86%, 87%, 88%, 89%, 90%, 91%, 92%, 93%, 94%, 95%, 96%, 97%, 98%, 99% or higher identity over a specified region when compared and aligned for maximum correspondence over a comparison window or designated region) as measured using a BLAST or BLAST 2.0 sequence comparison algorithms with default parameters described below, or by manual alignment and visual inspection (see, e.g., NCBI web site or the like). Such sequences are then said to be "substantially identical." This definition also refers to, or may be applied to, the complement of a test sequence. The definition also includes sequences that have deletions and/or additions, as well as those that have substitutions. As described below, the preferred algorithms can account for gaps and the like. Preferably, identity exists over a region that is at least about 10 amino acids or 20 nucleotides in length, or more preferably over a region that is 10-50 amino acids or 20-50 nucleotides in length. As used herein, percent (%) amino acid sequence identity is defined as the percentage of amino acids in a candidate sequence that are identical to the amino acids in a reference sequence, after aligning the sequences and introducing gaps, if necessary, to achieve the maximum percent sequence identity. Alignment for purposes of determining percent sequence identity can be achieved in various ways that are within the skill in the art, for instance, using publicly available computer software such as BLAST, BLAST-2, ALIGN, ALIGN-2 or Megalign (DNASTAR) software. Appropriate parameters for measuring alignment, including any algorithms needed to achieve maximal alignment over the full-length of the sequences being compared can be determined by known methods.

For sequence comparisons, typically one sequence acts as a reference sequence, to which test sequences are compared. When using a sequence comparison algorithm, test and reference sequences are entered into a computer, subsequence coordinates are designated, if necessary, and sequence algorithm program parameters are designated. Preferably, default program parameters can be used, or alternative parameters can be designated. The sequence comparison algorithm then calculates the percent sequence identities for the test sequences relative to the reference sequence, based on the program parameters.

One example of an algorithm that is suitable for determining percent sequence identity and sequence similarity are the BLAST and BLAST 2.0 algorithms, which are described in Altschul et al. (1977) *Nuc. Acids Res.* 25:3389-3402, and Altschul et al. (1990) *J. Mol. Biol.* 215:403-410, respectively. Software for performing BLAST analyses is publicly available through the National Center for Biotechnology Information (http://www.ncbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al. (1990) *J. Mol. Biol.* 215:403-410). These initial neighborhood word hits act as seeds for initiating searches to find longer HSPs containing them. The word hits are extended in both directions along each sequence for as far as the cumulative alignment score can be increased. Cumulative scores are calculated using, for nucleotide sequences, the parameters M (reward score for a pair of matching residues; always >0) and N (penalty score for mismatching residues; always <0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a wordlength (W) of 11, an expectation (E) or 10, M=5, N=−4 and a comparison of both strands. For amino acid sequences, the BLASTP program uses as defaults a wordlength of 3, and expectation (E) of 10, and the BLOSUM62 scoring matrix (see Henikoff and Henikoff (1989) *Proc. Natl. Acad. Sci. USA* 89:10915) alignments (B) of 50, expectation (E) of 10, M=5, N=−4, and a comparison of both strands.

The BLAST algorithm also performs a statistical analysis of the similarity between two sequences (see, e.g., Karlin and Altschul (1993) *Proc. Natl. Acad. Sci. USA* 90:5873-5787). One measure of similarity provided by the BLAST algorithm is the smallest sum probability (P(N)), which provides an indication of the probability by which a match between two nucleotide or amino acid sequences would occur by chance. For example, a nucleic acid is considered similar to a reference sequence if the smallest sum probability in a comparison of the test nucleic acid to the reference nucleic acid is less than about 0.2, more preferably less than about 0.01.

"Pharmaceutically acceptable" component can refer to a component that is not biologically or otherwise undesirable, e.g., the component may be incorporated into a pharmaceutical formulation of the invention and administered to a subject as described herein without causing significant undesirable biological effects or interacting in a deleterious manner with any of the other components of the formulation in which it is contained. When used in reference to administration to a human, the term generally implies the component has met the required standards of toxicological and manufacturing testing or that it is included on the Inactive Ingredient Guide prepared by the U.S. Food and Drug Administration.

"Pharmaceutically acceptable carrier" (sometimes referred to as a "carrier") means a carrier or excipient that is useful in preparing a pharmaceutical or therapeutic composition that is generally safe and non-toxic, and includes a carrier that is acceptable for veterinary and/or human pharmaceutical or therapeutic use. The terms "carrier" or "pharmaceutically acceptable carrier" can include, but are not limited to, phosphate buffered saline solution, water, emulsions (such as an oil/water or water/oil emulsion) and/or various types of wetting agents. As used herein, the term "carrier" encompasses, but is not limited to, any excipient, diluent, filler, salt, buffer, stabilizer, solubilizer, lipid, stabilizer, or other material well known in the art for use in pharmaceutical formulations and as described further herein.

"Pharmacologically active" (or simply "active"), as in a "pharmacologically active" derivative or analog, can refer to a derivative or analog (e.g., a salt, ester, amide, conjugate, metabolite, isomer, fragment, etc.) having the same type of pharmacological activity as the parent compound and approximately equivalent in degree.

"Polynucleotide" and "oligonucleotide" are used interchangeably, and refer to a polymeric form of nucleotides of any length, either deoxyribonucleotides or ribonucleotides, or analogs thereof. Polynucleotides may have any three-dimensional structure, and may perform any function, known or unknown. The following are non-limiting examples of polynucleotides: a gene or gene fragment, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide may comprise modified nucleotides, such as methylated nucleotides and nucleotide analogs. If present, modifications to the nucleotide structure may be imparted before or after assembly of the polymer. The sequence of nucleotides may be interrupted by non-nucleotide components. A polynucleotide may be further modified after polymerization, such as by conjugation with a labeling component. A polynucleotide is composed of a specific sequence of four nucleotide bases: adenine (A); cytosine (C); guanine (G); thymine (T); and uracil (U) for thymine (T) when the polynucleotide is RNA. Thus, the term "polynucleotide sequence" is the alphabetical representation of a polynucleotide molecule.

"Peptide," "protein," and "polypeptide" are used interchangeably to refer to a natural or synthetic molecule comprising two or more amino acids linked by the carboxyl group of one amino acid to the alpha amino group of another. The amino acids may be natural or synthetic, and can contain chemical modifications such as disulfide bridges, substitution of radioisotopes, phosphorylation, substrate chelation (e.g., chelation of iron or copper atoms), glycosylation, acetylation, formylation, amidation, biotinylation, and a wide range of other modifications. A polypeptide may be attached to other molecules, for instance molecules required for function. Examples of molecules which may be attached to a polypeptide include, without limitation, cofactors, polynucleotides, lipids, metal ions, phosphate, etc. Non-limiting examples of polypeptides include peptide fragments, denatured/unstructured polypeptides, polypeptides having quaternary or aggregated structures, etc. There is expressly no requirement that a polypeptide must contain an intended function; a polypeptide can be functional, non-functional, function for unexpected/unintended purposes, or have unknown function. A polypeptide is comprised of approximately twenty, standard naturally occurring amino acids, although natural and synthetic amino acids which are not members of the standard twenty amino acids may also be used. The standard twenty amino acids include alanine (Ala, A), arginine (Arg, R), asparagine (Asn, N), aspartic acid (Asp, D), cysteine (Cys, C), glutamine (Gln, Q), glutamic acid (Glu, E), glycine (Gly, G), histidine, (His, H), isoleucine (Ile, I), leucine (Leu, L), lysine (Lys, K), methionine (Met, M), phenylalanine (Phe, F), proline (Pro, P), serine (Ser, S), threonine (Thr, T), tryptophan (Trp, W), tyrosine (Tyr, Y), and valine (Val, V). The terms "polypeptide sequence" or "amino acid sequence" are an alphabetical representation of a polypeptide molecule.

A "subject" can be any mammalian subject, for example a human, dog, cat, pig, cow, horse, mouse, rabbit, etc. In some embodiments, the subject is a primate, particularly a human. The subject can be a male or female of any age, race, creed, ethnicity, socio-economic status, or other general classifiers. In some embodiments, the subject is a human. In some embodiments, the subject is a female, although it is duly noted that a male can be diagnosed with breast cancer.

"Therapeutically effective amount" or "therapeutically effective dose" of a composition (e.g. a composition comprising an agent) refers to an amount that is effective to achieve a desired therapeutic result (e.g., reducing the size of a tumor or reducing the number of tumors). Therapeutically effective amounts of a given therapeutic agent will typically vary with respect to factors such as the type and severity of the disorder or disease being treated and the age, gender, and weight of the subject. The term can also refer to an amount of a therapeutic agent, or a rate of delivery of a therapeutic agent (e.g., amount over time), effective to facilitate a desired therapeutic effect, such as pain relief. The precise desired therapeutic effect will vary according to the condition to be treated, the tolerance of the subject, the agent and/or agent formulation to be administered (e.g., the potency of the therapeutic agent, the concentration of agent in the formulation, and the like), and a variety of other factors that are appreciated by those of ordinary skill in the art. In some instances, a desired biological or medical response is achieved following administration of multiple dosages of the composition to the subject over a period of days, weeks, or years.

The terms "treat," "treating," "treatment," and grammatical variations thereof as used herein, include partially or completely delaying, curing, healing, alleviating, relieving, altering, remedying, ameliorating, improving, stabilizing, mitigating, and/or reducing the intensity or frequency of one or more diseases or conditions, symptoms of a disease or condition, or underlying causes of a disease or condition. Treatments according to the invention may be applied prophylactically, palliatively or remedially. Prophylactic treatments are administered to a subject prior to onset (e.g., before obvious signs of cancer), during early onset (e.g., upon initial signs and symptoms of cancer), or after an established development of cancer. Prophylactic administration can occur for several days to years prior to the manifestation of symptoms.

In some instances, the terms "treat", "treating", "treatment" and grammatical variations thereof, include reducing the size of a tumor or reducing the number of tumors. The terms "treat", "treating", "treatment" and grammatical variations thereof, can also include reducing the appearance of tumors apart from the primary tumor (e.g., metastatic tumors) in other parts of the body. The terms "treat", "treating", "treatment" and grammatical variations thereof, can also include inducing or facilitating the clinical diagnosis of cancer remission. The terms "treat", "treating", "treatment" and grammatical variations thereof, can also include increasing life expectancy based on clinical average life expectancies, as known to one of skill in the art. Measurements of treatment can be compared with prior treatment(s) of the subject, inclusive of no treatment, or compared with the incidence of such symptom(s) in a general or study population.

Methods of Treating Cancer

The treatment and diagnostic methods disclosed herein relate to identifying and treating IGF1R sensitive cancers. Advances in early detection of cancer (including, breast cancer) and better understanding of the molecular underpinnings of the disease, have led to new therapies and biomarkers for response that have ultimately decreased mortality. However, significant mortality remains, and more research is required to understand why disease recurs and how to treat advanced/metastatic cancers (including, breast cancer).

Breast cancer has two major histologic subtypes, invasive ductal cancer (IDC) and invasive lobular cancer (ILC). ILC represents ~10-15% of invasive breast cancers and is defined by its near uniform loss of the gene CDH1 (E-cadherin). There has been a major recent push to understand ILC and identify appropriate therapies given its penchant for late recurrence and metastasis to unique organ sites. Molecular subtyping has identified several intrinsic subtypes of breast cancer (luminal A/B, HER2-enriched, and Basal-like). The lack of ER, PR and HER2 is often referred to as triple negative breast cancer (TNBC) the most aggressive subtype of invasive breast cancer that lacks any targeted therapy. TNBC can be further subdivided into several more subtypes, one of which is the mesenchymal subtype that is characterized by epigenetic downregulation of E-cadherin.

Alterations in the IGF1 signaling pathway are linked to the development and progression of multiple cancers including breast cancer. Insulin-like growth factor 1 and 2 (IGF1 and IGF2) are circulating endocrine hormones critical for normal body growth. IGF1 and IGF2 stimulate downstream signaling, primarily by binding and activating the type 1 insulin-like growth factor receptor (IGF1R). IGF1R is homologous to the insulin receptor (InsR). Indeed, although the affinities are much lower, IGF1 can bind and activate the InsR while, in turn, insulin can bind and activate IGF1R. IGF2 binds both receptors with similar affinities. In addition, a fetal form of InsR that has alternate splicing, termed InsR-A, has a high affinity for IGF2. Hybrid receptors composed of one chain of IGF1R and InsR are high affinity binders for both IGFs. Binding of IGF1 or IGF2 to IGF1R, hybrid receptors, and InsR-A results in auto-phosphorylation activation of intracellular signaling cascades. such as PI3K/AKT and RAS/MAPK/ERK1. Receptor signaling cascades regulate cell growth, survival, and motility and play critical roles in promoting tumorigenesis.

It is shown herein that IGF1R overexpression transforms mammary epithelial cells and causes EMT, and we generated the first transgenic mouse model of IGF1R overexpression which showed mammary tumorigenesis. Overexpression of the IGF1 ligand delayed mammary gland involution. It is also shown herein that the IGF1R downstream signaling intermediates (IRSs) undergo hormonal regulation during normal mammary gland development and when genetically deleted reduce lactational capacity. Accordingly, MMTV-IRS1 and 2 transgenic mice, both of which developed mammary tumors, were generated.

Preclinical laboratory data is validated in human samples. For example, 15% of TCGA-documented breast cancers contain genomic alterations in the IGF pathway including amplification of IGF1R, IRS2 and IGFBP4, and >45% of breast cancers (n=436/962) show mRNA alterations in at least one IGF family member. While somatic mutation of IGF family members has only recently been comprehensively described in primary breast cancer, a recent study showed an increase in IGF1R mutation in metastatic lobular breast cancer (Desmedt, GS-1-06, SABCS 2018). There is a large literature on germline polymorphisms in IGF1, IGF1R, and IGFBP3 associated with increased risk of breast cancers.

Tumor tissue microarrays show that 87% of primary breast tumors express IGF1R, and the active phosphorylated form of IGF1R/InsR, as measured by immunohistochemistry (IHC), is present in ~50% of breast cancers, where it correlates with poor survival. We previously examined IGF pathway activity by combining IGF-regulated mRNA levels into an 'IGF gene signature'. The IGF1 gene signature correlates significantly with numerous poor prognostic factors and expression of this signature is one of the strongest indicators of poor disease outcome in patients with breast cancer. We showed that the IGF signature is particularly high in TNBC, and levels correlate with response to IGF inhibition in a PDX model. In this proposal, we show that the IGF signature is high in ILC, with low levels of E-cadherin, consistent with IGF1R being active in these disease subtypes and a putative therapeutic target.

Targeting IGF1R will be a more effective and less toxic therapy for advanced cancers (including, but not limited to breast cancer). An IGF1-signature (IGF-sig) was previously developed based on microarray analyses, and a novel computational method to identify putative biomarkers of IGF1 signaling using a systems biology approach was reported. The latter was based on a proteomic screen using reverse phase protein array (RPPA) on 21 breast cancer cell lines stimulated with IGF1 over a time course. This computational model identified E-cadherin as one possible molecule involved in IGF1 signaling.

Although anti-IGF1R therapeutics were tested in clinical trials in breast cancer, the very low number of patients responding to the therapy suggests that a general protocol of administering anti-IGF1R therapeutics upon cancer diagnosis is unlikely to be successful in many patients. Thus, there remains a need to identify those patients that will benefit from anti-IGF1R therapeutics. Further, there remains a need to enhance the efficacy of anti-IGF1R therapeutics in patients. The compositions and methods disclosed herein address these and other needs.

IGF1R inhibitor sensitivity can be modulated the administration of endocrine therapeutics (such as, for example, tamoxifen, ICI 182,780 (ICI, also known as fulvestrant (Faslodex) and 7α,17β-[9-[(4,4,5,5,5-Pentafluoropentyl) sulfinyl]nonyl]estra-1,3,5(10)-triene-3,17-diol), and aromatase inhibitors such as aminoglutethimide, testolactaone (Teslac), anastrozole (Arimidex), letrozole (Femara), exemestane (Aromasin), vorozole (Rivizor), formestane (Lentaron), fadrozole (Afema), 1,4,6-Androstatriene-3,17-dione (ATD), and 4-androstene-3,6,17-trione (4-AT; also known as 6-OXO)). Unlike the largely unsuccessful clinical trials using IGF1R inhibitors alone, the methods can result in synergistic effects in subjects having tumors with reduced E-cadherin levels, which result in effective breast cancer treatment. Accordingly, disclosed herein are methods to treat cancers (including, for example gastrointestinal and estrogen receptor positive (ER+) breast cancers) by administering to subjects with a cancer, and effective amount of an IGF1R pathway inhibitor and an endocrine therapeutic. In one aspect, the methods are advantageous at least because the methods provide for the administration of combination therapies comprising an IGF1R pathway inhibitor which are effective for treating cancer.

The IGF1R pathway inhibitor described herein can include any one or more agents which upon administration to a subject, can inhibit the IGF1R pathway. "IGF1R," as used herein, refers to insulin like growth factor 1 receptor, which is a tetramer of 2 alpha and 2 beta chains linked by disulfide bonds. The alpha chains contribute to the formation of the ligand-binding domain(s), while the beta chain carries the kinase domain(s). In humans, x the IGF1R gene encodes the IGF1R polypeptide, which is then cleaved into the alpha and beta chains. In some embodiments, the IGF1R polypeptide is a polypeptide identified in one or more publicly available databases as follows: HGNC: 5465, Entrez Gene: 3480, Ensembl: ENSG00000140443, OMIM: 147370, and UniProtKB: P08069. In some embodiments, the IGFR1 comprises alpha and beta chains having an amino acid sequence which is at least 80% identical to amino acids 31-736 and 741-1367, respectively, of SEQ ID NO: 3. In some embodiments, the comprises alpha and beta chains having an amino acid sequence which is at least 85%, at least 90%, at least 95%, at least 98%, or at least 99% identical to amino acids 31-736 and 741-1367, respectively, of SEQ ID NO: 3.

The IGF1R pathway inhibitor can directly inhibit IGF1R, for example, by binding to the IGF1R protein, preventing tetramer formation of IGF1R, preventing tyrosine phosphorylation or tyrosine kinase activity of IGF1R, or preventing the transcription or translation of an IGF1R gene. Alternatively, the IGF1R pathway inhibitor can inhibit one or more other factors (e.g., one or more genes, proteins, mRNA) involved in the IGF1R pathway, including as examples insulin like growth factors 1 and 2 (IGF1 and IGF2), insulin receptor substrates (IRS), phosphoinositide 3-kinase (PI3K), AKT serine/threonine kinase 1 (AKT1), phosphatase and tensin homolog (PTEN), mechanistic target of rapamycin kinase (MTOR), S6 kinase, S6 ribosomal proteins, MAP kinases such as mitogen-activated protein kinase kinase 1 (MAP2K1), and extracellular signal-regulated kinases (ERKs). An IGF1R pathway inhibitor which inhibits one or more other factors involved in the IGF1R pathway should produce the same or similar effects as inhibiting IGF1R directly; administration of such an IGF1R pathway inhibitor should result in a therapeutic benefit when a level of E-cadherin in the sample is reduced compared to a control. Suitable IGF1R pathway inhibitors include, but are not limited to, tyrosine kinase inhibitors such as OSI-906 (OSI; also known as Linsitinib and cis-3-[8-amino-1-(2-phenyl-7-quinolinyl)imidazo[1,5-a]pyrazin-3-yl]-1-methyl-cyclobutanol)), BMS-754807 (BMS; also known as (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-Pyrrolidinecarboxamide), BVP 51004 (Biovitrum), XL228 (Exelixis), INSM-18 NDGA (Insmed); anti-IGF1R monoclonal antibodies such as figitumumab (CP-751871), ganitumab (AMG 479), dalotuzumab (MK-0646), cixutumumab (IMC-A12), R1507, SCH 717454 (19D12), AVE1642 (EM164), BIIB022; IGF1/2 ligand inhibitors such as MEDI-573 and Xentuzumab (BI 836845); PI3K inhibitors such as BEZ235 (BEZ; also known as dactolisib, NVP-BEZ235, and 4-[2,3-dihydro-3-methyl-2-oxo-8-(3-quinolinyl)-1H-imidazo[4,5-c]quinolin-1-yl]-α,α-dimethyl-benzeneacetonitrile); other IGF1R pathway inhibitors such as Picropodophyllin (PPP); and combinations thereof. In some embodiments, the IGF1R pathway inhibitor comprises OSI-906, BMS-754807, BEZ235, or a combination thereof.

As used herein, the term "endocrine therapeutic" refers to a composition that inhibits a hormone or hormone signaling involved in promoting growth or proliferation of cancer cells. In some embodiments, the endocrine therapeutic is an anti-estrogen or anti-estrogen receptor therapeutic. Suitable anti-estrogen or anti-estrogen receptor therapeutics include, but are not limited to, tamoxifen, ICI 182,780 (ICI; also known as fulvestrant (Faslodex) and 7α,17β-[9-[(4,4,5,5,5-Pentafluoropentyl)sulfinyl]nonyl]estra-1,3,5(10)-triene-3,17-diol), and aromatase inhibitors such as aminoglutethimide, testolactaone (Teslac), anastrozole (Arimidex), letrozole (Femara), exemestane (Aromasin), vorozole (Rivizor), formestane (Lentaron), fadrozole (Afema), 1,4,6-Androstatriene-3,17-dione (ATD), and 4-androstene-3,6,17-trione (4-AT; also known as 6-OXO), or combinations thereof. In some embodiments, the endocrine therapeutic comprises tamoxifen, ICI 182,780, or a combination thereof.

In some embodiments, the administration of an IGF1R pathway inhibitor and an endocrine therapeutic have synergistic effects. For example, such administration can result in synergistic reduction in tumor cell viability, inhibition of tumor cell growth, inhibition of tumor cell proliferation, inhibition of tumor cell metastasis, or combinations thereof. It is a surprising finding described herein that administration of an IGF1R pathway inhibitor and an endocrine therapeutic have synergistic effects in a subject having ER+ breast cancer in which the tumor has a reduced level of E-cadherin. For example, the disclosed methods can, in some embodiments, identify subjects which may benefit more greatly from administration of an IGF1R pathway inhibitor and thus, also the synergistic effects of administration of an IGF1R pathway inhibitor and an endocrine therapeutic.

It is understood and herein contemplated that the combination of an IGF1R inhibitor and endocrine therapeutic have the greatest effect on patients with depressed levels of E-cadherin. Accordingly, disclosed herein are methods of treating a subject with a cancer (such as, for example, an ER+ breast cancer or gastrointestinal cancer) comprising obtaining a cancerous tissue sample (such as, for example, a breast cancer tissue sample or gastrointestinal cancer tissue sample) from the subject; determining a level of E-cadherin in the sample is reduced compared to a control; and administering a therapeutically effective amount of an IGF1R pathway inhibitor and an endocrine therapeutic. In some aspect, the E-cadherin levels in the cancerous tissue sample can be are at least 50% reduced compared to a control. In some embodiments, the E-cadherin levels in the sample are at least 60%, at least 70%, at least 80%, at least 90%, at least 95%, at least 98%, or at least 99% reduced compared to a control.

Cadherins are cell adhesion molecules involved in forming adherens junctions between cells. Encoded in humans by the cdh1 gene, epithelial cadherin (E-cadherin) is a calcium-dependent, transmembrane glycoprotein which bridges adhesive interactions between the intracellular actin cytoskeleton and adjacent cells.

Insight into how E-cadherin affects the IGF1R signaling pathway is necessary to understand the oncogenic signaling network, specifically because the loss of E-cadherin i) is implicated in the ability of tumor cells to escape the primary tumor to potentially seed metastatic lesions and ii) is transcriptionally repressed and/or genetically lost in subsets of breast tumors.

One such subtype of breast cancer with diminished E-cadherin expression is invasive lobular breast carcinoma (ILC), accounting for 10-15% (approximately 30,000 cases/year in the US) of total breast cancer cases. ILC is defined by the loss of functional E-cadherin (CDH1), which occurs in 95% of ILC due to truncating mutations, loss of heterozygosity, and transcriptional repression. Due to the loss of E-cadherin, ILC cells grow in linear patterns throughout the breast tissue, lacking the ability to form adherens junctions, in contrast to the solid mass growth of the most frequent subtype of breast cancer, invasive ductal breast carcinoma (IDC). Interestingly, one of the most IGF1 responsive cell lines in the above-referenced proteomic data set was a human ILC cell line, MDA-MB-134-IV, that lacks E-cadherin protein expression and cell-cell junctions. As the loss of E-cadherin directly effects the sensitivity a cancer has to IGF1R inhibitor therapy, it is understood and herein recognized that by decreasing E-cadherin levels, sensitivity to IGF1R pathway inhibitors can be increased. Thus, in one aspect, disclosed herein are methods of increasing the sensitivity of a cancer in a subject to an IGF1R pathway inhibitor comprising administering to the subject an E-cadherin inhibitor. Similarly, as increases in the sensitivity of a cancer to IGF1R pathway inhibition can make a cancer more susceptible to IGF1R inhibition therapy and that IGF1R inhibitor sensitivity can be determined and modulated by the level of E-cadherin, it is understood that a treatment of a subject with a cancer to comprise both the administration of an E-cadherin inhibitor and an IGF1R inhibitor would have a synergistic effect of the therapeutic outcome for the subject. Thus, disclosed herein are methods of treating a cancer in a subject comprising administering to the subject an effective amount of an IGF1R pathway inhibitor and an E-cadherin inhibitor.

"E-cadherin," as used herein, refers to either E-cadherin polypeptide, also known as CD324 and uvomorulin, and previously known as cadherin 1 and UVO, or a polynucleotide encoding E-cadherin polypeptide. In humans, E-cadherin polypeptide is encoded by the CDH1 gene. In some embodiments, the E-cadherin is a polypeptide or polynucleotide identified in one or more publicly available databases as follows: HGNC: 1748, Entrez Gene: 999, Ensembl: ENSG00000039068, OMIM: 192090, and UniProtKB: P12830.

In some embodiments, the E-cadherin is a polypeptide comprising an amino acid sequence which is at least 80% identical to SEQ ID NO: 1. In some embodiments, the E-cadherin is a polypeptide comprising an amino acid sequence which is at least 85%, at least 90%, at least 95%, at least 98%, or at least 99% identical to SEQ ID NO: 1. In some embodiments, the E-cadherin is a polypeptide comprising SEQ ID NO: 1. In other embodiments, the E-cadherin is a fragment or portion of SEQ ID NO: 1.

In some embodiments, the E-cadherin is a polynucleotide comprising a nucleic acid sequence which is at least 70% identical to SEQ ID NO: 2. In some embodiments, the E-cadherin is a polynucleotide comprising a nucleic acid sequence which is at least 75%, at least 80%, at least 85%, at least 90%, at least 95%, at least 98%, or at least 99% identical to SEQ ID NO: 2. In some embodiments, the E-cadherin is a polynucleotide comprising the nucleic acid sequence of SEQ ID NO: 2. In other embodiments, the E-cadherin is a fragment or portion of SEQ ID NO: 2.

The E-cadherin inhibitor can include any one or more agents which upon administration to a subject, can inhibit E-cadherin. The E-cadherin inhibitor can directly inhibit E-cadherin, for example, by binding to the E-cadherin protein or preventing the transcription or translation of an E-cadherin gene (e.g., cdh1). Alternatively, the E-cadherin inhibitor can inhibit one or more other factors (e.g., one or more genes, proteins, mRNA) involved in the E-cadherin pathway. In some embodiments, the E-cadherin inhibitor can comprise an RNA interference (RNAi) modulator. RNAi modulators can be used to silence the expression of a gene (also known as "gene knock-down"), as opposed to genetic disruption of the gene (also known as "gene knock out"). RNAi modulators include, but are not limited to, small interfering RNA (siRNA), short hairpin RNA (shRNA), micro RNA (mRNA), trans-acting small interfering RNA (tasiRNA), long non-coding RNA (lncRNA), Piwi-interacting RNA (piRNA), among others. In some embodiments, the E-cadherin inhibitor can comprise a siRNA, a shRNA, or a combination thereof. In some embodiments, the E-cadherin inhibitor is a RNA polynucleotide comprising the nucleic acid sequence of SEQ ID NO: 5 or SEQ ID NO: 6. In some or further embodiments, the E-cadherin inhibitor can comprise a peptide inhibitor, for example and without limitation, the peptide inhibitors SWELYYPLRANL and SWELYYPL described in US 2015/0291933, which is incorporated by reference herein. In some embodiments, the E-cadherin inhibitor comprises an anti-E-cadherin antibody, for example and without limitation, a humanized version of 24E10 mAb (Cell Signaling Technology), 67A4 mAb (Santa Cruz Biotechnology), ECCD-2 mAb (ThermoFisher), 4A2C7 (ThermoFisher), ab15148 (Abcam), or other suitable anti-E-cadherin antibodies. In some instances, the E-cadherin inhibitor can be an epigenetic inhibitor of E-cadherin.

As noted above, the IGF1R pathway inhibitor described herein can include any one or more agents which upon administration to a subject, can inhibit the IGF1R pathway. The IGF1R pathway inhibitor can directly inhibit IGF1R, for example, by binding to the IGF1R protein, preventing tetramer formation of IGF1R, preventing tyrosine phosphorylation or tyrosine kinase activity of IGF1R, or preventing the transcription or translation of an IGF1R gene. Alternatively, the IGF1R pathway inhibitor can inhibit one or more other factors (e.g., one or more genes, proteins, mRNA) involved in the IGF1R pathway, including as examples insulin like growth factors 1 and 2 (IGF1 and IGF2), insulin receptor substrates (IRS), phosphoinositide 3-kinase (PI3K), AKT serine/threonine kinase 1 (AKT1), phosphatase and tensin homolog (PTEN), mechanistic target of rapamycin kinase (MTOR), S6 kinase, S6 ribosomal proteins, MAP kinases such as mitogen-activated protein kinase kinase 1 (MAP2K1), and extracellular signal-regulated kinases (ERKs). Suitable IGF1R pathway inhibitors include, but are not limited to, tyrosine kinase inhibitors such as OSI-906 (OSI; also known as Linsitinib and cis-3-[8-amino-1-(2-phenyl-7-quinolinyl)imidazo[1,5-a]pyrazin-3-yl]-1-methylcyclobutanol)), BMS-754807 (BMS; also known as (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-Pyrrolidinecarboxamide), BVP 51004 (Biovitrum), XL228 (Exelixis), INSM-18 NDGA (Insmed); anti-IGF1R monoclonal antibodies such as figitumumab (CP-751871), ganitumab (AMG 479), dalotuzumab (MK-0646), cixutumumab (IMC-A12), R1507, SCH 717454 (19D12), AVE1642 (EM164), BIIB022; IGF1/2 ligand inhibitors such as MEDI-573 and Xentuzumab (BI 836845); PI3K inhibitors such as BEZ235 (BEZ; also known as dactolisib, NVP-BEZ235, and 4-[2,3-dihydro-3-methyl-2-oxo-8-(3-quinolinyl)-1H-imidazo[4,5-c]quinolin-1-yl]-α,α-dimethyl-benzeneacetonitrile); other IGF1R pathway inhibitors such as Picropodophyllin (PPP); and combinations thereof. In some embodiments, the IGF1R pathway inhibitor comprises OSI-906, BMS-754807, BEZ235, or a combination thereof.

In one aspect, it is understood and herein contemplated that the disclosed methods of increasing the sensitivity of a cancer to IGF1R pathway inhibition and methods of treating a cancer comprising administering to a subject with a cancer an IGF1R pathway inhibitor and an E-cadherin inhibitor relate in part to the level of E-cadherin present in the sample prior to treatment and, in some circumstances, detection of the E-cadherin levels during and following treatment. Accordingly, disclosed herein are methods of increasing the sensitivity of a cancer to IGF1R pathway inhibition and methods of treating a cancer (such as, for example, an ER+ breast cancer or gastrointestinal cancer) comprising obtaining a cancerous tissue sample (such as, for example, a breast cancer tissue sample or gastrointestinal cancer tissue sample) from the subject; measuring the level of E-cadherin in the sample. In some aspect, the method can further comprise obtaining tissue sample and measuring the level of E-cadherin in the sample at multiple time points including prior to, during, and after treatment.

It is further understood and herein contemplated that treatment of a cancer with already depressed E-cadherin levels with an E-cadherin inhibitor and an IGF1R pathway inhibitor would unlikely be anymore effective than treating with an IGF1R alone. Similarly, elevated levels of E-cadherin would indicate that an IGF1R pathway inhibitor cancer treatment would benefit from the further administration of an E-cadherin inhibitor. Thus, in one aspect, disclosed herein are methods of treating a cancer (such as, for example, an ER+ breast cancer or gastrointestinal cancer) comprising administering to a subject an IGF1R pathway inhibitor and an E-cadherin inhibitor; wherein the subject does not have reduced levels of E-cadherin relative to a control. Accordingly, knowing the level of E-cadherin in the sample can be used to detect whether a cancer would be not only sensitive to IGF1R pathway inhibition, but also whether the IGF1R pathway inhibitor treatment regimen should be supplemented with an E-cadherin receptor. In one aspect, disclosed herein are methods of increasing the sensitivity of a cancer to IGF1R pathway inhibition and methods of treating a cancer (such as, for example, an ER+ breast cancer or gastrointestinal cancer) comprising obtaining a cancerous tissue sample (such as, for example, a breast cancer tissue sample or gastrointestinal cancer tissue sample) from the subject; and measuring the level of E-cadherin in the sample; wherein E-cadherin inhibitor is administered to a subject when E-cadherin levels are not reduced or increased relative to a control and not administering an E-cadherin inhibitor (for example, where a sample of the cancer comprises a level of E-cadherin which is reduced by no more than 25%, 20%, 15%, 10%, 8%, or 5% compared to a control or is reduced by a statistically insignificant amount compared to a control, is not reduced compared to a control) and/or administering an endocrine therapeutic when E-cadherin levels are reduced relative to a control (for example, the E-cadherin levels in the sample are at least 50%, at least 60%, at least 70%, at least 80%, at least 90%, at least 95%, at least 98%, or at least 99% reduced compared to a control).

The methods of treating a cancer comprising administering an IFG1R pathway inhibitor in combination with a endocrine therapeutic, methods of treating a cancer comprising administering an IFG1R pathway inhibitor in combination with an E-cadherin inhibitor, methods of determining the sensitivity of a cancer to IGF1R pathway inhibition, and/or increasing the sensitivity of a cancer to IFG1R pathway inhibition disclosed herein each are useful for the treatment of a wide array of cancer types in part because E-cadherin is expressed in a number of cell types and cancer types. Non-limiting examples of cancers that can be treated with these methods include Acute granulocytic leukemia, Acute lymphocytic leukemia, Acute myelogenous leukemia (AML), Adenocarcinoma, Adenosarcoma, Adrenal cancer, Adrenocortical carcinoma, Anal cancer, Anaplastic astrocytoma, Angiosarcoma, Appendix cancer, Astrocytoma, Basal cell carcinoma, B-Cell lymphoma, Bile duct cancer, Bladder cancer, Bone cancer Bone marrow cancer, Bowel cancer, Brain cancer, Brain stem glioma, Brain tumor, Breast cancer, Carcinoid tumors, Cervical cancer, Cholangiocarcinoma, Chondrosarcoma, Chronic lymphocytic leukemia (CLL), Chronic myelogenous leukemia (CML), Colon cancer, Colorectal cancer, Craniopharyngioma, Cutaneous lymphoma, Cutaneous melanoma, Diffuse astrocytoma, Ductal carcinoma in situ (DCIS), Endometrial cancer, Ependymoma, Epithelioid sarcoma, Esophageal cancer, Ewing sarcoma, Extrahepatic bile duct cancer, Eye cancer, Fallopian tube cancer, Fibrosarcoma, Gallbladder cancer, Gastric cancer, Gastrointestinal cancer, Gastrointestinal carcinoid cancer, Gastrointestinal stromal tumors (GIST), Germ cell tumor, Gestational Trophoblastic Disease (GTD), Glioblastoma multiforme (GBM), Glioma, Hairy cell leukemia, Head and neck cancer, Hemangioendothelioma, Hodgkin's lymphoma, Hypopharyngeal cancer, Infiltrating ductal carcinoma (IDC), Infiltrating lobular carcinoma (ILC), Inflammatory breast cancer (IBC), Intestinal Cancer, Intrahepatic bile duct cancer, Invasive/infiltrating breast cancer, Islet cell cancer, Jaw/oral cancer, Kaposi sarcoma, Kidney cancer, Laryngeal cancer, Leiomyosarcoma, Leptomeningeal metastases, Leukemia, Lip cancer, Liposarcoma, Liver cancer, Lobular carcinoma in situ, Low-grade astrocytoma, Lung cancer, Lymph node cancer, Lymphoma, Male breast cancer, Medullary carcinoma, Medulloblastoma, Melanoma, Meningioma, Merkel cell carcinoma, Mesenchymal chondrosarcoma, Mesenchymous, Mesothelioma, Metastatic breast cancer, Metastatic melanoma, Metastatic squamous neck cancer, Mixed gliomas, Mouth cancer, Mucinous carcinoma, Mucosal melanoma, Multiple myeloma, Mycosis Fungoides, Myelodysplastic Syndrome, Nasal cavity cancer, Nasopharyngeal cancer, Neck cancer, Neuroblastoma, Neuroendocrine tumors (NETs), Non-Hodgkin's lymphoma, Non-small cell lung cancer (NSCLC), Oat cell cancer, Ocular cancer, Ocular melanoma, Oligodendroglioma, Oral cancer, Oral cavity cancer, Oropharyngeal cancer, Osteogenic sarcoma, Osteosarcoma, Ovarian cancer, Ovarian epithelial cancer, Ovarian germ cell tumor, Ovarian primary peritoneal carcinoma, Ovarian sex cord stromal tumor, Paget's disease, Pancreatic cancer, Papillary carcinoma, Paranasal sinus cancer, Parathyroid cancer, Pelvic cancer, Penile cancer, Peripheral nerve cancer, Peritoneal cancer, Pharyngeal cancer, Pheochromocytoma, Pilocytic astrocytoma, Pineal region tumor, Pineoblastoma, Pituitary gland cancer, Primary central nervous system (CNS) lymphoma, Prostate cancer, Rectal cancer, Renal cell carcinoma, Renal pelvis cancer, Rhabdomyosarcoma, Salivary gland cancer, Sarcoma, Sinus cancer, Skin cancer, Small cell lung cancer (SCLC), Small intestine cancer, Soft tissue sarcoma, Spinal cancer, Spinal column cancer, Spinal cord cancer, Spinal tumor, Squamous cell carcinoma, Stomach cancer, Synovial sarcoma, T-cell lymphoma, Testicular cancer, Throat cancer, Thymoma/thymic carcinoma, Thyroid cancer, Tongue cancer, Tonsil cancer, Transitional cell cancer, Transitional cell cancer, Triple-negative breast cancer, Tubal cancer, Tubular carcinoma, Ureteral cancer, Urethral cancer, Uterine adenocarcinoma, Uterine cancer, Uterine sarcoma, Vaginal cancer, Vulvar cancer, Wilms tumor, Waldenstrom macroglobulinemia, etc., and combinations thereof.

In one aspect, it is understood and herein contemplated that the disclosed methods are particularly useful in treating ER+ breast cancers. As used herein, "ER+ breast cancer" refers to a breast cancer in which at least the majority of the cancerous cells express Estrogen Receptor (ER) protein. Any ER+ breast cancer can have a reduced level of E-cadherin. Accordingly, the present invention encompasses treatment of all ER+ breast cancers having a reduced level of E-cadherin. However, particular ER+ breast cancers can, in some embodiments, be selected based on known E-cadherin genotypes and/or phenotypes. The vast majority of invasive lobular breast cancers (ILC) have reduced levels of E-cadherin and thus, in some embodiments, the ER+ breast cancer can comprise an ILC. In other embodiments, the ER+ breast cancer is an invasive ductal breast carcinoma (IDC) having reduced E-cadherin, in some instances the IDC tumors having undergone epithelial to mesenchymal transition (EMT). In some embodiments, the ER+ breast cancer can comprise ductal carcinoma in situ (DCIS), inflammatory breast cancer, lobular carcinoma in situ (LCIS), Paget's disease of the nipple, Phyllodes tumor of the breast, angiosarcoma, and/or triple negative breast cancer (TBC), among others.

The sample of the breast cancer can be obtained from the subject or from a biological sample of the subject, and is generally handled, transported, stored, and analyzed under conditions which avoid contaminating or otherwise compromising the integrity of the sample. As used herein, the terms "sample of the cancer," "sample of the breast cancer," and "sample" when used in reference to the foregoing, refer to biological material obtained from a subject, or from a biological sample of a subject, in which the subject is suspected of having cancer or known to have cancer. The sample should contain cells suspected or known to be cancerous, or should contain biological material (e.g., extracted polynucleotides or polypeptides) from such cells. The sample can be obtained by any suitable method for further analysis (e.g., measuring E-cadherin levels). For example, the sample can be obtained by tissue scraping, biopsy (e.g., surgical biopsy, fine-needle aspiration biopsy, core needle biopsy, stereotactic biopsy, etc.), phlebotomy techniques, or other suitable methods.

The amount of active agent (e.g., IGF1R pathway inhibitor, endocrine therapeutic, or E-cadherin inhibitor) administered to the subject can vary widely but should be sufficient to therapeutically treat a cancer (such as, for example, an ER+ breast cancer or gastrointestinal cancer). The amount of active agent administered to the subject can be expressed in terms of a dosage amount per body weight. The amount of the disclosed active agent administered will vary from subject to subject, depending on the nature of the disclosed compositions and/or formulations, the species, gender, age, weight and general condition of the subject, the mode of administration, and the like. Effective dosages and schedules for administering the compositions may be determined empirically, and making such determinations is within the skill in the art. The dosage ranges for the administration of the disclosed compositions are those large enough to produce the desired effect (e.g., to reduce tumor growth). The dosage should not be so large as to outweigh benefits by causing adverse side effects, such as unwanted cross-reactions, anaphylactic reactions, and the like. The dosage can be adjusted by the individual clinician in the event of any counterindications. Generally, the disclosed compositions and/or formulations are administered to the subject at a dosage of active agent(s) ranging from 0.1 µg/kg body weight to 100 g/kg body weight. In some embodiments, the disclosed compositions and/or formulations are administered to the subject at a dosage of active agent(s) ranging from 1 µg/kg to 10 g/kg, from 10 µg/kg to 1 g/kg, from 10 µg/kg to 500 mg/kg, from 10 µg/kg to 100 mg/kg, from 10 µg/kg to 10 mg/kg, from 10 µg/kg to 1 mg/kg, from 10 µg/kg to 500 µg/kg, or from 10 µg/kg to 100 µg/kg body weight. Dosages above or below the range cited above may be administered to the individual subject if desired.

The methods can comprise one or more dosages of an agent (e.g., IGF1R pathway inhibitor, endocrine therapeutic, or E-cadherin inhibitor), for example, at least one, at least two, at least three, at least four, at least five, at least six, at least seven, at least eight, at least nine, or at least ten dosages. Administration of the dosages can be performed before the subject exhibits symptoms of a disease or disorder (e.g., prophylactically), or during or after symptoms of a disease occur.

The combination of IGF1R pathway inhibitor and the endocrine therapeutic or the combination IGF1R pathway inhibitor and E-cadherin inhibitor can be administered at the same time (e.g., in a same formulation or as separate formulations administered simultaneously) or at similar or overlapping times (e.g., administration of one immediately after or soon after administration of the other). Increasing the amount of time the IGF1R pathway inhibitor and the endocrine therapeutic are biodistributed together within the subject at therapeutic levels can increase the duration in which synergistic effects are observed. However, it is expressly not required that the combination of an IGF1R pathway inhibitor and the endocrine therapeutic or the combination of an IGF1R pathway inhibitor and an E-cadherin inhibitor be administered at the same (for example in a singular formulation) or similar time. In some embodiments, the IGF1R pathway inhibitor and the endocrine therapeutic can be separately administered at different times. In some embodiments, the IGF1R pathway inhibitor can be administered within one hour, six hours, or twelve hours of administering the endocrine therapeutic or E-cadherin inhibitor. In some embodiments, the IGF1R pathway inhibitor can be administered within one day, two days, three days, or five days or longer of administering the endocrine therapeutic or E-cadherin inhibitor.

In some embodiments, a subsequent administration of a dose is provided at least one day after a prior administration of a dose, or at least two days, at least three days, at least four days, at least five days, or at least six days after a prior administration of a dose. In some embodiments, a subsequent administration is provided at least one week after a prior administration, or at least two weeks, at least three weeks, or at least four weeks after a prior administration of a dose. In some embodiments, a subsequent administration is provided at least one month, at least two months, or at least three months after a prior administration.

The methods can be performed with or without administration of additional agents (e.g., therapeutic agents, diagnostic agents). In some embodiments, the methods can include administering one or more additional anti-cancer therapeutics in addition to administering the disclosed compositions or agents. It is understood that the methods can encompass any known anti-cancer therapeutic, the specific class of which are not particularly limited. Non-limiting examples of suitable anti-cancer therapeutics which can be used in the methods include Abemaciclib, Abiraterone Acetate, Abitrexate (Methotrexate), Abraxane (Paclitaxel Albumin-stabilized Nanoparticle Formulation), ABVD, ABVE, ABVE-PC, AC, AC-T, Adcetris (Brentuximab Vedotin), ADE, Ado-Trastuzumab Emtansine, Adriamycin (Doxorubicin Hydrochloride) and other DNA intercalators, Afatinib Dimaleate, Afinitor (Everolimus), Akynzeo (Netupitant and Palonosetron Hydrochloride), Aldara (Imiquimod), Aldesleukin, Alecensa (Alectinib), Alectinib, Alemtuzumab, Alimta (Pemetrexed Disodium), altretamine, Aliqopa (Copanlisib Hydrochloride), Alkeran for Injection (Melphalan Hydrochloride), Alkeran Tablets (Melphalan), Aloxi (Palonosetron Hydrochloride), Alunbrig (Brigatinib), Ambochlorin (Chlorambucil), Amboclorin Chlorambucil), Amifostine, Aminolevulinic Acid, Anastrozole, antiangiogenic agents such as angiostatin, antiestrogens such as tamoxifen, Aprepitant, Aredia (Pamidronate Disodium), Arimidex (Anastrozole), Aromasin (Exemestane), Arranon (Nelarabine), Arsenic Trioxide, Arzerra (Ofatumumab), Asparaginase *Erwinia chrysanthemi*, Atezolizumab, Avastin (Bevacizumab), Avelumab, Axitinib, Azacitidine, Bavencio (Avelumab), BEACOPP, Becenum (Carmustine), Beleodaq (Belinostat), Belinostat, Bendamustine Hydrochloride, BEP, Besponsa (Inotuzumab Ozogamicin), Bevacizumab, Bexarotene, Bexxar (Tositumomab and Iodine I 131 Tositumomab), Bicalutamide, BiCNU (Carmustine), Bleomycin, Blinatumomab, Blincyto (Blinatumomab), Bortezomib, Bosulif (Bosutinib), Bosutinib, Brentuximab Vedotin, Brigatinib, BuMel, Busulfan, Busulfex (Busulfan), Cabazitaxel, Cabometyx (Cabozantinib-S-Malate), Cabozantinib-S-Malate, CAF, Campath (Alemtuzumab), Camptosar, (Irinotecan Hydrochloride), Capecitabine, CAPDX, Carac (Fluorouracil-Topical) and other antimetabolites, Carboplatin, CARBOPLATIN-TAXOL, Carfilzomib, Carmubris (Carmustine), Carmustine, Carmustine Implant, Casodex (Bicalutamide), CEM, Ceritinib, Cerubidine (Daunorubicin Hydrochloride), Cervarix (Recombinant HPV Bivalent Vaccine), Cetuximab, CEV, Chlorambucil, CHLORAMBUCIL-PREDNISONE, CHOP, Cisplatin, Cladribine, Clafen (Cyclophosphamide), Clofarabine, Clofarex (Clofarabine), Clolar (Clofarabine), CMF, Cobimetinib, Cometriq (Cabozantinib-S-Malate), Copanlisib Hydrochloride, COPDAC, COPP, COPP-ABV, Cosmegen (Dactinomycin), Cotellic (Cobimetinib), Crizotinib, CVP, Cyclophosphamide, Cyfos (Ifosfamide), Cyramza (Ramucirumab), Cytarabine, Cytarabine Liposome, Cytosar-U (Cytarabine), Cytoxan (Cyclophosphamide), Dabrafenib, Dacarbazine, Dacogen (Decitabine), Dactinomycin, Daratumumab, Darzalex (Daratumumab), Dasatinib, Daunorubicin Hydrochloride, Daunorubicin Hydrochloride and Cytarabine Liposome, Decitabine, Defibrotide Sodium, Defitelio (Defibrotide Sodium), Degarelix, Denileukin Diftitox, Denosumab, DepoCyt (Cytarabine Liposome), Dexamethasone, Dexrazoxane Hydrochloride, Dinutuximab, Docetaxel, Doxil (Doxorubicin Hydrochloride Liposome), Doxorubicin Hydrochloride, Doxorubicin Hydrochloride Liposome, Dox-SL (Doxorubicin Hydrochloride Liposome), DTIC-Dome (Dacarbazine), Durvalumab, Efudex (Fluorouracil-Topical), Elitek (Rasburicase), Ellence (Epirubicin Hydrochloride), Elotuzumab, Eloxatin (Oxaliplatin), Eltrombopag Olamine, Emend (Aprepitant), Empliciti (Elotuzumab), Enasidenib Mesylate, Enzalutamide, Epirubicin Hydrochloride, EPOCH, Erbitux (Cetuximab), Eribulin Mesylate, Erivedge (Vismodegib), Erlotinib Hydrochloride, Erwinaze (Asparaginase *Erwinia chrysanthemi*), Ethyol (Amifostine), Etopophos (Etoposide Phosphate), Etoposide and other topoisomerase inhibitors (e.g., camptothecin), Etoposide Phosphate, Evacet (Doxorubicin Hydrochloride Liposome), Everolimus, Evista, (Raloxifene Hydrochloride), Evomela (Melphalan Hydrochloride), Exemestane, 5-FU (Fluorouracil Injection), 5-FU (Fluorouracil-Topical), Fareston (Toremifene), Farydak (Panobinostat), Faslodex (Fulvestrant), FEC, Femara (Letrozole), Filgrastim, Fludara (Fludarabine Phosphate), Fludarabine Phosphate, Fluoroplex (Fluorouracil-Topical), Fluorouracil Injection, Fluorouracil-Topical, Flutamide, Folex (Methotrexate), Folex PFS (Methotrexate), FOLFIRI, FOLFIRI-BEVACIZUMAB, FOLFIRI-CETUXIMAB, FOLFIRINOX, FOLFOX, Folotyn (Pralatrexate), FU-LV, Fulvestrant, Gardasil (Recombinant HPV Quadrivalent Vaccine), Gardasil 9 (Recombinant HPV Nonavalent Vaccine), Gazyva (Obinutuzumab), Gefitinib, Gemcitabine Hydrochloride, GEMCITABINE-CISPLATIN, GEMCITABINE-OXALIPLATIN, Gemtuzumab Ozogamicin, Gemzar (Gemcitabine Hydrochloride), Gilotrif (Afatinib Dimaleate), Gleevec (Imatinib Mesylate), Gliadel (Carmustine Implant), Gliadel wafer (Carmustine Implant), Glucarpidase, Goserelin Acetate, Halaven (Eribulin Mesylate), Hemangeol (Propranolol Hydrochloride), Herceptin (Trastuzumab), HPV Bivalent Vaccine, Recombinant, HPV Nonavalent Vaccine, Recombinant, HPV Quadrivalent Vaccine, Recombinant, Hycamtin (Topotecan Hydrochloride), Hydrea (Hydroxyurea), Hydroxyurea, Hyper-CVAD, Ibrance (Palbociclib), Ibritumomab Tiuxetan, Ibrutinib, ICE, Iclusig (Ponatinib Hydrochloride), Idamycin (Idarubicin Hydrochloride), Idarubicin Hydrochloride, Idelalisib, Idhifa (Enasidenib Mesylate), Ifex (Ifosfamide), Ifosfamide and other alkylating agents, Ifosfamidum (Ifosfamide), IL-2 (Aldesleukin), Imatinib Mesylate, Imbruvica (Ibrutinib), Imfinzi (Durvalumab), Imiquimod, Imlygic (Talimogene Laherparepvec), Inlyta (Axitinib), Inotuzumab Ozogamicin, Interferon Alfa-2b, Recombinant, Interleukin-2 (Aldesleukin), Intron A (Recombinant Interferon Alfa-2b), Iodine I 131 Tositumomab and Tositumomab, Ipilimumab, Iressa (Gefitinib), Irinotecan Hydrochloride, Irinotecan Hydrochloride Liposome, Istodax (Romidepsin), Ixabepilone, Ixazomib Citrate, Ixempra (Ixabepilone), Jakafi (Ruxolitinib Phosphate), JEB, Jevtana (Cabazitaxel), Kadcyla (Ado-Trastuzumab Emtansine), Keoxifene (Raloxifene Hydrochloride), Kepivance (Palifermin), Keytruda (Pembrolizumab), Kisqali (Ribociclib), Kymriah (Tisagenlecleucel), Kyprolis (Carfilzomib), Lanreotide Acetate, Lapatinib Ditosylate, Lartruvo (Olaratumab), Lenalidomide, Lenvatinib Mesylate, Lenvima (Lenvatinib Mesylate), Letrozole, Leucovorin Calcium, Leukeran (Chlorambucil), Leuprolide Acetate, Leustatin (Cladribine), Levulan (Aminolevulinic Acid), Linfolizin (Chlorambucil), LipoDox (Doxorubicin Hydrochloride Liposome), Lomustine, Lonsurf (Trifluridine and Tipiracil Hydrochloride), Lupron (Leuprolide Acetate), Lupron Depot (Leuprolide Acetate), Lupron Depot-Ped (Leuprolide Acetate), Lynparza (Olaparib), Marqibo (Vincristine Sulfate Liposome), Matulane (Procarbazine Hydrochloride), Mechlorethamine Hydrochloride, Megestrol Acetate, Mekinist (Trametinib), Melphalan, Melphalan Hydrochloride, Mercaptopurine, Mesna, Mesnex (Mesna), Methazolastone (Temozolomide), Methotrexate, Methotrexate LPF (Methotrexate), Methylnaltrexone Bromide, Mexate (Methotrexate), Mexate-AQ (Methotrexate), Midostaurin, Mitomycin C, Mitoxantrone Hydrochloride, Mitozytrex (Mitomycin C), MOPP, Mozobil (Plerixafor), Mustargen (Mechlorethamine Hydrochloride), Mutamycin (Mitomycin C), Myleran (Busulfan), Mylosar (Azacitidine), Mylotarg (Gemtuzumab Ozogamicin), Nanoparticle Paclitaxel (Paclitaxel Albumin-stabilized Nanoparticle Formulation), Navelbine (Vinorelbine Tartrate), Necitumumab, Nelarabine, Neosar (Cyclophosphamide), Neratinib Maleate, Nerlynx (Neratinib Maleate), Netupitant and Palonosetron Hydrochloride, Neulasta (Pegfilgrastim), Neupogen (Filgrastim), Nexavar (Sorafenib Tosylate), Nilandron (Nilutamide), Nilotinib, Nilutamide, Ninlaro (Ixazomib Citrate), Niraparib Tosylate Monohydrate, Nivolumab, Nolvadex (Tamoxifen Citrate), Nplate (Romiplostim), Obinutuzumab, Odomzo (Sonidegib), OEPA, Ofatumumab, OFF, Olaparib, Olaratumab, Omacetaxine Mepesuccinate, Oncaspar (Pegaspargase), Ondansetron Hydrochloride, Onivyde (Irinotecan Hydrochloride Liposome), Ontak (Denileukin Diftitox), Opdivo (Nivolumab), OPPA, Osimertinib, Oxaliplatin, Paclitaxel, Paclitaxel Albumin-stabilized Nanoparticle Formulation, PAD, Palbociclib, Palifermin, Palonosetron Hydrochloride, Palonosetron Hydrochloride and Netupitant, Pamidronate Disodium, Panitumumab, Panobinostat, Paraplat (Carboplatin), Paraplatin (Carboplatin), Pazopanib Hydrochloride, PCV, PEB, Pegaspargase, Pegfilgrastim, Peginterferon Alfa-2b, PEG-Intron (Peginterferon Alfa-2b), Pembrolizumab, Pemetrexed Disodium, Perjeta (Pertuzumab), Pertuzumab, Platinol (Cisplatin), Platinol-AQ (Cisplatin), Plerixafor, Pomalidomide, Pomalyst (Pomalidomide), Ponatinib Hydrochloride, Portrazza (Necitumumab), Pralatrexate, Prednisone, Procarbazine Hydrochloride, Proleukin (Aldesleukin), Prolia (Denosumab), Promacta (Eltrombopag Olamine), Propranolol Hydrochloride, Provenge (Sipuleucel-T), Purinethol (Mercaptopurine), Purixan (Mercaptopurine), Radium 223 Dichloride, Raloxifene Hydrochloride, Ramucirumab, Rasburicase, R—CHOP, R—CVP, Recombinant Human Papillomavirus (HPV) Bivalent Vaccine, Recombinant Human Papillomavirus (HPV) Nonavalent Vaccine, Recombinant Human Papillomavirus (HPV) Quadrivalent Vaccine, Recombinant Interferon Alfa-2b, Regorafenib, Relistor (Methylnaltrexone Bromide), R-EPOCH, Revlimid (Lenalidomide), Rheumatrex (Methotrexate), Ribociclib, R-ICE, Rituxan (Rituximab), Rituxan Hycela (Rituximab and Hyaluronidase Human), Rituximab, Rituximab and, Hyaluronidase Human, Rolapitant Hydrochloride, Romidepsin, Romiplostim, Rubidomycin (Daunorubicin Hydrochloride), Rubraca (Rucaparib Camsylate), Rucaparib Camsylate, Ruxolitinib Phosphate, Rydapt (Midostaurin), Sclerosol Intrapleural Aerosol (Talc), Siltuximab, Sipuleucel-T, Somatuline Depot (Lanreotide Acetate), Sonidegib, Sorafenib Tosylate, Sprycel (Dasatinib), STANFORD V, Sterile Talc Powder (Talc), Steritalc (Talc), Stivarga (Regorafenib), Sunitinib Malate, Sutent (Sunitinib Malate), Sylatron (Peginterferon Alfa-2b), Sylvant (Siltuximab), Synribo (Omacetaxine Mepesuccinate), Tabloid (Thioguanine), TAC, Tafinlar (Dabrafenib), Tagrisso (Osimertinib), Talc, Talimogene Laherparepvec, Tamoxifen Citrate, Tarabine PFS (Cytarabine), Tarceva (Erlotinib Hydrochloride), Targretin (Bexarotene), Tasigna (Nilotinib), Taxol (Paclitaxel) and other mitotic inhibitors, Taxotere (Docetaxel), Tecentriq, (Atezolizumab), Temodar (Temozolomide), Temozolomide, Temsirolimus, Thalidomide, Thalomid (Thalidomide), Thioguanine, Thiotepa, Tisagenlecleucel, Tolak (Fluorouracil-Topical), Topotecan Hydrochloride, Toremifene, Torisel (Temsirolimus), Tositumomab and Iodine I 131 Tositumomab, Totect (Dexrazoxane Hydrochloride), TPF, Trabectedin, Trametinib, Trastuzumab, Treanda (Bendamustine Hydrochloride), Trifluridine and Tipiracil Hydrochloride, Trisenox (Arsenic Trioxide), Tykerb (Lapatinib Ditosylate), Unituxin (Dinutuximab), Uridine Triacetate, VAC, Vandetanib, VAMP, Varubi (Rolapitant Hydrochloride), Vectibix (Panitumumab), VeIP, Velban (Vinblastine Sulfate), Velcade (Bortezomib), Velsar (Vinblastine Sulfate), Vemurafenib, Venclexta (Venetoclax), Venetoclax, Verzenio (Abemaciclib), Viadur (Leuprolide Acetate), Vidaza (Azacitidine), Vinblastine Sulfate, Vincasar PFS (Vincristine Sulfate), Vincristine Sulfate, Vincristine Sulfate Liposome, Vinorelbine Tartrate, VIP, Vismodegib, Vistogard (Uridine Triacetate), Voraxaze (Glucarpidase), Vorinostat, Votrient (Pazopanib Hydrochloride), Vyxeos (Daunorubicin Hydrochloride and Cytarabine Liposome), Wellcovorin (Leucovorin Calcium), Xalkori (Crizotinib), Xeloda (Capecitabine), XELIRI, XELOX, Xgeva (Denosumab), Xofigo (Radium 223 Dichloride), Xtandi (Enzalutamide), Yervoy (Ipilimumab), Yondelis (Trabectedin), Zaltrap (Ziv-Aflibercept), Zarxio (Filgrastim), Zejula (Niraparib Tosylate Monohydrate), Zelboraf (Vemurafenib), Zevalin (Ibritumomab Tiuxetan), Zinecard (Dexrazoxane Hydrochloride), Ziv-Aflibercept, Zofran (Ondansetron Hydrochloride), Zoladex (Goserelin Acetate), Zoledronic Acid, Zolinza (Vorinostat), Zometa (Zoledronic Acid), Zydelig (Idelalisib), Zykadia (Ceritinib), and/or Zytiga (Abiraterone Acetate), busulphan, calcium folinate, vindesine, crisantaspase, gefitinib (IRESSA), hydroxyurea, pentostatin, raltitrexed, streptozocin, tegafururacil, tioguanine/thioguanine, treosulfan, vinorelbine, and combinations thereof. Also contemplated herein are chemotherapeutics that are PD1/PDL1 blockade inhibitors (such as, for example, lambrolizumab, nivolumab, pembrolizumab, pidilizumab, BMS-936559, Atezolizumab, Durvalumab, or Avelumab).

As noted throughout the specification, the level of E-cadherin is predictive of the responsiveness (i.e., the sensitivity) a cancer has or will have to IFG1R pathway inhibition therapy. Accordingly, disclosed herein are methods to predict the likelihood a subject with a cancer (such as, for example a breast cancer or gastrointestinal cancer) will respond therapeutically to a treatment comprising administering an IGF1R pathway inhibitor, the method comprising obtaining a sample of the breast cancer from the subject; and determining a level of E-cadherin in the sample; wherein a reduced level of E-cadherin compared to a control indicates the subject will respond therapeutically to the treatment; and wherein a level of E-cadherin which is not reduced compared to the control indicates the subject will not respond therapeutically to the treatment. Stated, slightly differently, disclosed herein are methods of detecting sensitivity of a cancer to IGF1R pathway inhibition in a subject comprising obtaining a cancerous tissue sample; and assaying the level of E-cadherin in the tissue sample relative to a control; wherein a decrease in the level of E-cadherin indicates that the cancer is sensitive to IGF1R inhibition.

The treatment comprises administering an IGF1R pathway inhibitor, which includes any herein disclosed IGF1R pathway inhibitor. In some embodiments, the treatment can further comprise any herein disclosed endocrine therapeutic, additional anti-cancer therapeutic, or combinations thereof, according to any of the disclosed dosage amounts, number of dosages, and timing of dosages. In some embodiments in which the breast cancer comprises an estrogen receptor-positive (ER+) breast cancer, the treatment can further comprise administering an endocrine therapeutic.

The determined E-cadherin levels are compared to a control. In some embodiments, the E-cadherin levels in the sample are at least 50% reduced compared to a control, thereby indicating the subject will respond therapeutically to the treatment. In some embodiments, the E-cadherin levels in the sample are at least 60%, at least 70%, at least 80%, at least 90%, at least 95%, at least 98%, or at least 99% reduced compared to a control, thereby indicating the subject will respond therapeutically to the treatment.

The determined level of E-cadherin can be reduced compared to the control, thereby indicating the subject will respond therapeutically to the treatment. In some such embodiments, the methods can further comprise advising the subject of the increased likelihood the subject will respond therapeutically to the treatment. In some or further embodiments, the methods can further comprise administering the treatment to the subject.

Alternatively, the level of E-cadherin can be determined to be not reduced compared to the control, thereby indicating the subject will not respond therapeutically to the treatment. In some such embodiments, the methods can further comprise advising the subject of the increased likelihood the subject will not respond therapeutically to the treatment. In some or further embodiments, the methods can further comprise withholding the treatment from the subject, and/or administering an alternative treatment.

As part of any of the methods disclosed herein, the E-cadherin levels in both the sample and the control can be determined via a wide array of methods used to determine polynucleotide or polypeptide levels. As used herein, the "level" of a polynucleotide or polypeptide can refer to an expression level, a functionality level, or combinations thereof. The sample or a portion thereof may be further processed according to standard protocols used for the method selected to determine the polynucleotide or polypeptide levels. For example, an E-cadherin level can be determined as a level of E-cadherin polypeptide expression, which refers to a qualitative or quantitative amount of polypeptide within the sample or control, for example, within the cells of the sample or control. Polypeptide expression levels can be determined by a number of methods, including radiation absorbance (e.g., ultraviolet light absorption at 260, 280, or 230 nm), bicinchoninic acid (BCA) assay, Bradford assay, biuret test, Lowry method, Coomassie-blue staining, silver-staining, immunodetection and/or Western blot analysis, and other suitable methods.

Optionally, an E-cadherin level can be determined as a level of E-cadherin polynucleotide expression, which refers to a qualitative or quantitative amount of RNA polynucleotide within the sample or control, for example, within the cells of the sample or control. Polynucleotide expression levels such as mRNA transcript levels can be determined by a number of methods, including radiation absorbance (e.g., ultraviolet light absorption at 260, 280, or 230 nm), quantification of fluorescent dye or tag emission (e.g., ethidium bromide intercalation), quantitative polymerase chain reaction (qPCR) of cDNA produced from mRNA transcripts, southern blot analysis, gene expression microarray, or other suitable methods. Levels of mRNA transcripts can also be used to infer or estimate levels of polypeptide expression.

Optionally, an E-cadherin level can be determined as a level of E-cadherin polypeptide functionality, which refers to a qualitative or quantitative measurement of E-cadherin polypeptide's performance of any one or more functions known to be associated with E-cadherin polypeptide. Alternatively, or in addition to, the term "E-cadherin polypeptide functionality" can also refer to a qualitative or quantitative measurement of E-cadherin polypeptide's physical state (e.g., polypeptide folding, accessibility, or mutation) known to affect E-cadherin polypeptide's performance of any one or more functions known to be associated with E-cadherin polypeptide. Thus, while a polypeptide expression level may or may not be altered compared to a control, the function of the polypeptide can be reduced compared to a control. E-cadherin polypeptide functionality can be determined by, for example and without limitation, secondary and/or tertiary folding analysis (e.g., incomplete or incorrect protein folding determinable by circular dichroism, crystallography, nuclear magnetic resonance, electron microscopy, protein folding prediction programs, or other methods), sequestration experiments (e.g., coimmunoprecipitation with a repressor or inhibitor) compartmentalization experiments (e.g., microscopy observed cellular localization), functional and/or enzymatic assay (e.g., DNA-binding assay, IGF1R binding assay), presence of amino acid sequence mutations known to reduce function, or other suitable methods.

Optionally, an E-cadherin level can be determined as a level of E-cadherin polynucleotide functionality, which refers to a qualitative or quantitative measurement of E-cadherin polynucleotide's performance of any one or more functions known to be associated with E-cadherin polynucleotide. Alternatively or in addition to, the term "E-cadherin polynucleotide functionality" can also refer to a qualitative or quantitative measurement of E-cadherin polynucleotide's physical state (e.g., polynucleotide folding, accessibility, or mutation) known to affect E-cadherin polynucleotide's performance of any one or more functions known to be associated with E-cadherin polynucleotide, or the downstream E-cadherin polypeptide's performance of any one or more functions known to be associated with E-cadherin polypeptide. Thus, while a polynucleotide expression level may or may not be altered compared to a control, the function of the polynucleotide can be reduced compared to a control. E-cadherin polynucleotide functionality can be determined by, for example and without limitation, mRNA folding analysis (e.g., inhibitory hairpin formation determinable by nucleotide accessibility experiments, mRNA folding prediction programs, or other methods), DNA modification experiments (e.g., DNA-transcription promoter/repressor binding assays, histone modification assays, methylation analysis) functional and/or enzymatic assay (e.g., mRNA translation assays), presence of nucleic acid sequence mutations known to reduce function, or other suitable methods.

The cancerous tissue sample, and control can comprise any biological sample. Biological samples include all clinical samples useful for detection of disease or infection in subjects. Appropriate samples include any conventional biological samples, including clinical samples obtained from a human or veterinary subject. Exemplary samples include, without limitation, cells, cell lysates, blood smears, cytocentrifuge preparations, cytology smears, bodily fluids (e.g., blood, plasma, serum, saliva, sputum, urine, bronchial alveolar lavage, semen, cerebrospinal fluid (CSF), etc.), tissue biopsies or autopsies, fine-needle aspirates, and/or tissue sections. For example, a tissue sample from a tumor in a subject's organ (e.g., liver) is taken by a surgeon. The tissue sample can be taken, for example, by performing a biopsy. An examination of the cells in this sample by a pathologist may not reveal in which of the subject's tissues or organs (e.g., lungs, kidneys, stomach, liver, brain, skin, testicle, thymus, thyroid, colon, pancreas, ovary, etc.) the cancer arises because the cells may appear immature and/or primitive and therefore difficult to identify. It should be understood that the tissue of origin is relevant to diagnosis, prognosis, and/or treatment.

It is understood and herein contemplated that the control can comprise any biological sample or alternatively, a collection of values used as a standard applied to one or more subjects (e.g., a general number or average that is known and not identified in the method using a sample). In some embodiments, the control can comprise a biological sample of the subject known not to be or suspected not to be cancerous (e.g., a baseline sample). In some embodiments, the control can comprise the subject's non-cancerous cells which are of the same cell type as cells of the sample of the breast cancer. In some embodiments, the control can comprise non-cancerous epithelial cells of the subject. In some embodiments, the control can comprise non-cancerous mammary epithelial cells of the subject. Typically, the level of E-cadherin is determined in a control comprising a biological sample without additional steps or manipulations performed on the control beyond those required to obtain the control and determine E-cadherin levels. However, storage steps (e.g., in cryogenic conditions), washing steps (e.g., in buffered solutions), and other steps not expected to significantly affect the results upon determining E-cadherin levels can be included for both the control and the sample.

As noted herein the disclosed methods of treating a cancer comprising administering an IFG1R pathway inhibitor in combination with a endocrine therapeutic, methods of treating a cancer comprising administering an IFG1R pathway inhibitor in combination with an E-cadherin inhibitor, and/or methods of increasing the sensitivity of a cancer to IFG1R pathway inhibition comprise in one instance the administration of an IGF1R pathway inhibitor (such as, for example, OSI-906 (OSI; also known as Linsitinib and cis-3-[8-amino-1-(2-phenyl-7-quinolinyl)imidazo[1,5-a]pyrazin-3-yl]-1-methyl-cyclobutanol)), BMS-754807 (BMS; also known as (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-Pyrrolidinecarboxamide), BVP 51004 (Biovitrum), XL228 (Exelixis), INSM-18 NDGA (Insmed); anti-IGF1R monoclonal antibodies such as figitumumab (CP-751871), ganitumab (AMG 479), dalotuzumab (MK-0646), cixutumumab (IMC-A12), R1507, SCH 717454 (19D12), AVE1642 (EM164), BIIB022; IGF1/2 ligand inhibitors such as MEDI-573 and Xentuzumab (BI 836845); PI3K inhibitors such as BEZ235 (BEZ; also known as dactolisib, NVP-BEZ235, and 4-[2,3-dihydro-3-methyl-2-oxo-8-(3-quinolinyl)-1H-imidazo[4,5-c]quinolin-1-yl]-α,α-dimethyl-benzeneacetonitrile Picropodophyllin (PPP); and combinations thereof) in combination with an endocrine therapeutic (such as, for example tamoxifen, ICI 182,780 (ICI; also known as fulvestrant (Faslodex) and 7α,17β-[9-[(4,4,5,5,5-Pentafluoropentyl)sulfinyl]nonyl]estra-1,3,5(10)-triene-3,17-diol), and aromatase inhibitors such as aminoglutethimide, testolactaone (Teslac), anastrozole (Arimidex), letrozole (Femara), exemestane (Aromasin), vorozole (Rivizor), formestane (Lentaron), fadrozole (Afema), 1,4,6-Androstatriene-3,17-dione (ATD), and 4-androstene-3,6,17-trione (4-AT; also known as 6-OXO), or combinations thereof) or an IGF1R pathway inhibitor (such as, for example, OSI-906 (OSI; also known as Linsitinib and cis-3-[8-amino-1-(2-phenyl-7-quinolinyl)imidazo[1,5-a]pyrazin-3-yl]-1-methyl-cyclobutanol)), BMS-754807 (BMS; also known as (2S)-1-[4-[(5-Cyclopropyl-1H-pyrazol-3-yl)amino]pyrrolo[2,1-f][1,2,4]triazin-2-yl]-N-(6-fluoro-3-pyridinyl)-2-methyl-2-Pyrrolidinecarboxamide), BVP 51004 (Biovitrum), XL228 (Exelixis), INSM-18 NDGA (Insmed); anti-IGF1R monoclonal antibodies such as figitumumab (CP-751871), ganitumab (AMG 479), dalotuzumab (MK-0646), cixutumumab (IMC-A12), R1507, SCH 717454 (19D12), AVE1642 (EM164), BIIB022; IGF1/2 ligand inhibitors such as MEDI-573 and Xentuzumab (BI 836845); PI3K inhibitors such as BEZ235 (BEZ; also known as dactolisib, NVP-BEZ235, and 4-[2,3-dihydro-3-methyl-2-oxo-8-(3-quinolinyl)-1H-imidazo[4,5-c]quinolin-1-yl]-α,α-dimethyl-benzeneacetonitrile Picropodophyllin (PPP); and combinations thereof) in combination with an E-cadherin inhibitor (such as, for example, a small interfering RNA (siRNA), short hairpin RNA (shRNA), micro RNA (mRNA), trans-acting small interfering RNA (tasiRNA), long non-coding RNA (lncRNA), Piwi-interacting RNA (piRNA) including, but not limited to SEQ ID NO: 5 and SEQ ID NO: 6). As noted above, while the IGF1R pathway inhibitor can be administered at a different timepoint than either the endocrine therapeutic or the E-cadherin inhibitor, it is also contemplated herein that the IGF1R pathway inhibitor can be administered concurrently or simultaneously with either the endocrine therapeutic or the E-cadherin inhibitor. Accordingly, in one aspect, contemplated herein are pharmaceutical compositions comprising either an IGF1R pathway inhibitor and an endocrine therapeutic or an IGF1R pathway inhibitor and an E-cadherin inhibitor. It is understood and herein contemplated that composition can comprise a therapeutically effective amount of the IGF1R pathway inhibitor and the endocrine therapeutic or a therapeutically effective amount of the IGF1R pathway inhibitor and the E-cadherin inhibitor. It is further understood and herein contemplated that due to the synergistic effect of the a therapeutically effective amount of the IGF1R pathway inhibitor in combination with the endocrine therapeutic or the IGF1R pathway inhibitor in combination with the E-cadherin inhibitor, the therapeutically effective amount of either active agent of the composition (i.e., the IGF1R pathway inhibitor, endocrine therapeutic, and/or E-cadherin inhibitor) can be less than the therapeutically effective amount of any of the active agents when administered individually. In one aspect, disclosed herein are methods of treating a cancer comprising administering an IFG1R pathway inhibitor in combination with a endocrine therapeutic, methods of treating a cancer comprising administering an IFG1R pathway inhibitor in combination with an E-cadherin inhibitor, and/or methods of increasing the sensitivity of a cancer to IFG1R pathway inhibition comprising administering to the subject a pharmaceutical composition comprising an IGF1R pathway inhibitor and an endocrine therapeutic or a pharmaceutical composition comprising an IGF1R pathway inhibitor and an E-cadherin inhibitor.

EXAMPLES

To further illustrate the principles of the present disclosure, the following examples are put forth so as to provide those of ordinary skill in the art with a complete disclosure and description of how the compositions, articles, and methods claimed herein are made and evaluated. They are intended to be purely exemplary of the invention and are not intended to limit the scope of what the inventors regard as their disclosure. These examples are not intended to exclude equivalents and variations of the present invention which are apparent to one skilled in the art. Unless indicated otherwise, temperature is ° C. or is at ambient temperature, and pressure is at or near atmospheric. There are numerous variations and combinations of process conditions that can be used to optimize product quality and performance. Only reasonable and routine experimentation will be required to optimize such process conditions.

Example 1

Materials and Methods
Cell Culture.
Cell lines were authenticated by the University of Arizona Genetics Core and *mycoplasma* tested (Lonza #LT07-418). Lab stocks were made following authentication and used for this study. MCF-7 (ATCC; DMEM+10% FBS [Jun. 29, 2016]), T47D (ATCC; RPMI+10% FBS [Feb. 8, 2017]), ZR75.1 (ATCC; RPMI+10% FBS [Oct. 13, 2016]), MDA-MB-231 (ATCC; DMEM+10% FBS [Oct. 13, 2016]), MDA-MB-134-IV (ATCC; 50/50 DMEM/L15+10% FBS [Feb. 8, 2017]), SUM44PE (Asterand; DMEM/F12+2% CSS with 5 ug/ml insulin, 1ug/ml hydrocortisone, 5 mM ethanolamine, 5 ug/ml transferrin, 10 nM triodothyronime, and 50 nM sodium selenite [Feb. 8, 2017—no reference profile exists in database]), and BCK4 (MEM+5% FBS with 1 nM insulin and 1×NEAA [Oct. 13, 2016—no reference profile exists in database) cells were cultured with indicated media conditions.
Transient siRNA Transfection.
Cells were reverse transfected with 25 nM final concentration of siGENOME human SMARTpool control siRNA (Dharmacon #D-001206) or siGENOME human SMARTpool CDH1 siRNA (Dharmacon #M-003877-02) using Lipofectamine RNAiMAX (Invitrogen #13778) protocol for 48 hours. For IGF1 (GroPep BioReagents #CU100) stimulation, cells were serum starved overnight and pulsed with IGF1 (1 nM, 10 nM, or 100 nM) for 10 minutes.
Stable shRNA Infection.
Stable CDH1 knockdown T47D cells were generated using a retro-viral infection of *Renilla* control (shSCR; SEQ ID NO: 4) and two anti-CDH1 (sh-1; SEQ ID NO: 5; and sh-2; SEQ ID NO: 6) short-hairpin RNAs (shRNA). Cells were selected with growth media supplemented with 1 µg/ml Puromycin (Life #A11138-03).
Plasmid DNA Overexpression.
MDA-MB-231 cells were stably transfected using FUGENE6 with empty or hE-cadherin-pcDNA3 vector (Addgene #45769) using 15 µg DNA per 10 cm plate of cells. Cells were selected in growth media supplemented with 800 µg/ml G418 (Invitrogen #10131-035).
Immunoblotting.
Samples for immunoblot analysis were collected using RIPA buffer (50 mM Tris pH 7.4, 150 mM NaCl, 1 mM EDTA, 0.5% Nonidet P-40, 0.5% NaDeoxycholate, 0.1% SDS, 1×HALT cocktail [Thermo Fisher #78442]) and standard immunoblot technique was followed. Membranes were blocked in Odyssey PBS Blocking Buffer (LiCor #927-40000), and incubated in primary antibodies overnight: pIGF1R Y1135 (Cell Signaling #3918; 1:500), IGF1R β-subunit (Cell Signaling #3027; 1:1000), pAkt 5473 (Cell Signaling #4060; 1:1000), total Akt (Cell Signaling #9272;

1:1000), E-cadherin (BD Biosciences #610182; 1:1000), and β-actin (Sigma #A5441; 1:5000). Membranes were incubated in LiCor secondary antibodies for 1 hour (anti-rabbit 800CW [LiCor #926-32211]; anti-mouse 680LT [LiCor #925-68020]; 1:10,000), and imaged with Odyssey Infrared Imager.

IGF1-Induced Cell Cycle and Viability Analysis.

For cell cycle: MCF-7 and ZR75.1 cells were reverse transfected as described above, serum starved for approx. 30 hours, and pulsed with 10 nM IGF1 for 17 hours. Cells were fixed in 70% EtOH for 30 minutes at 4° C. and RNA digested using 50 ng/µl RNase A (Qiagen #1007885) for 15 minutes at 37° C. DNA content was then stained using 50 ng/µl propidium iodide (Sigma #P4170) for 30 minutes at 4° C. Cell cycle profiles were analyzed using the BD LSRII flow cytometer and analyzed using the FACS DIVA software. The statistical difference in percent of cells in S- or G2/M phase in IGF1 treated cells over vehicle control in experimental groups was evaluated using a two-tailed student's t-test ($p<0.05$). For viability: T47D shSCR and shCDH1 #1 and #2 cells were plated in serum-free media in 96 well plates (9,000 cells/well) and then stimulated with IGF1 (10 nM) for 6 days. The FluoReporter Blue Fluorometric dsDNA Quantitation Kit was used to measure DNA content. Statistical difference in Hoechst fluorescence in IGF1 treated cells over vehicle control in each cell line was evaluated using a two-tailed student's t-test ($p<0.05$).

Immunofluorescence and Proximity Ligation Assay (PLA).

Cells were plated on coverslips and fixed in 4% paraformaldehyde for 30 minutes at 37° C. Coverslips were permeabilized for 1 hour using PBS+0.3% Triton X-100. For immunofluorescence, coverslips were blocked in PBS+5% goat serum, incubated in primary antibody overnight (total IGF1R β-subunit [Cell Signaling #3027; 1:300] and E-cadherin [BD Biosciences #610182; 1:100]), followed by Alexa Fluor secondary antibody incubation for 1 hour (anti-rabbit Alexa Fluor 488 [Life Technologies #A11070] and anti-mouse Alexa Fluor 546 [Life Technologies #A11018]; 1:200). For in situ proximity ligation assay, coverslips were processed using the Duolink Red mouse/rabbit kit using the protocol provided (Sigma #DU092101) with the antibody dilutions above. The ratio of puncta/nuclei for each experimental condition was calculated by counting all puncta and nuclei in five 60× images. One-way ANOVA was used to compare the ratios between the experimental conditions (vehicle (VHC), 30 m, 6 hr, 24 hr). Confocal microscopy was used for imaging.

Dose Response Growth Assays and Synergy Measurements.

MCF-7 and ZR75.1 cells were reverse transfected with control or CDH1 siRNA as described above into 96-well plates (9,000 cells/well) in 100 µl of media/well. Cells were treated with 3× vehicle (DMSO), OSI-906 (Selleckchem #S1091) or BMS-754807 diluted in 50 µl of media for a final volume in each well of 150 µl (n=6 per concentration). Plates (2D and ultra-low attachment [ULA; Corning #3474]) were collected on day 6 and viability was measured using CellTiter Glo Viability assay (Promega #G7572). $EC_{50}$ values for viability were calculated by non-linear regression and statistical differences evaluated using sum-of-squares Global f-test ($p<0.05$). For synergy experiments, SUM44PE and MDA-MB-134 cells were plated in 96-well ULA plates (18,000 cells/well) in 100 µl of media/well. Cells were treated with 6× vehicle (DMSO), OSI-906, BMS-754807, or BEZ235 (Selleckchem #S1009) diluted in 25 µl of media such that the combination of two drugs resulted in 150 µl of total volume in each well (n=2 per experiment). Synergy was calculated using the Median-Effect Principle and Combination Index-Isobologram Theorem (Chou-Talalay)[27]. Combination index values for ED50, ED75, ED90 are shown as a mean±SEM from n=3 independent experiments.

In Vivo ILC Xenograft Growth and Explant Culturing.

MDA-MB-134 cells ($5\times10^6$ cells) and BCK4 cells ($5\times10^6$ cells) were injected into the right inguinal mammary fat pads of 7-8 week old NOD.Cg-Prkdcscid Il2rgtm1Wjl/SzJ (NSG; The Jackson Laboratory) and NOD.CB17-Prdkcscid/J mice (NOD SCID; The Jackson Laboratory), respectively (implanted with 0.36 mg 90-day slow release estradiol pellets [Innovative Research of America #SE-121]) and grown to a tumor volume of 350 mm³. Tumors were collected, minced into 1-2 mm³ chunks of tumor tissue, and plated onto Vetspon Absorbable Hemostatic Gelatin sponges (Patterson Veterinary #07-849-4032) in 12-well tissue culture plates containing 1.5 ml of explant media (DMEM/F12+10% FBS with 10 mM HEPES, 1 mg/ml BSA, 10 µg/ml insulin, 10 µg/ml hydrocortisone, 1× antibiotic-antimycotic solution [Thermo Fisher #15240-062]). Media was treated with vehicle or 1 µM BMS-754807 for 72 hours. Tissue was collected by formalin fixation followed by paraffin embedding. Sections were stained for Ki67 (Dako #M7240; 1:100) using standard immunohistochemistry technique. Nuclei were quantified by counting all clearly defined nuclei within each tissue section (n=3-6). Two-tailed student's t-test was used to determine statistical difference between vehicle and BMS-754807 treatment ($p<0.05$).

TCGA Data Analysis.

TCGA RNA-seq expression data were downloaded as transcripts per million (TPM) from the Gene Expression Omnibus database (GEO: GSE62944) and log 2(TPM+1) for gene-level results were used. TCGA Reverse Phase Protein Array (RPPA) data were downloaded as median-normalized, batch-corrected expression values from TCPA (Level 4, version 4.0). ER+ IDC (n=417) and ILC (n=137) samples with both RNA-Seq and RPPA data were used for all analyses. Mann-Whitney U tests were used to compare expression, Spearman's rho to compare correlations, and a chi-square test to compare proportions between ILC and IDC tumors. All were calculated using R (version 3.4.1). The median expression values for IGF1 and pIGF1R across ER+ IDC and ILC tumors (n=554) were used as cutoffs for FIG. 9G.

Results

Loss or Inhibition of E-Cadherin Results in Enhanced IGF1R Activity.

Figure 1B:
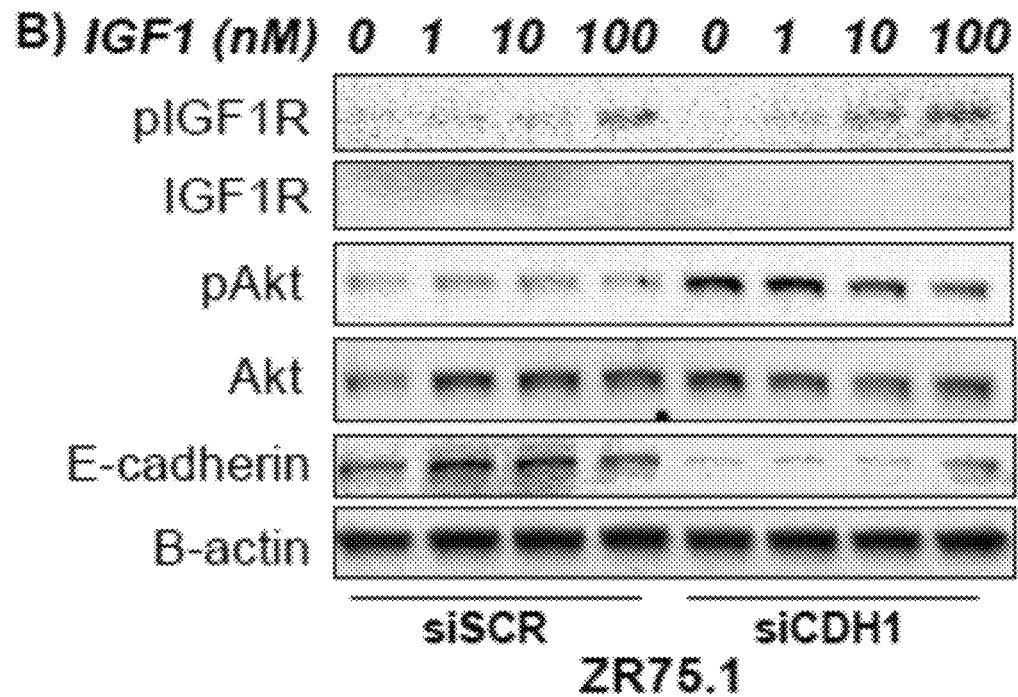
Figure 1C:
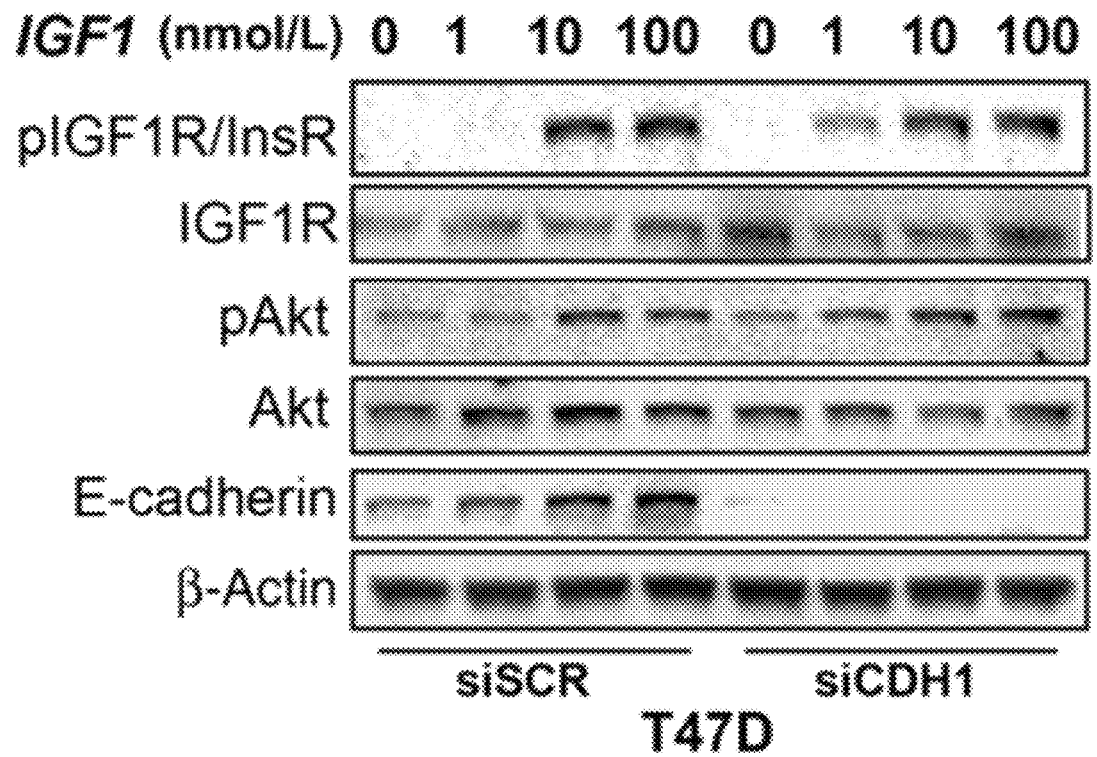
Figure 1D:
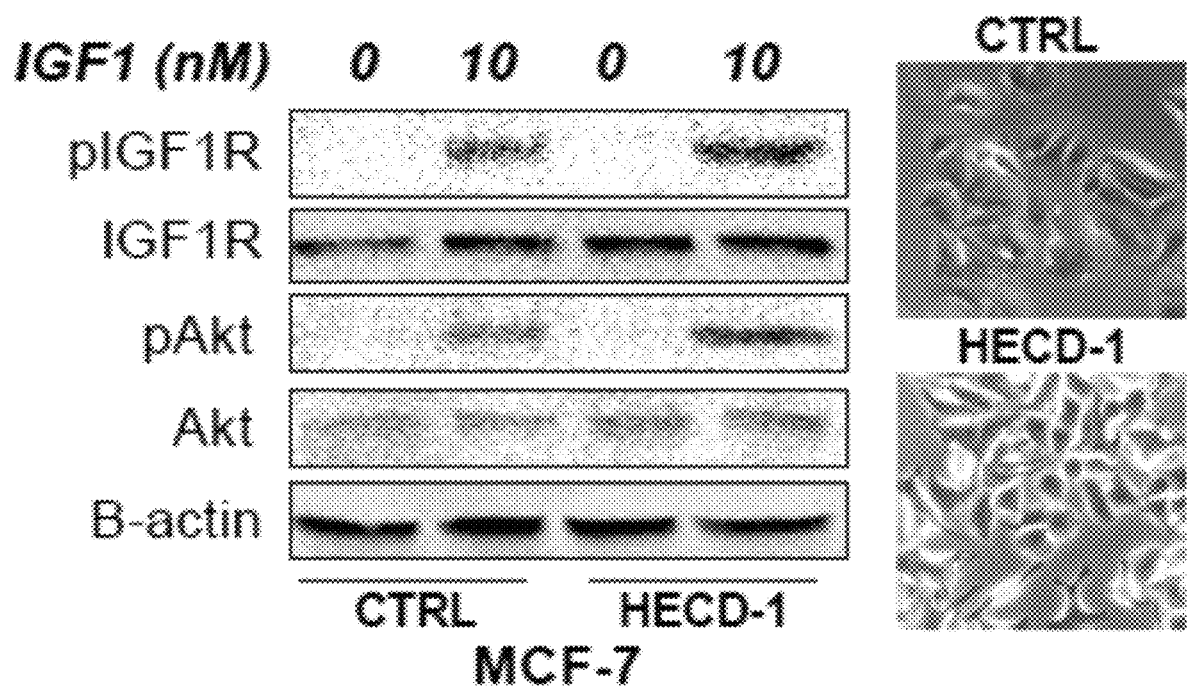
Figure 1E:
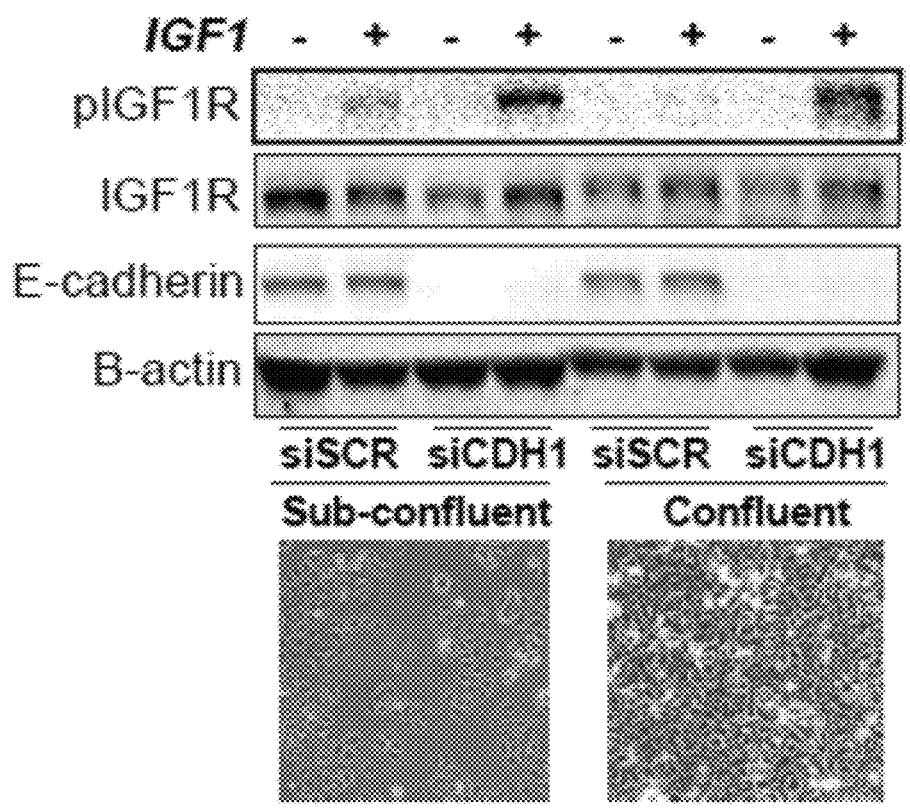

To validate previously published data and to further understand the regulation of the IGF1 signaling pathway by E-cadherin, E-cadherin (CDH1) was silenced by siRNA knockdown in a panel of three estrogen receptor (ER)-positive invasive ductal breast carcinoma (IDC) cell lines and then stimulated with a dose series of IGF1 (0, 1, 10, 100 nM). MCF-7, ZR75.1, and T47D E-cadherin knockdown (siCDH1 siRNA) cells showed enhanced sensitivity to IGF1 compared to the scramble control (siSCR siRNA) cells, most notable at the 1 nM dose of IGF1, resulting in increased phosphorylation of IGF1R and Akt (FIG. 1A-C). As a complementary approach, E-cadherin function was inhibited in MCF-7 cells using the HECD-1 monoclonal antibody that binds the extracellular domain of E-cadherin and prevents adherens junction formation. Similar to knockdown of E-cadherin, HECD-1 treated cells showed increased IGF1R and Akt phosphorylation compared to control (FIG. 1D). Additionally, confluency-dependent IGF1R signaling was evaluated to understand the effect of increased cell-cell contacts. A confluent monolayer of MCF-7 cells lost the ability to initiate IGF1R signaling upon ligand stimulation compared to a sub-confluent monolayer (approx. 40-50%), however, the knockdown of E-cadherin rescued signaling in both confluency conditions (FIG. 1E).

Figure 1F:
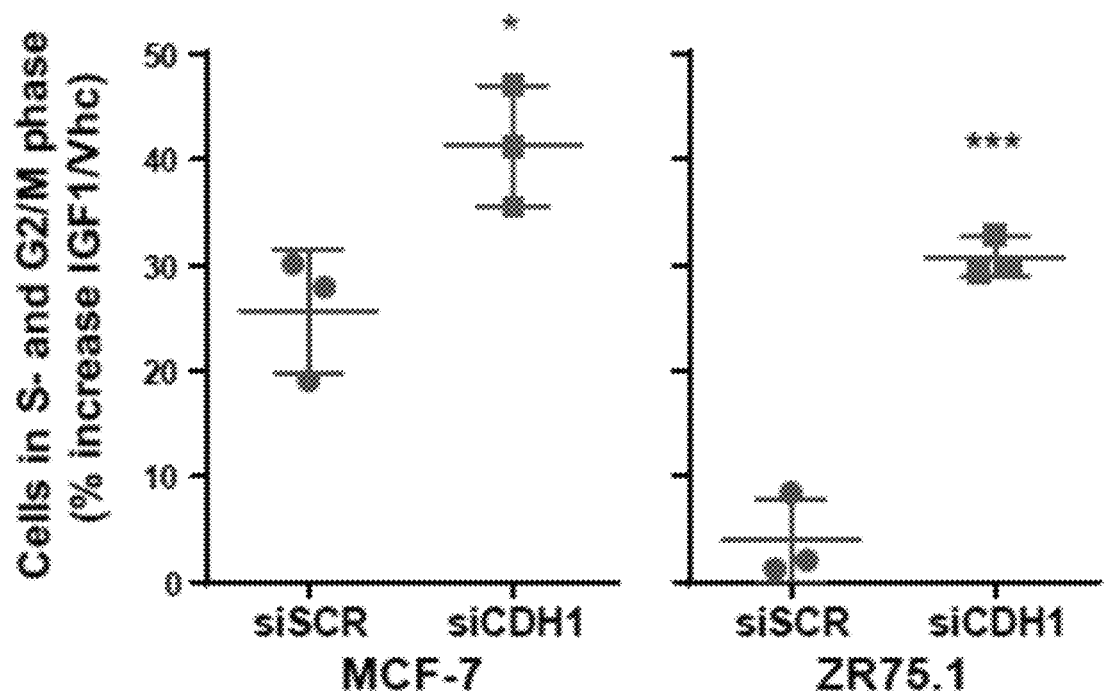
Figure 2:
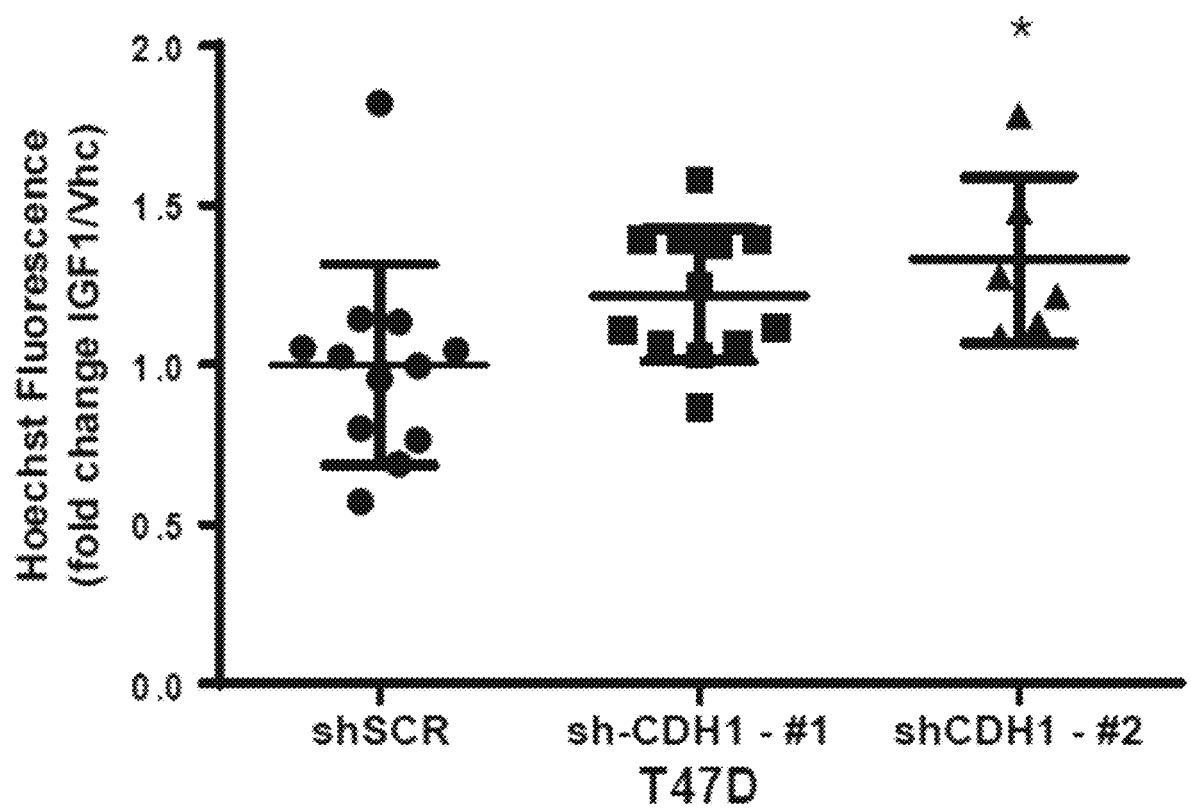
FIG. 2 shows knockdown of E-cadherin (CDH1) expression enhances IGF1-induced proliferation. T47D shSCR and two clones of shCDH1 cells were plated in 96 well plates (9,000 cells per well) in serum-free media. Cells were treated with Vhc or 10 nM IGF1 for 6 days and dsDNA content measured. Statistical difference in Hoechst fluorescence in IGF1 treated cells over vehicle control in each cell line was evaluated using a two-tailed student's t-test (p<0.05). One representative experiment shown; n=2 each with 6 biological replicates. Of note, each shCDH1 clone displayed statistically significant increase in viability compared to control cells in 1 of 2 experiments, with the other trending toward increased viability.

The functional effect of enhanced IGF1 signaling on the cell cycle profile in MCF-7 and ZR75.1 cells with reduced E-cadherin was evaluated. CDH1 knockdown (siCDH1) cells showed a significant increase (p=0.03 and p=0.0005, respectively) in the percentage of cells progressing into the S- and G2/M-phases of the cell cycle following IGF1 treatment compared to control siSCR cells (FIG. 1F). Similarly, slight increases in IGF1-induced cell viability in siCDH1 compared to siSCR in T47D cells were observed (FIG. 2). As occasionally used herein, a cell type (e.g., MCF-7) transfected with a siRNA (e.g., siSCR) can be referred to by the siRNA name adjacent the cell type name (e.g., "siSCR MCF-7 cells" or "MCF-7 siSCR cells"), or where clear, in front of the term "cells" (e.g., "siSCR cells") or clear variations thereof.

Figure 3A:
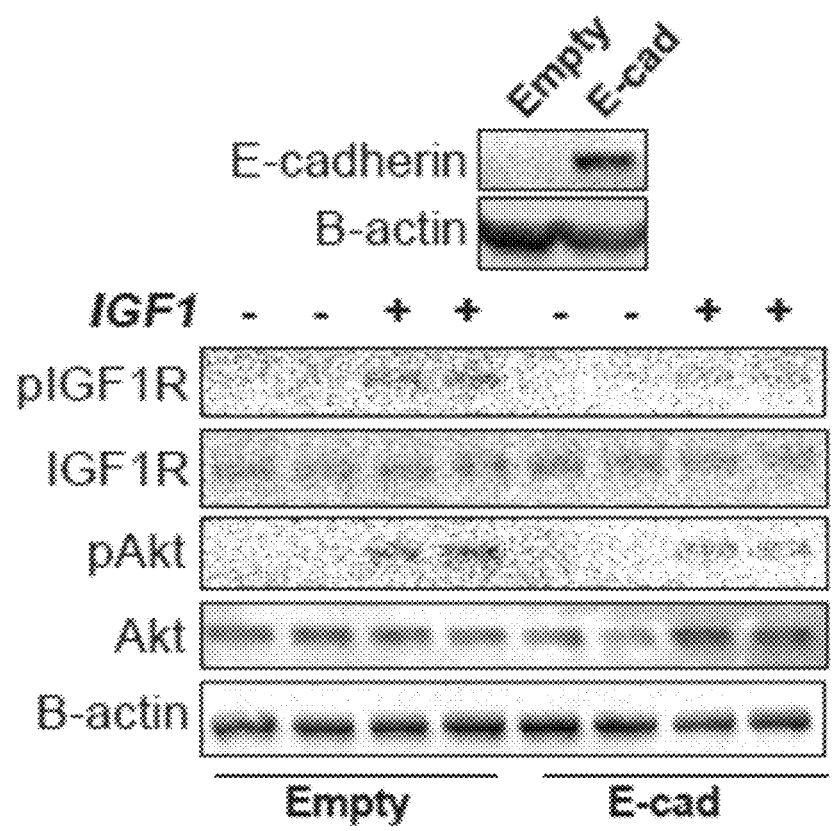
FIGS. 3A and 3B show overexpression of E-cadherin in MDA-MB-231 cells inhibits IGF1R signaling, although adherens junctions did not form. MDA-MB-231 (MM231) cells lacking detectable E-cadherin protein expression were stably transfected with empty of hE-cadherin-pcDNA3 vector. Cells were stimulated with Vhc or 10 nM IGF1 for 10 min and IGF1R and Akt signaling assessed by immunoblot (shown in duplicate biological replicates) (FIG. 3A).
Figure 3B:
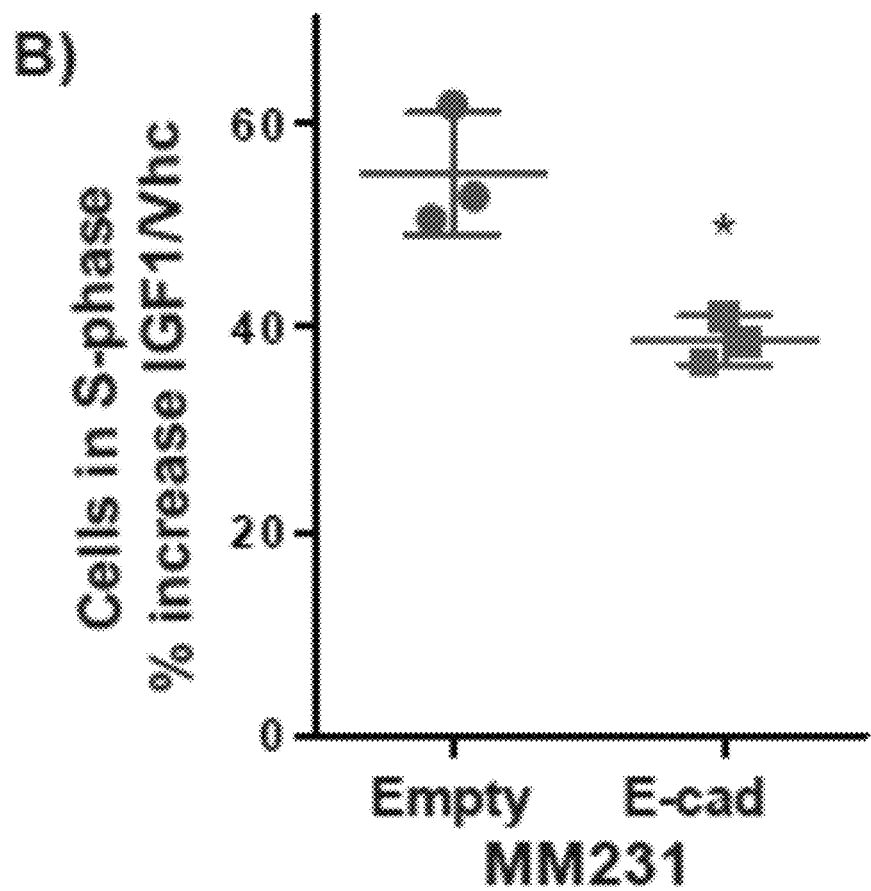

E-cadherin was overexpressed in MDA-MB-231 cells, an ER-negative IDC cell line with undetectable E-cadherin protein by immunoblot to determine if overexpression represses signaling. Although adherens junction formation was not observed (data not shown), E-cadherin overexpressing cells demonstrated decreased phosphorylation of IGF1R and Akt compared to empty vector control cells (FIG. 3A), and significantly less cell cycle progression in response to IGF1 stimulation (p=0.011; FIG. 3B).

Loss of E-Cadherin Enhances Sensitivity to IGF1R Inhibition.

Figure 4A:
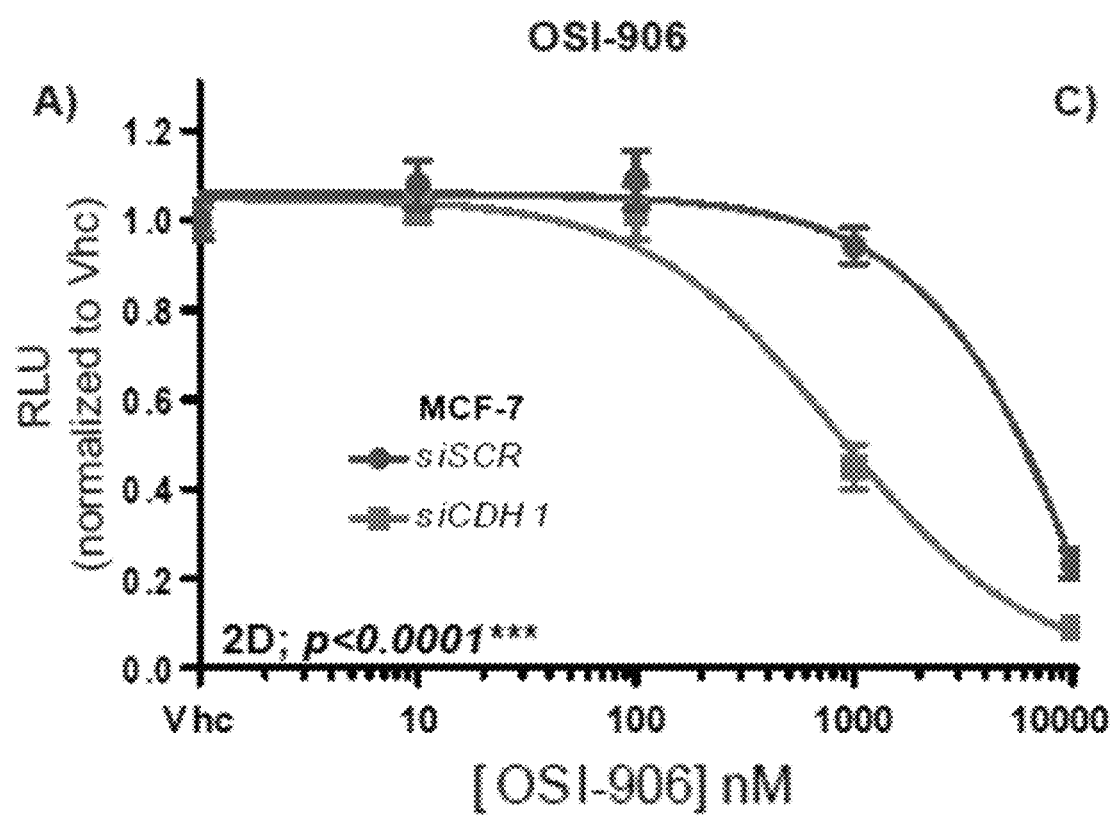
FIGS. 4A, 4B, 4C, and 4D show knockdown of E-cadherin increases sensitivity to IGF1R inhibition in breast cancer cells. MCF-7 cells were reverse transfected with SCR or CDH1 siRNA and seeded into 96-well 2D or ULA plates and treated with IGF1R pathway inhibitors OSI-906 or BMS-754807 for 6 days. Conditions in the panels as follows.
Figure 4B:
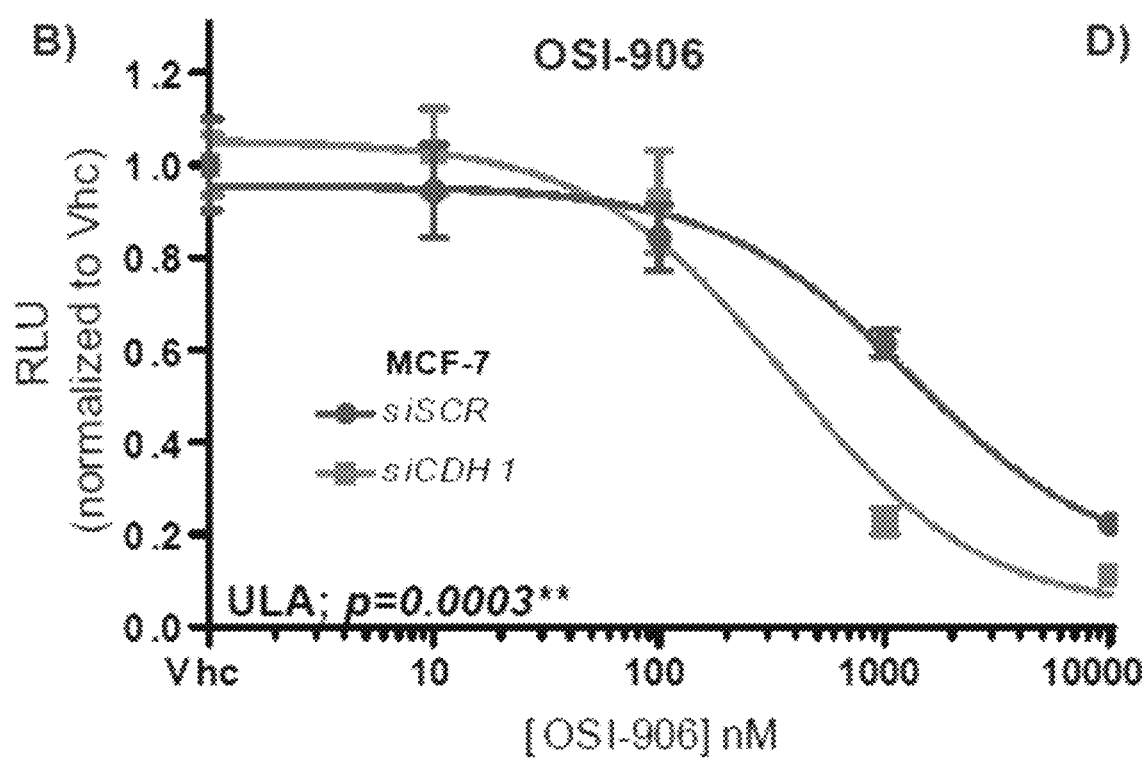
Figure 4C:
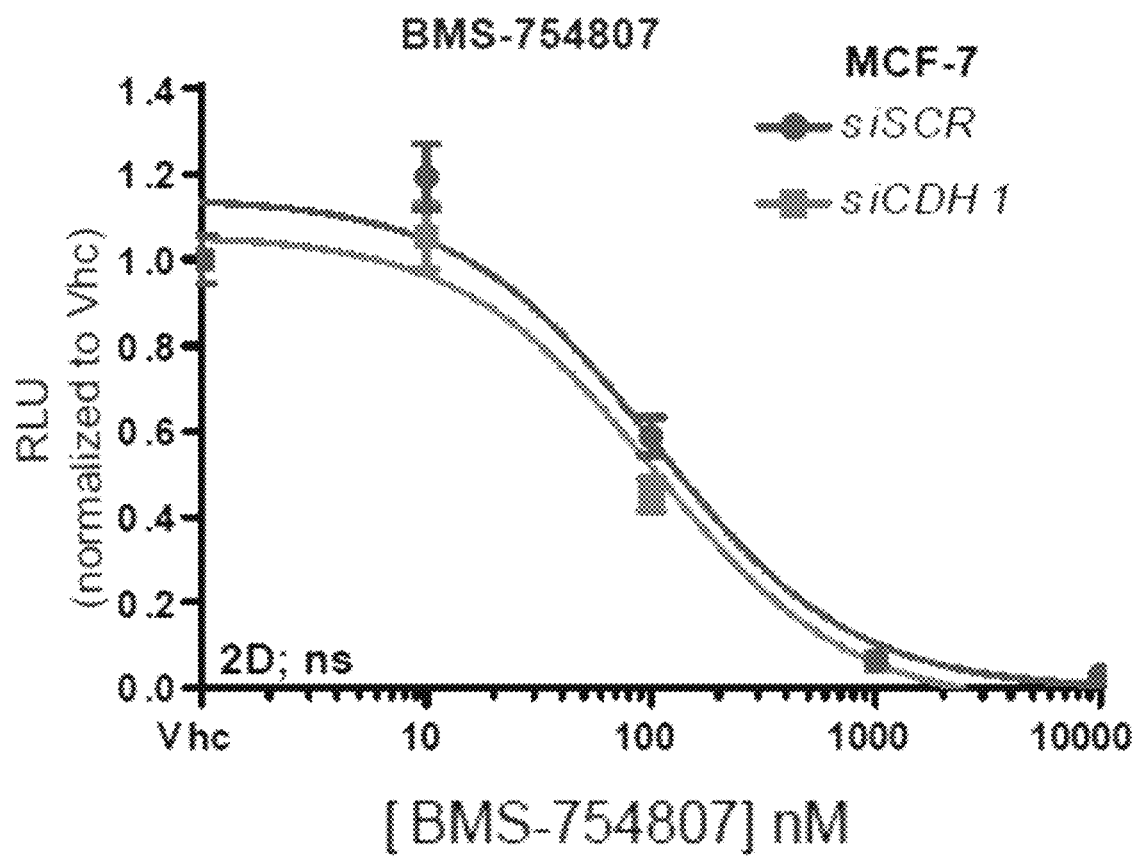
Figure 4D:
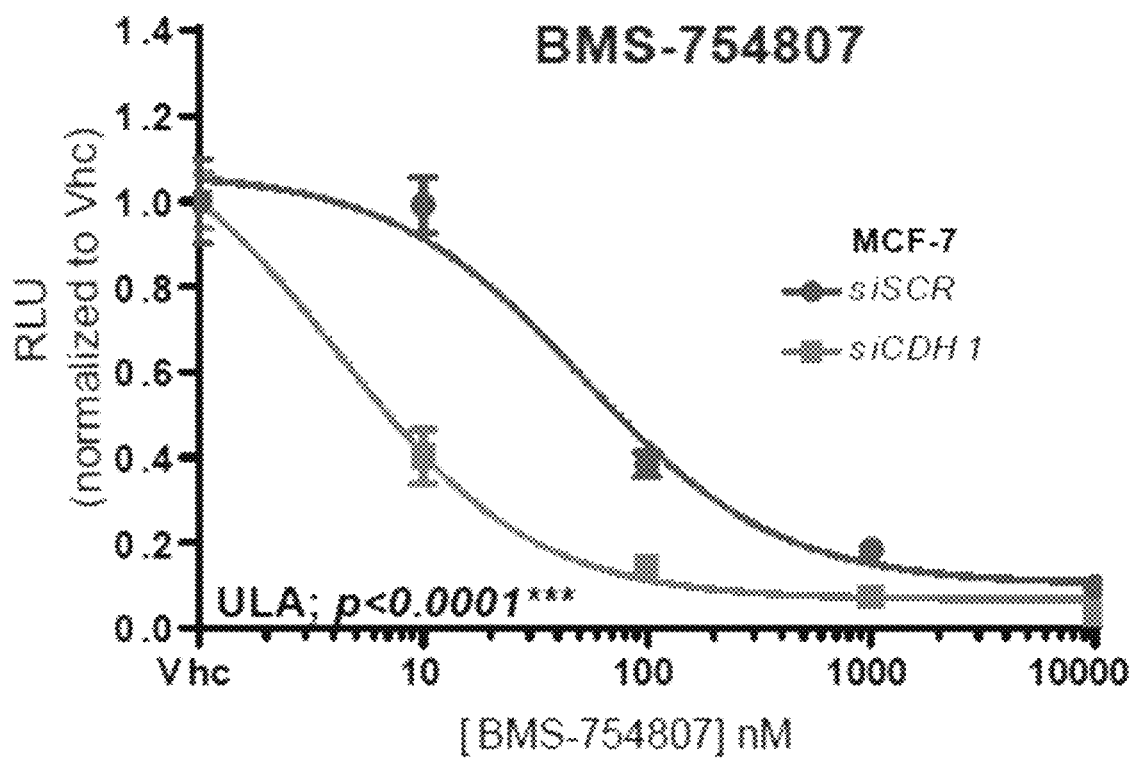
Figure 5A:
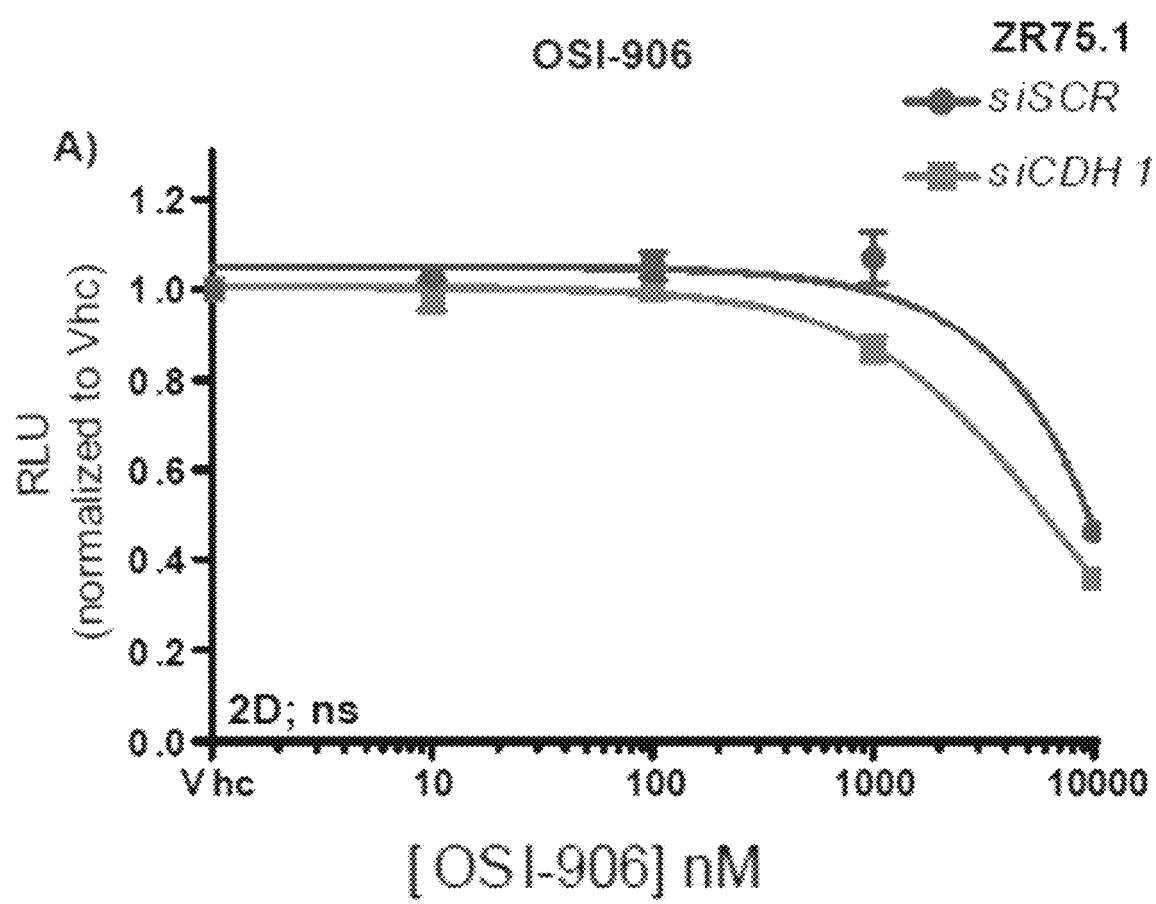
FIGS. 5A and 5B show knockdown of E-cadherin increases sensitivity to IGF1R inhibition in breast cancer cells. ZR75.1 cells were reverse transfected with SCR or CDH1 siRNA and seeded into 96-well 2D (FIG. 5A) or ULA (FIG. 5B) plates and treated with OSI-906 for 6 days. CellTiter Glo assay was used to assess cell viability (relative luminescence). EC50 values for viability were calculated by non-linear regression and statistical differences evaluated using sum-of-squares Global f-test (p<0.05; representative experiment shown; n=3 each with 6 biological replicates).
Figure 5B:
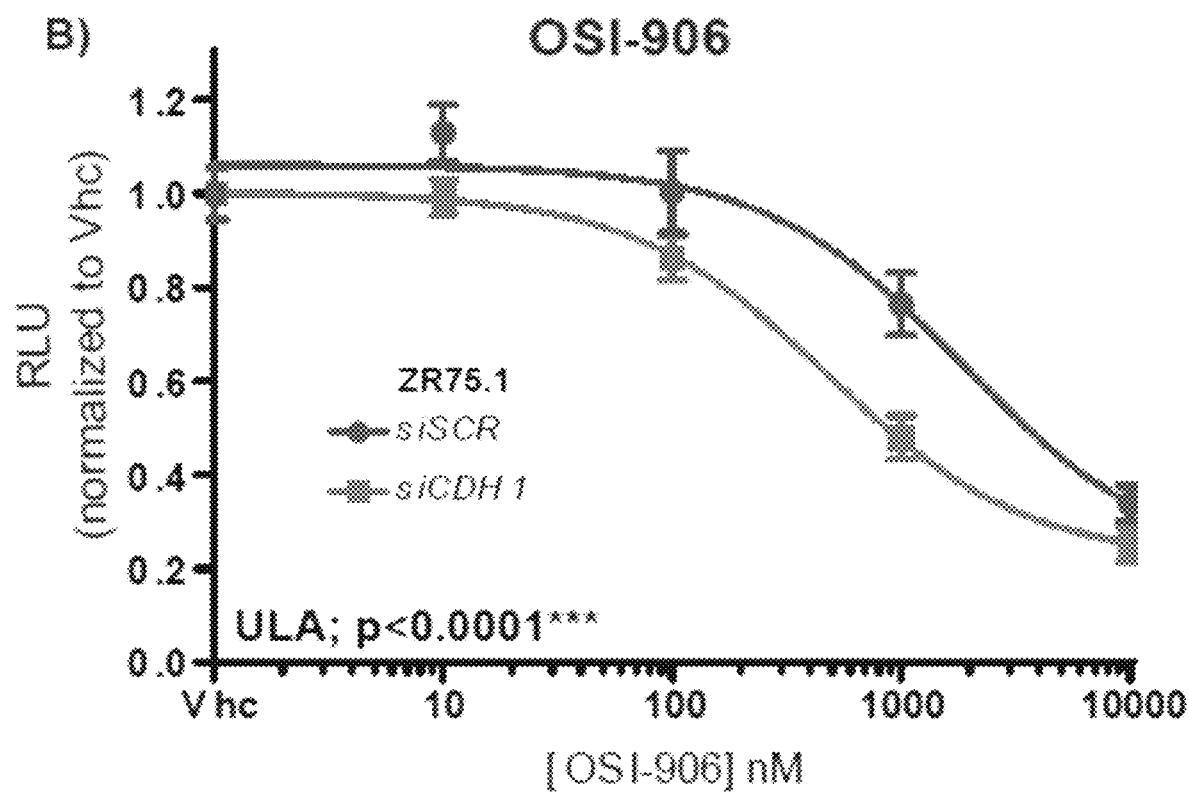
Figure 6A:
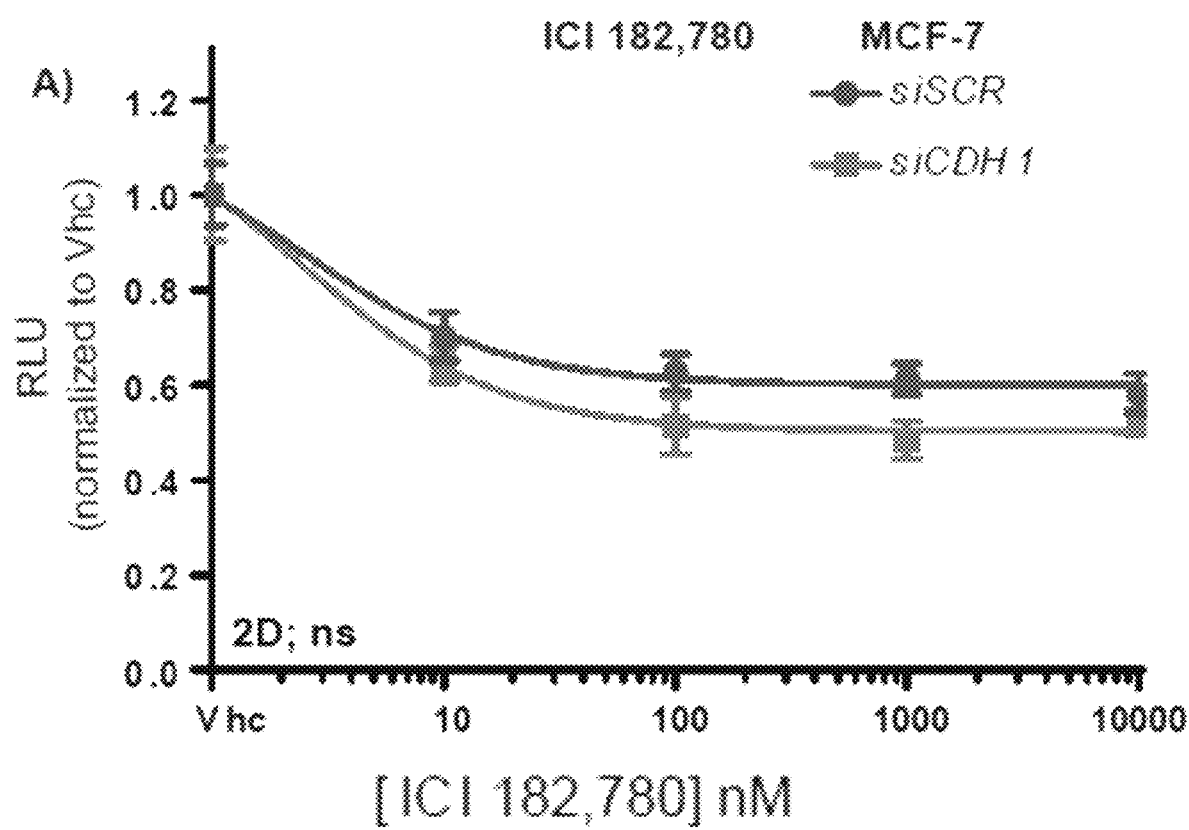
FIGS. 6A and 6B show loss of E-cadherin in breast cancer cells does not change sensitivity to ICI 182,780. MCF-7 cells were reverse transfected with SCR or CDH1 siRNA and seeded into 96-well 2D (FIG. 6A) or ULA (FIG. 6B) plates and treated with ICI 182,780 for 6 days. CellTiter Glo assay was used to assess cell viability (relative luminescence). EC50 values for viability were calculated by non-linear regression and statistical differences evaluated using sum-of-squares Global f-test (p<0.05; one independent experiment, n=6 biological replicates).
Figure 6B:
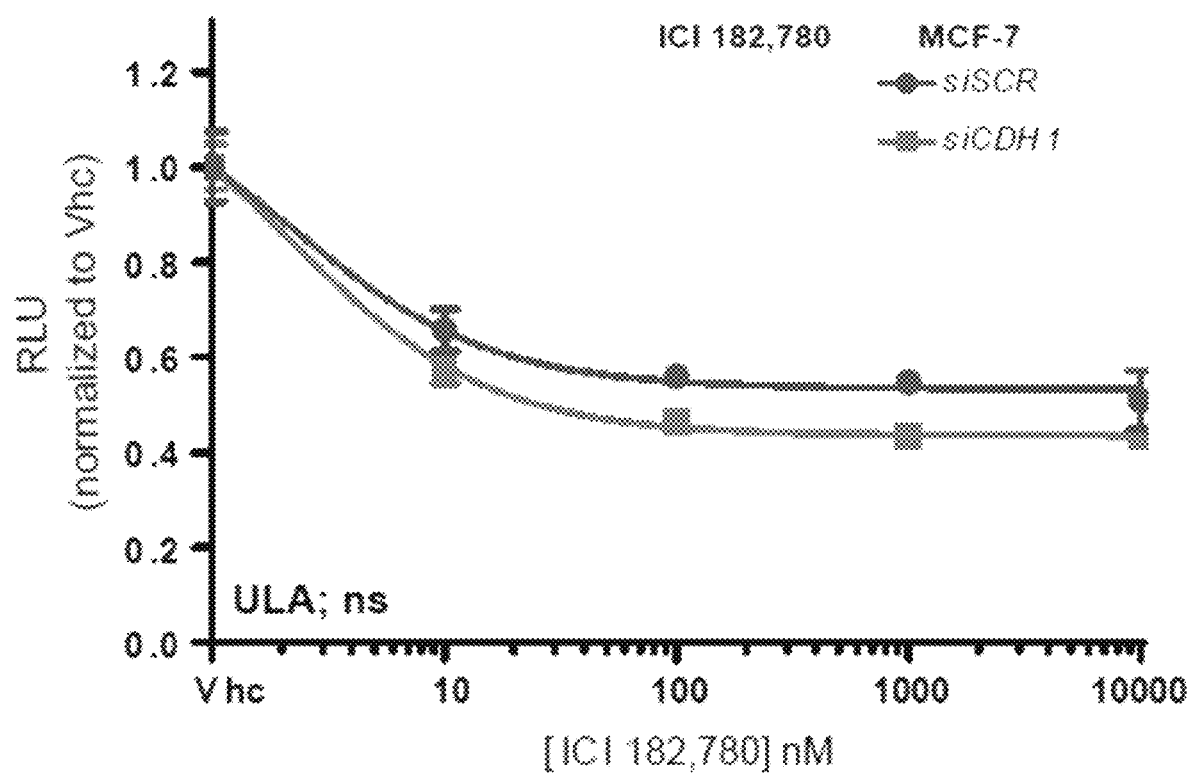

Due to the enhanced sensitivity of E-cadherin knockdown cells to IGF1 stimulation, it was determined whether loss of E-cadherin in MCF-7 and ZR75.1 cells also increased sensitivity to the IGF1R ATP-competitive small molecule inhibitors, OSI-906 (OSI) and BMS-754807 (BMS). In addition to 2D adherent culture, ultra-low attachment suspension growth (ULA) was examined, since increased cell viability in E-cadherin knockdown cells was observed under these conditions (data not shown), possibly due to the reported annoikis resistance of cells lacking E-cadherin expression MCF-7 siCDH1 cells displayed significantly decreased viability in response to OSI treatment, compared to siSCR cells in both 2D (p<0.0001; FIG. 4A) and ULA (p=0.0003; FIG. 4B) growth conditions resulting in a shift in the $EC_{50}$. Additionally, ZR75.1 siCDH1 cells showed significantly decreased viability and a shift in the EC50 when grown in ULA (p<0.0001; FIG. 5B) in response to OSI treatment, but not in the 2D growth condition (FIG. 5A). Similarly, MCF-7 siCDH1 cells showed decreased viability in response to BMS compared to siSCR cells the ULA growth condition (p<0.0001; FIG. 4D), but no significant difference in 2D (FIG. 4C). Overall, these data show the loss of E-cadherin enhances breast cancer cell sensitivity to IGF1R inhibition. Growth response of MCF-7 siSCR and siCDH1 cells treated with ICI 182,780 (ICI), a selective estrogen receptor downregulator (SERD), was also tested and no statistical difference in $EC_{50}$ was observed, showing that the loss of E-cadherin does not generally sensitize cells to all small molecule drug treatments (FIG. 6).

IGF1R and E-Cadherin Directly Interact in ER+ Breast Cancer Cells Resulting in Recruitment of IGF1R to Adherens Junctions.

Figures 7A, 7B, 7C, 7D:
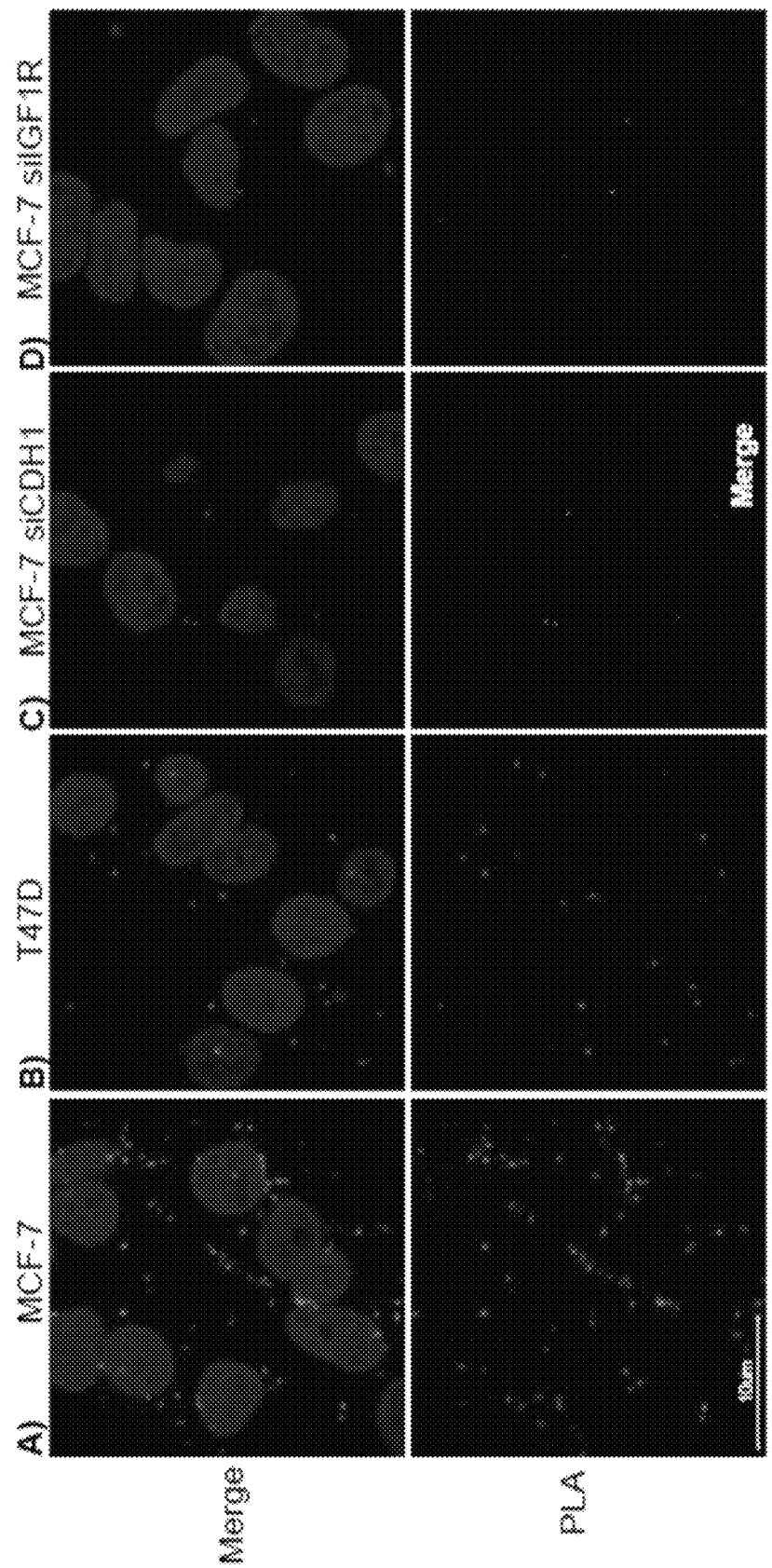
Figures 8D, 8E, 8F:
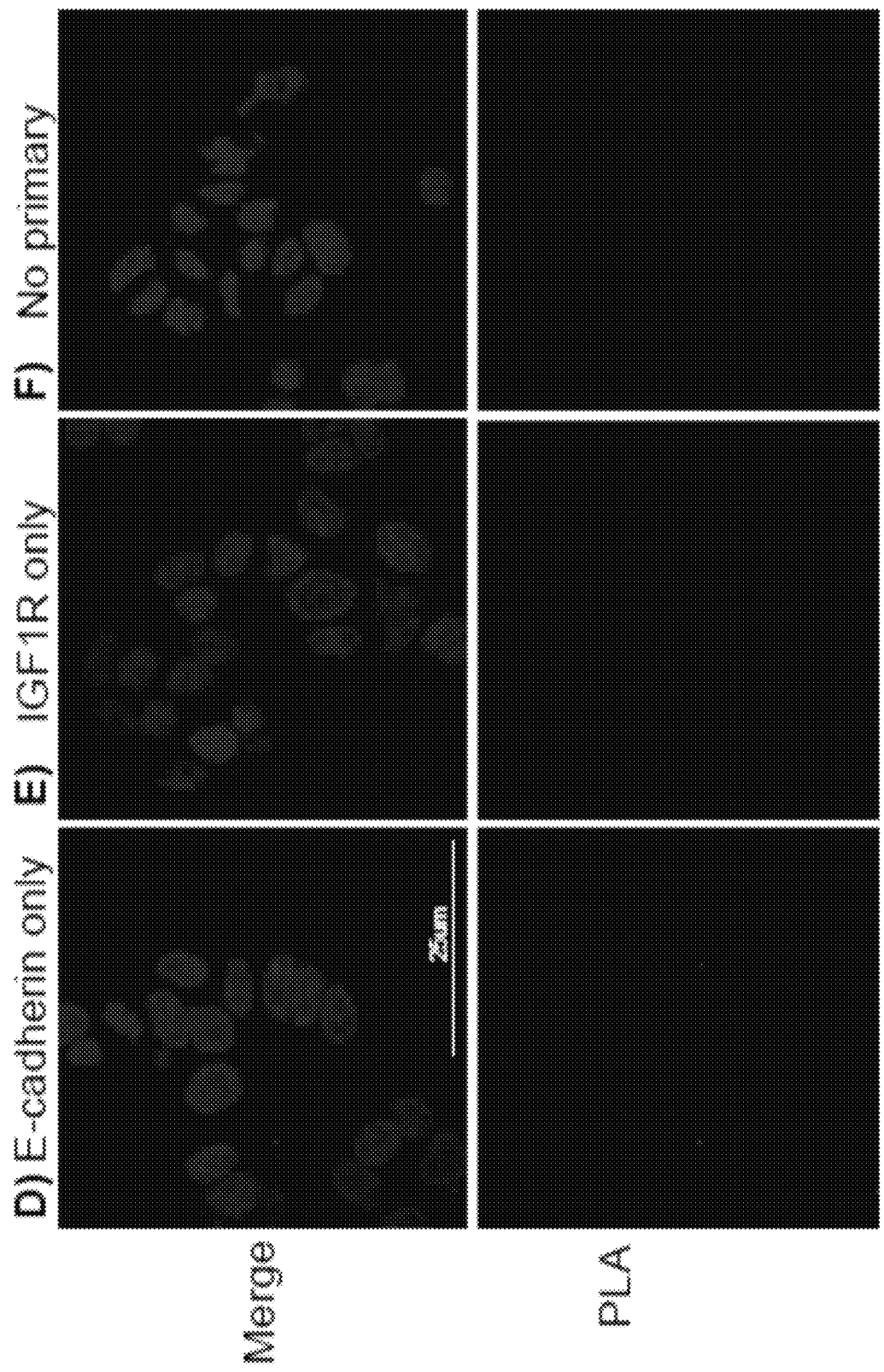

To understand how E-cadherin regulates IGF1R, it was assessed whether IGF1R and E-cadherin directly interact in breast cancer cells using in situ proximity ligation assay (PLA). The sensitivity and specificity of PLA allows for detection of endogenous interacting proteins within proximity of no further than 40 nm. PLA experiments resulted in significant amounts of red fluorescent puncta signals, thereby showing that IGF1R and E-cadherin directly interact in both MCF-7 (FIG. 7A) and T47D cells (FIG. 7B). To demonstrate the specificity of the detection, MCF-7 siRNA knockdown cells lacking E-cadherin (siCDH1; FIG. 7C) or IGF1R (siIGFR; FIG. 7D) as negative controls and observed the red fluorescent puncta signal greatly diminished. These results show that the red fluorescent puncta signals observed in the experiments were due to direct interactions between IGF1R and E-cadherin. Additionally, secondary antibody specificity was confirmed by using each primary antibody alone and a no-primary antibody control. No significant levels of PLA puncta over background were detected (FIG. 8D-F), again showing the specificity of the PLA experiments. Control experiments shown in FIGS. 8A-8C confirmed knockdown of E-cadherin and IGF1R in cells assayed for PLA in FIGS. 7A-7C.

Figure 7I:
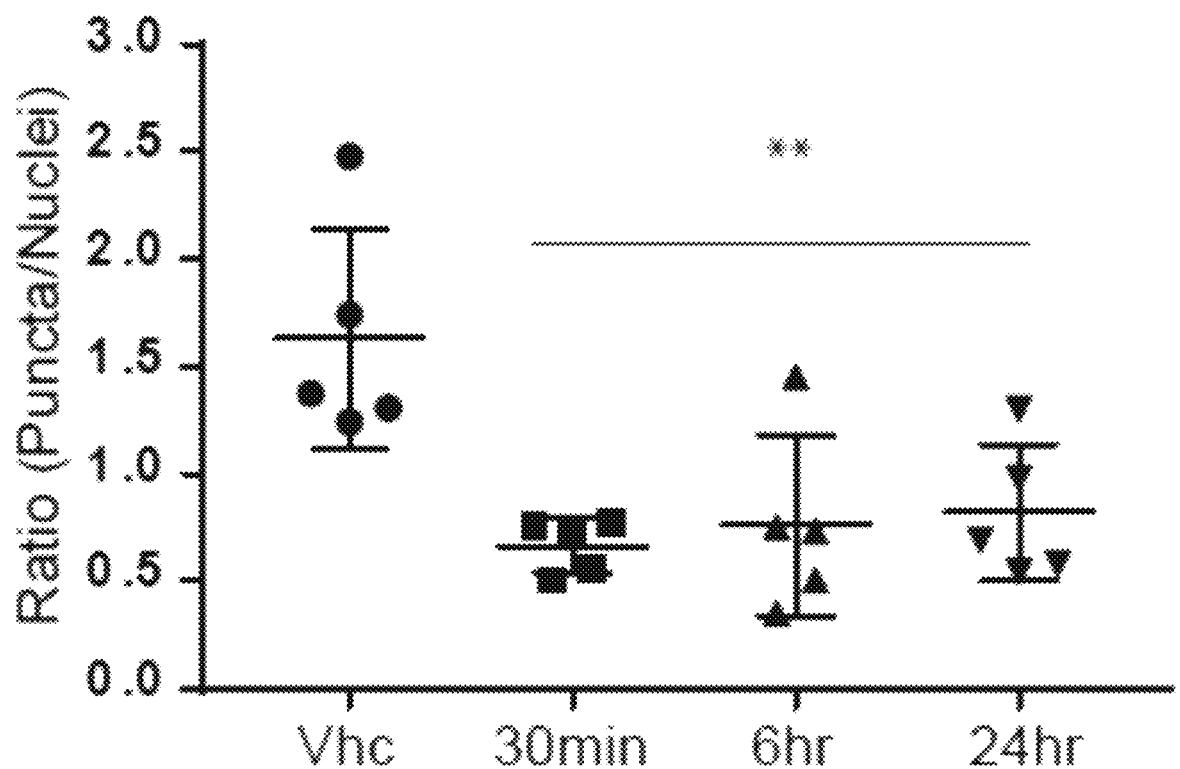

The interaction between IGF1R and E-cadherin following IGF1 stimulation was also examined using PLA. In MCF-7 cells, IGF1 treatment caused a significant decrease in number of fluorescent puncta (p=0.003) at 30 minutes (FIG. 7F), 6 hours (FIG. 7G), and 24 hours (FIG. 7H) after treatment, as compared to vehicle treatment without IGF1 as a negative control (FIG. 7E). These fluorescence results, and the quantitation thereof (FIG. 7I), show that the interaction between the two proteins needs to be disrupted for proper IGF1R function (FIG. 7E-I), possibly explaining why siCDH1 cells have an increased IGF1R signaling capacity compared to control cells.

Figure 7J:
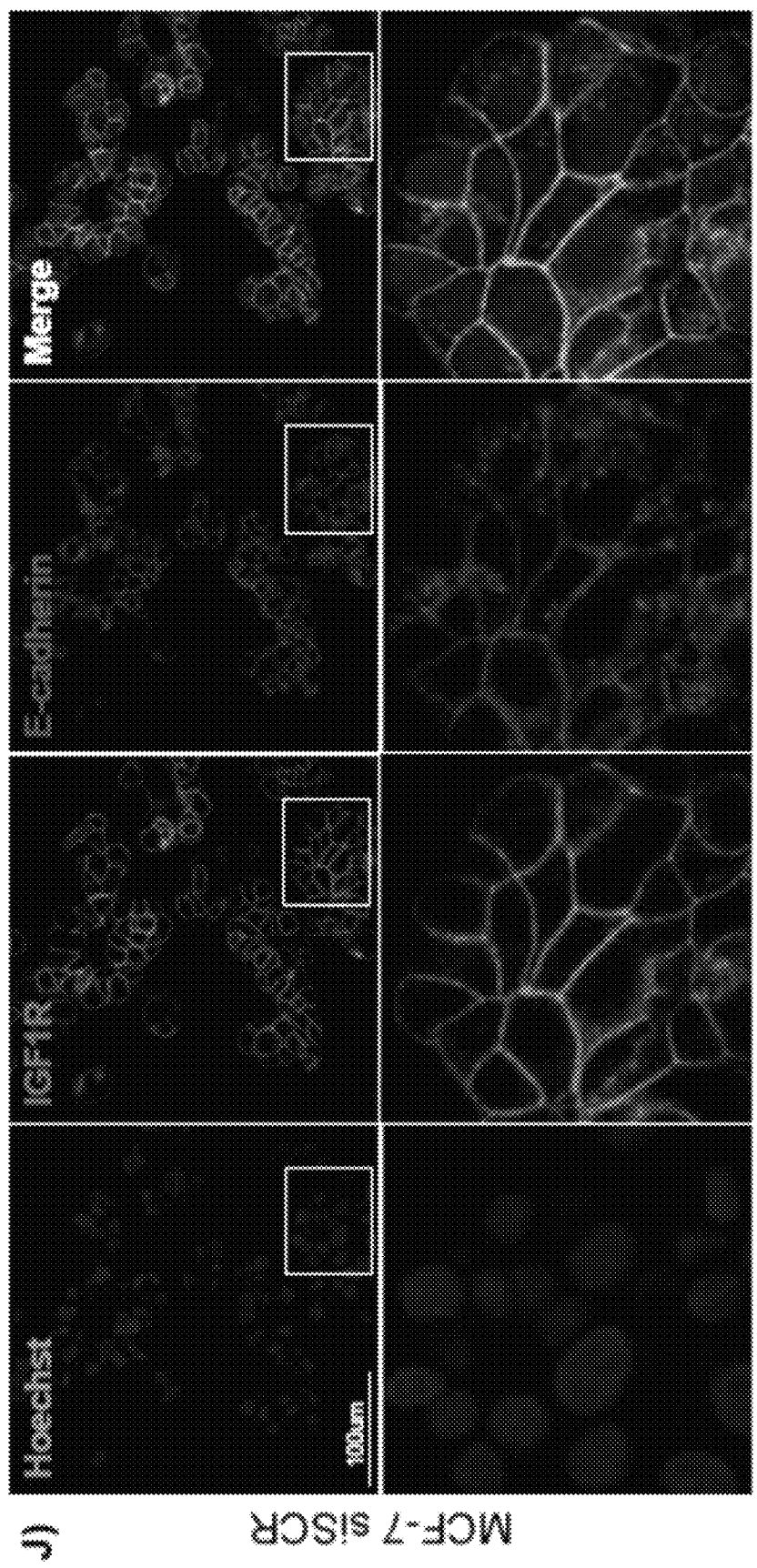

MCF-7 cells were stained for endogenous IGF1R and E-cadherin, and it was determined that IGF1R and E-cadherin co-localize to adherens junctions. Interestingly, co-localization was prominent at the points of cell-cell contact in siSCR control cells, and noticeably absent or reduced on portions of the membrane where there was no cell-cell contact (FIG. 7J), as shown by overlapping fluorescence signals in these same regions. This shows that E-cadherin recruits IGF1R to adherens junctions, perhaps to sequester the receptor as a mechanism of signaling repression. Upon knockdown of E-cadherin in siCDH1 cells, the expression pattern of IGF1R appeared to redistribute equally to the entire cell membrane (FIG. 7K) and reduced overlap of fluorescence signals in the same regions was observed. These results show that E-cadherin influences and regulates IGF1R localization.

Invasive Lobular Breast Cancers (ILC) Display Enhanced IGF1-IGF1R Pathway Activation.

Figure 7K:
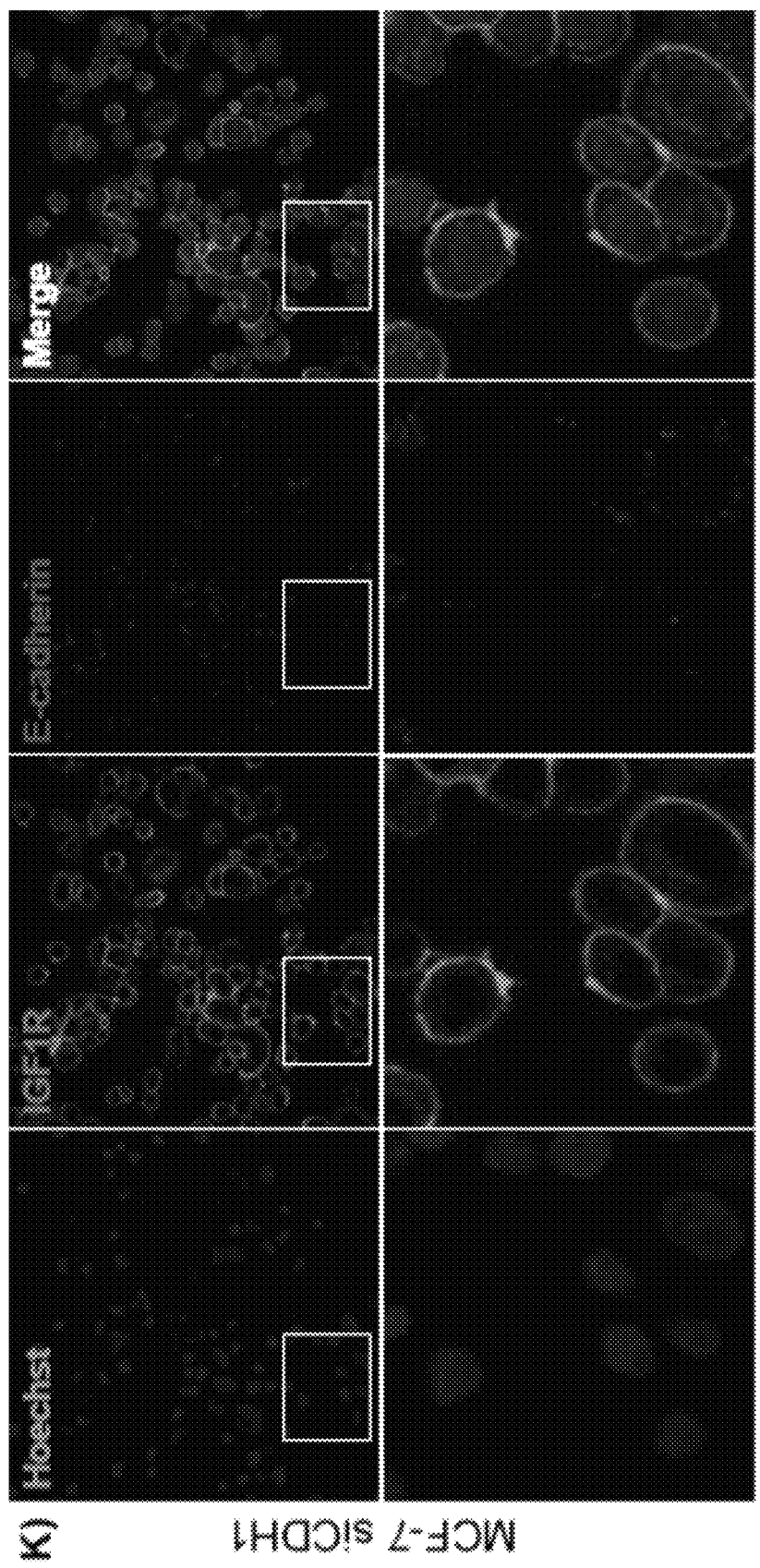

Because knockdown or inhibition of E-cadherin induces hyperactivity of the IGF1R pathway in cell line models, it was investigated whether IGF1R pathway activity is also hyperactivated in ILC, a subtype of breast cancer that accounts for 10-15% of all breast cancer cases and is molecularly classified by its genetic loss of E-cadherin. Because 90-95% of ILC tumors are ER+, focus was placed on this cohort. IGF1R expression and localization was examined in the ER+ ILC cell lines: MDA-MB-134 (MM134; FIG. 9B), SUM44PE (FIG. 9A), and BCK4 (FIG. 9C). IGF1R staining was membranous similar to that observed in MCF-7 siCDH1 E-cadherin knockdown cells (FIG. 7K). Each ILC cell type also showed a lack of membranous E-cadherin staining (FIG. 9A-C). These results show that the tested ER+ ILC cell lines are phenotypically similar to MCF-7 siCDH1 cells with respect to IGF1R expression and localization.

Figure 9D:
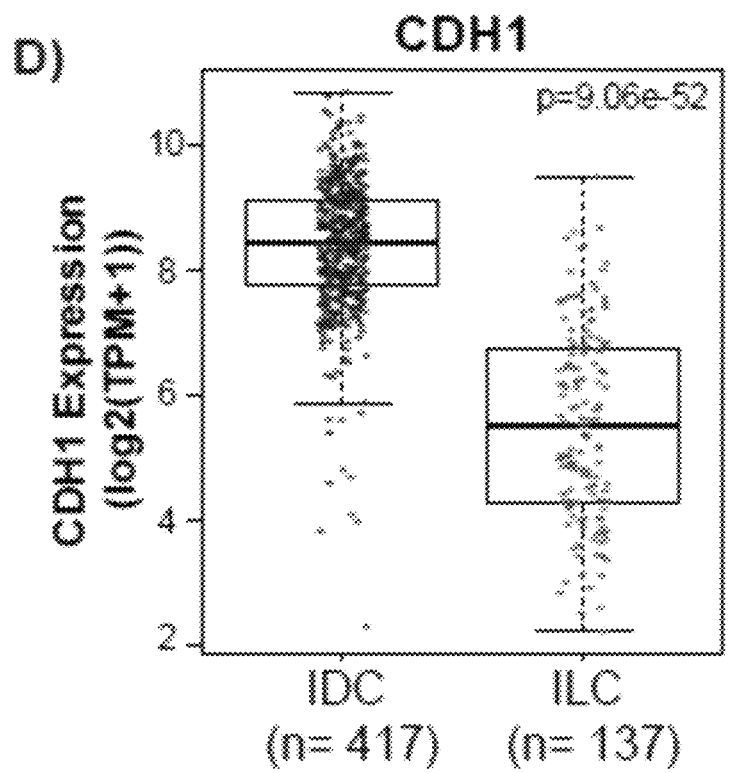
Figure 9E:
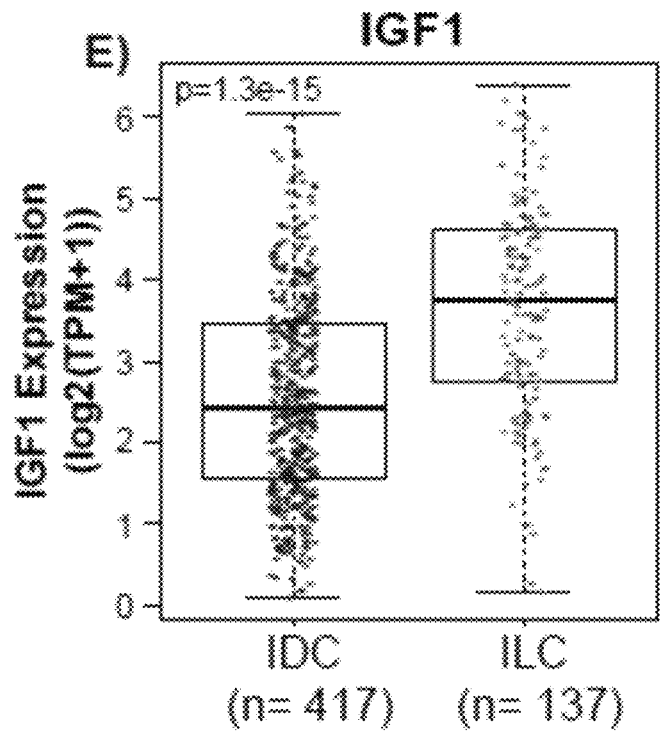
Figure 9F:
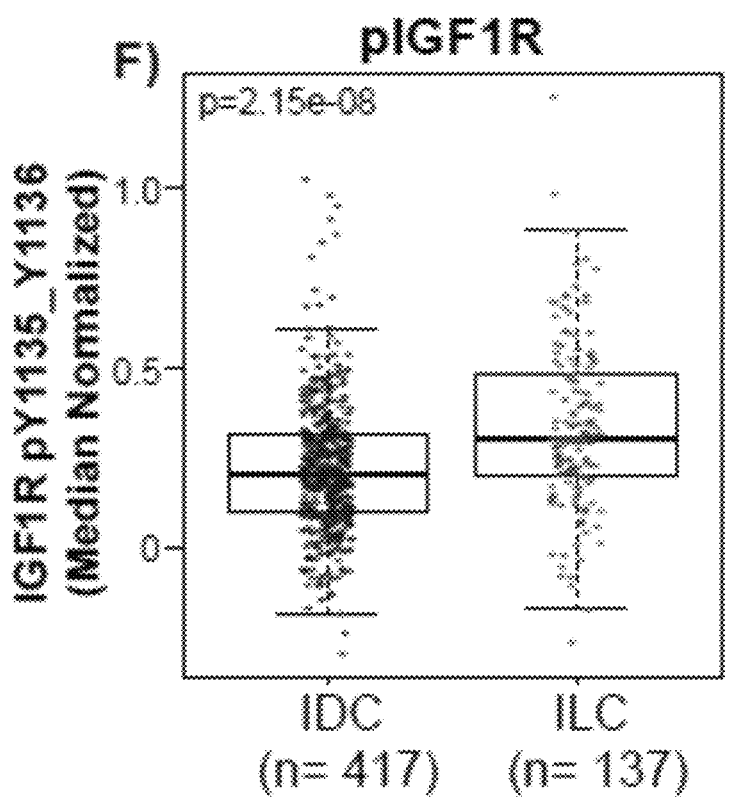
Figure 9G:
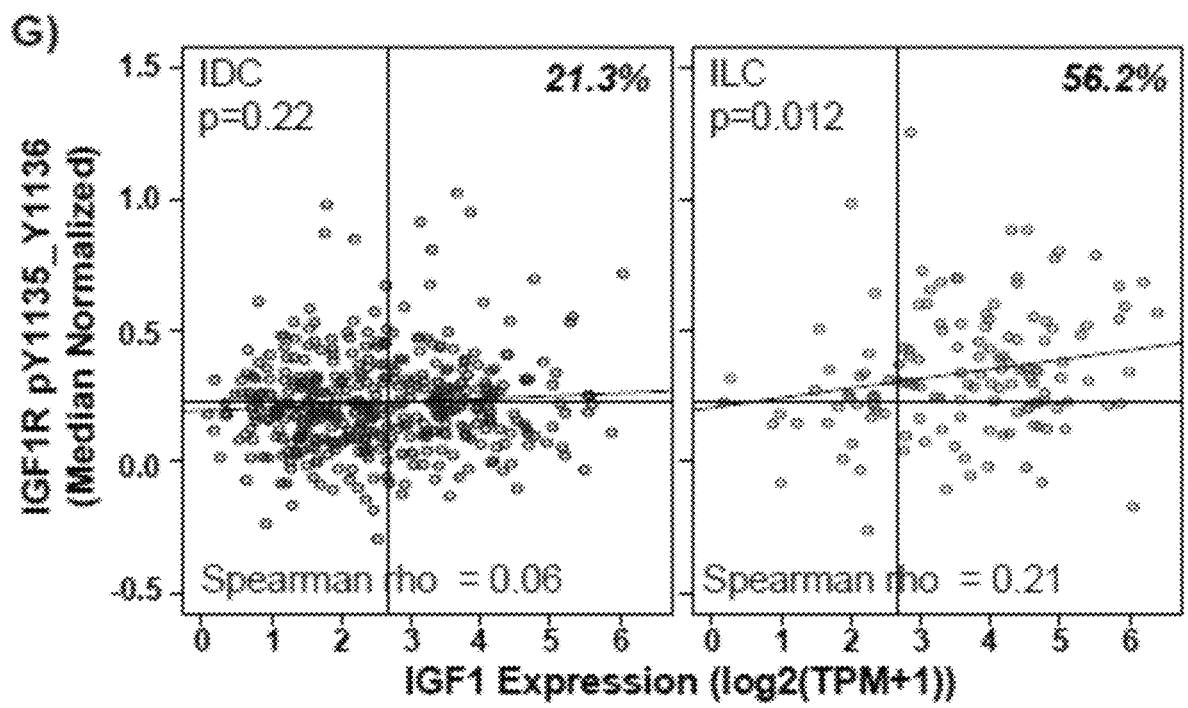
Figure 10A:
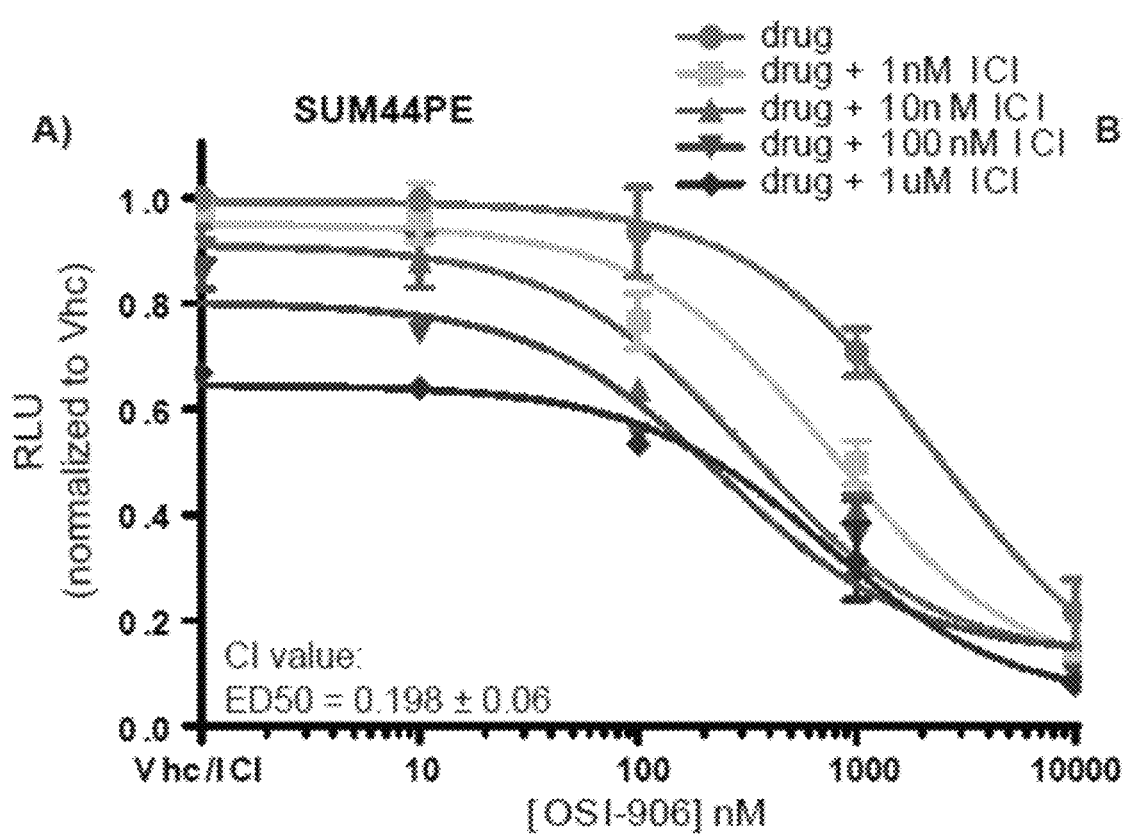
FIGS. 10A, 10B, 10C, 10D, 10E, and 10F show IGF1R pathway inhibitors and endocrine therapy synergize to inhibit cell viability in ILC breast cancer cells. SUM44PE ILC cells were plated into 96-well ULA plates and treated for 6 days with increasing doses of OSI-906 (FIG. 10A, 10B), BMS-754807 (FIG. 10C, 10D), or BEZ235 (FIG. 10E, 10F) in combination with increasing doses of ICI 182,780. The dose response curves (FIG. 10A, 10C, 10E) and heat maps (FIGS. 10B, 10D, 10F) shown indicate inhibition of cell viability (CellTiter Glo). Representative experiment shown; n=3 independent experiments each with 2 biological replicates per combination of doses.
Figure 10B:
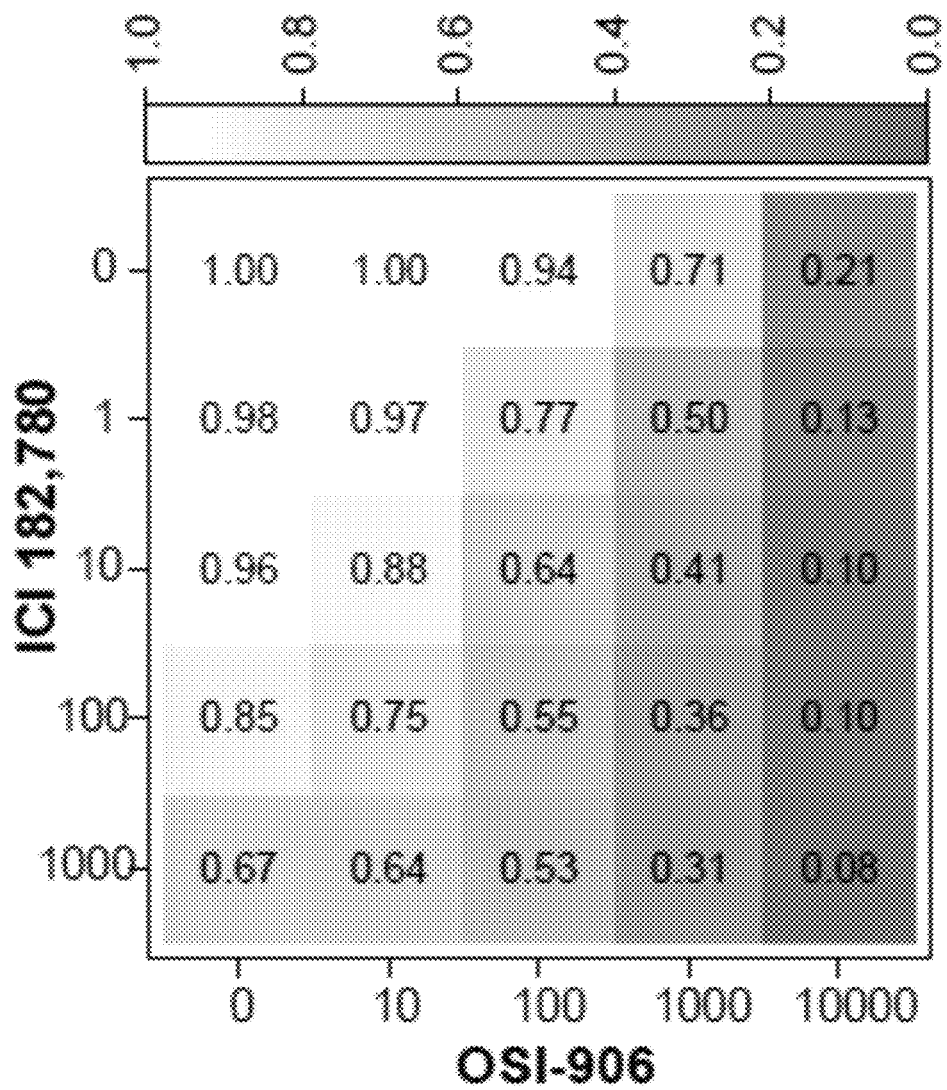
Figure 10C:
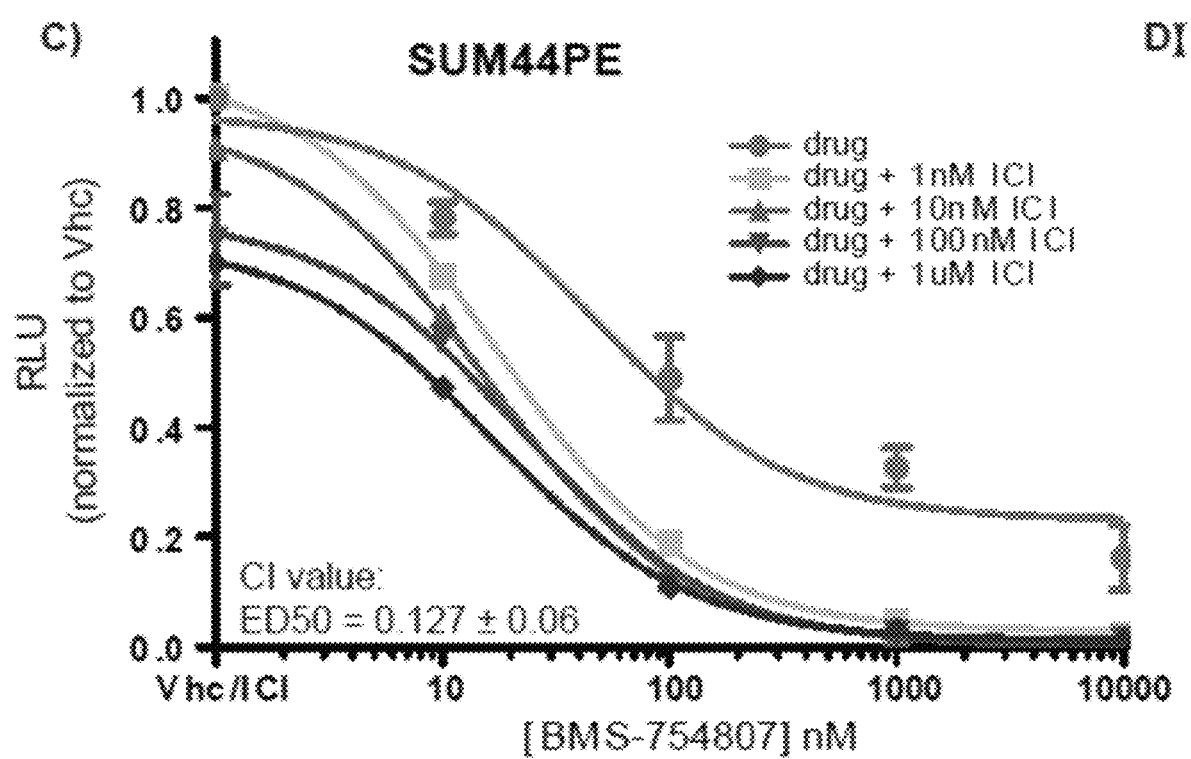
Figure 10D:
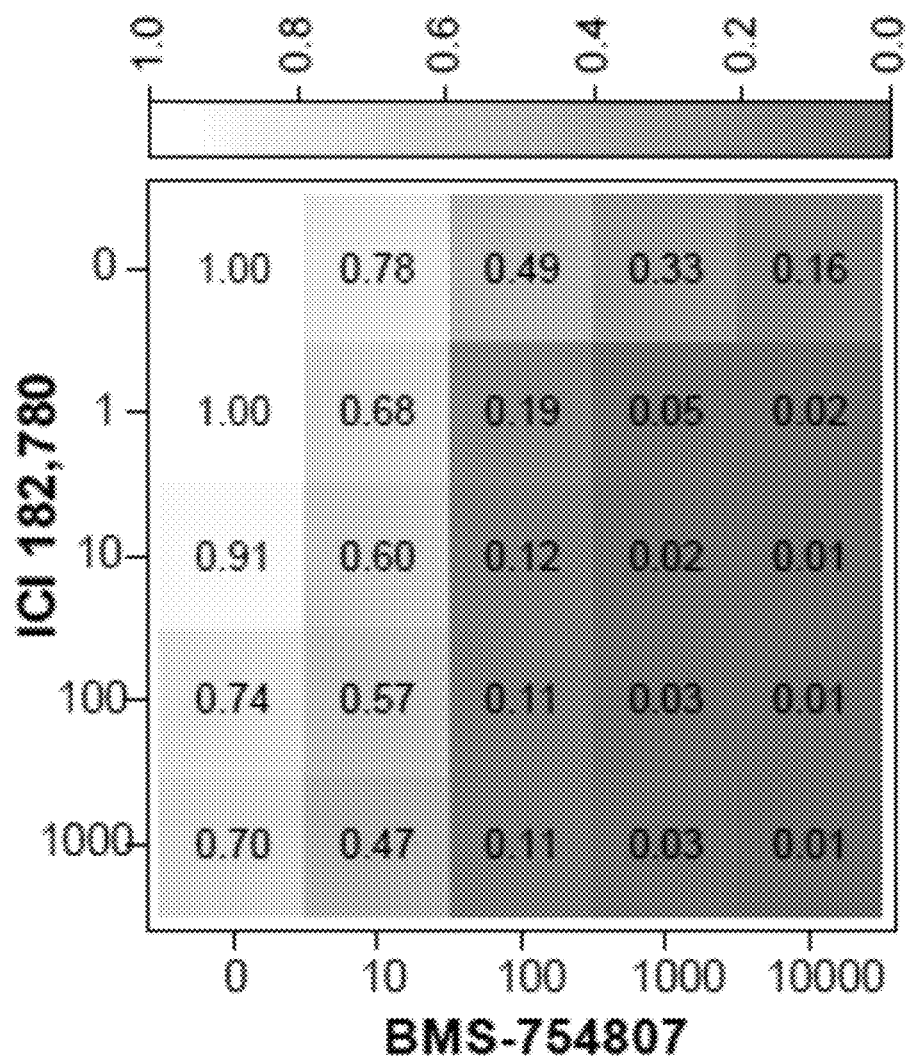
Figure 10E:
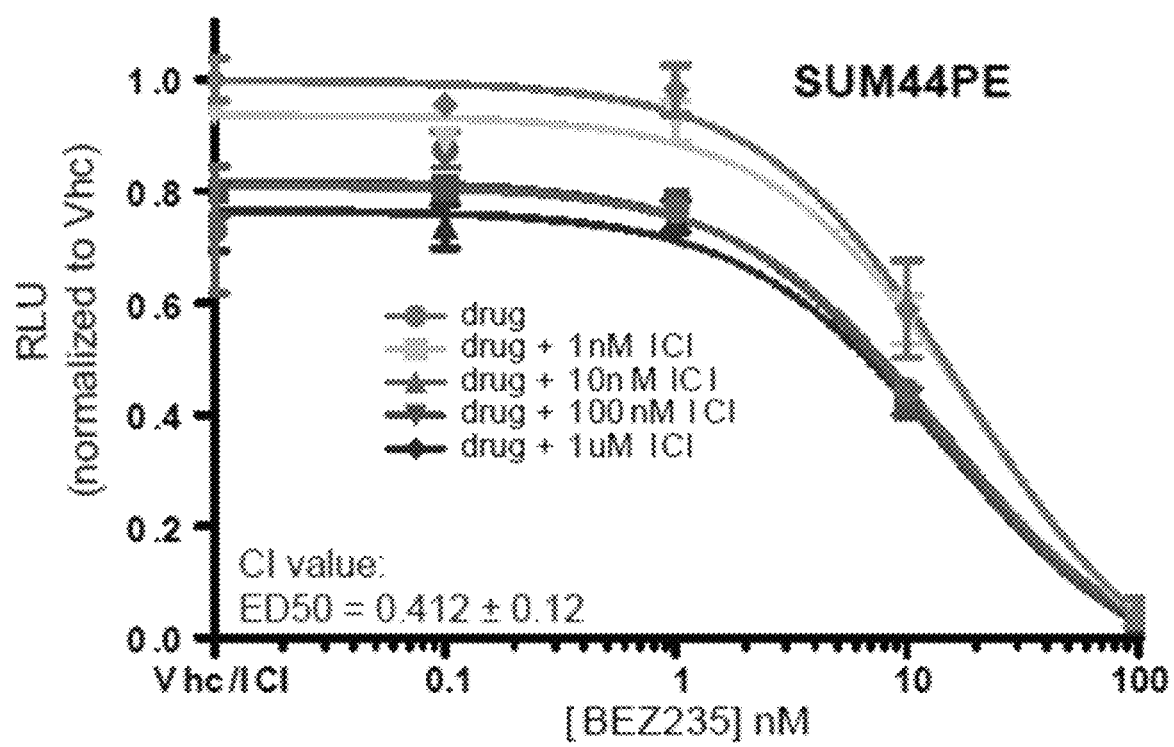
Figure 10F:
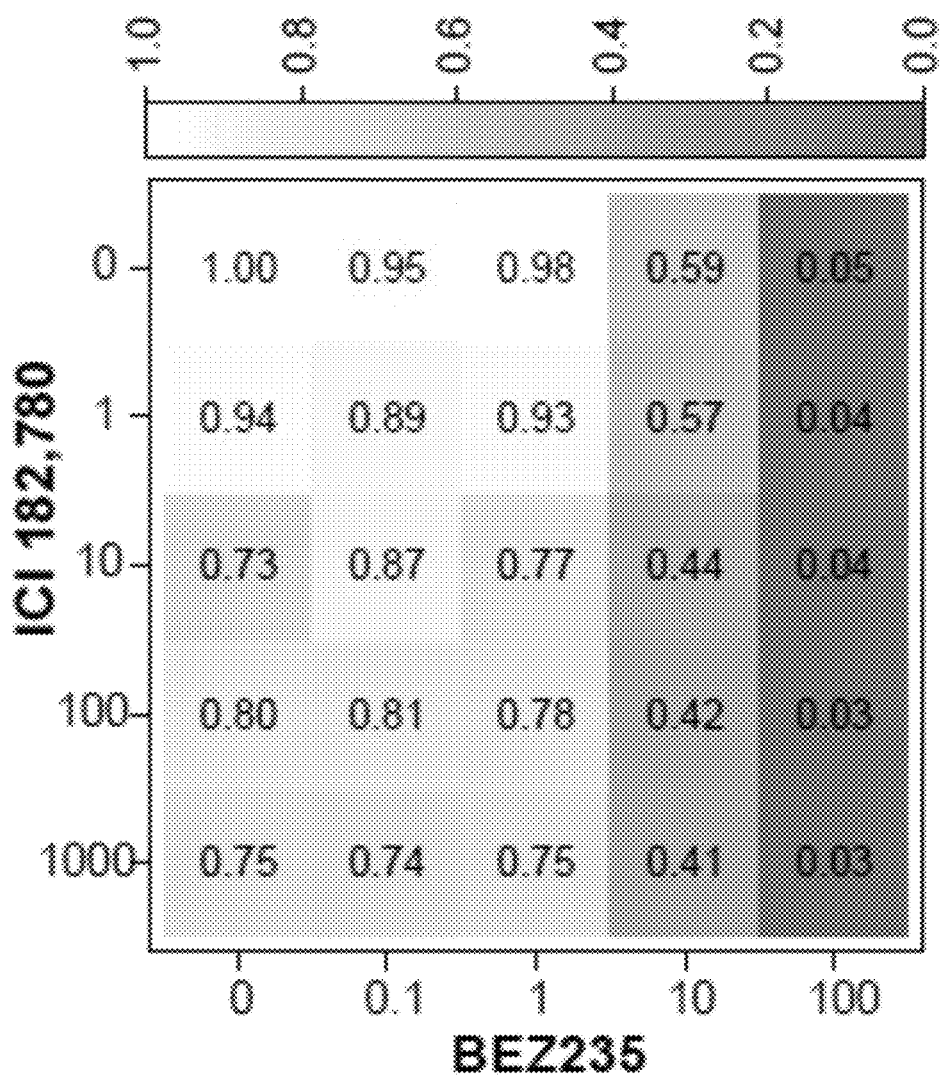

To compare IGF1R activity in ER+ ILC and IDC tumors, CDH1 and IGF1 ligand mRNA expression, and levels of phosphorylated IGF1R (pIGF1R; phosphorylation measured at tyrosines Y1135 and Y1136) were examined using RNA-sequencing and Reverse Phase Protein Array data from The Cancer Genome Atlas (TCGA). Concurrent with a decrease in CDH1 mRNA expression (p=9.06e-52; FIG. 9D), IGF1 ligand mRNA expression (p=1.3e-15; FIG. 9E) and pIGF1R levels (p=2.15e-08; FIG. 9F) were significantly increased in the ILC tumors compared to IDC tumors. Interestingly, ILC tumors exhibited a significant positive correlation between IGF1 mRNA expression and pIGF1R level (Spearman rho=0.21; p=0.012), despite having significantly reduced total IGF1R expression compared to IDC (data not shown; FIG. 9G). In contrast, IDC tumors did not show a correlation (Spearman rho=0.06; p=0.22), showing that presence of IGF1 ligand did not necessarily activate IGF1R in IDC. Strikingly, the percentage of tumors with higher than median expression (across all breast tumors) of both IGF1 and phosphorylated IGF1R (pIGF1R) is significantly higher in ILC (56.2%) compared to IDC (21.3%), showing that IGF1 ligand activates IGF1R signaling in these tumors more efficiently with the loss of E-cadherin (chi-square test, p=2.5e-14 [FIG. 9G]). Interestingly, when assessing activation of the IGF-sig in ER+ ILC versus IDC in the TCGA cohort, no difference in expression score was observed (data not shown).

IGF1R Pathway Inhibitors and Endocrine Therapy Synergize to Decrease Viability in ILC Cells.

Figure 11A:
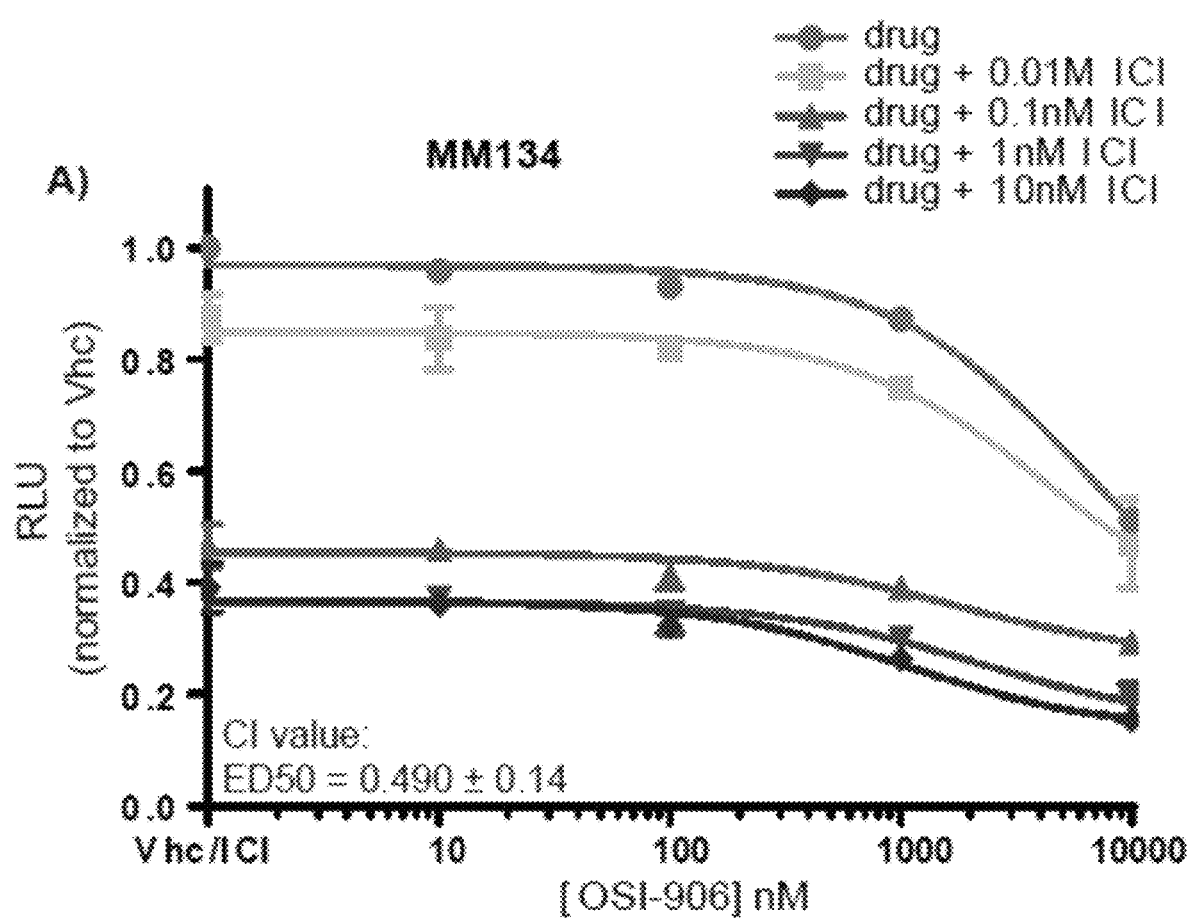
FIGS. 11A, 11B, 11C, 11D, 11E, and 11F show IGF1R pathway inhibitors and endocrine therapy synergize to inhibit cell viability in ILC breast cancer cells. MDA-MB-134 ILC cells were plated into 96-well ULA plates and treated for 6 days with increasing doses of OSI-906 (FIG. 11A, 11B), BMS-754807 (FIGS. 11C, 11D), or BEZ235 (FIGS. 11E, 11F) in combination with increasing doses of ICI 182,780. The dose response curves (FIGS. 11A, 11C, 11E) and heat maps (FIGS. 11B, 11D, 11F) shown indicate inhibition of cell viability (CellTiter Glo). Representative experiment shown; n=3 each with 2 biological replicates per combination of doses.
Figure 11B:
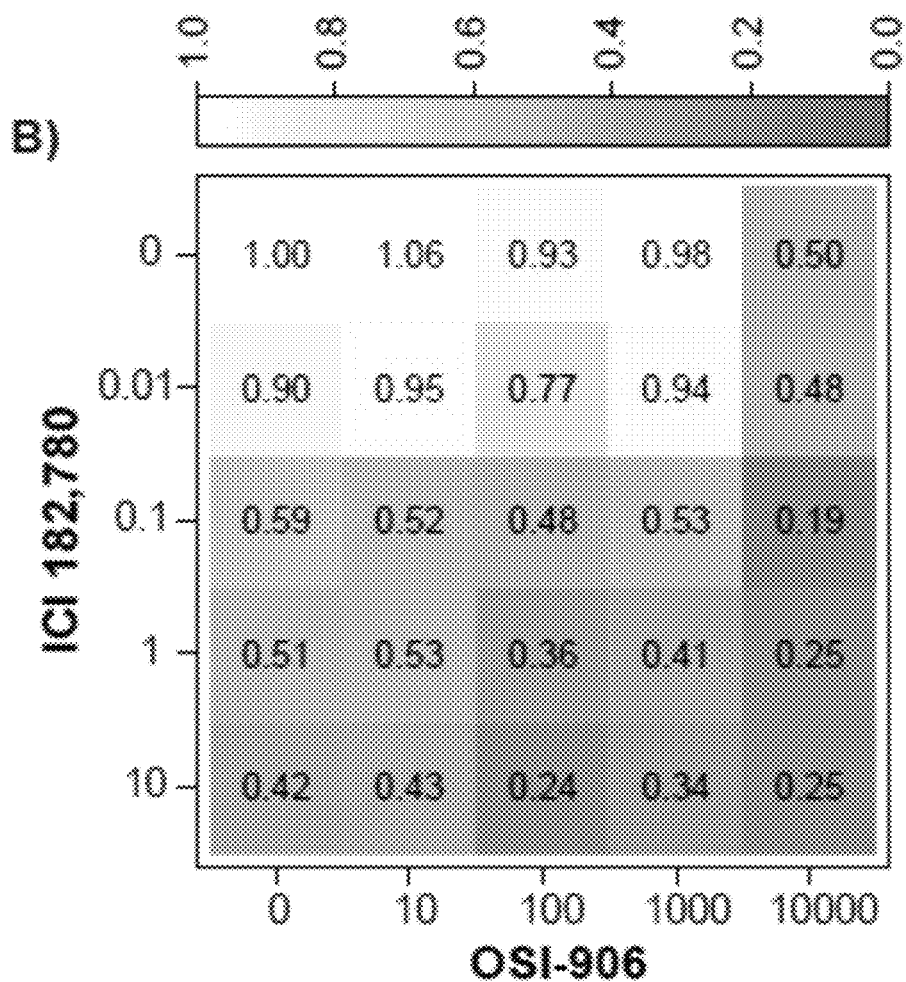
Figure 11C:
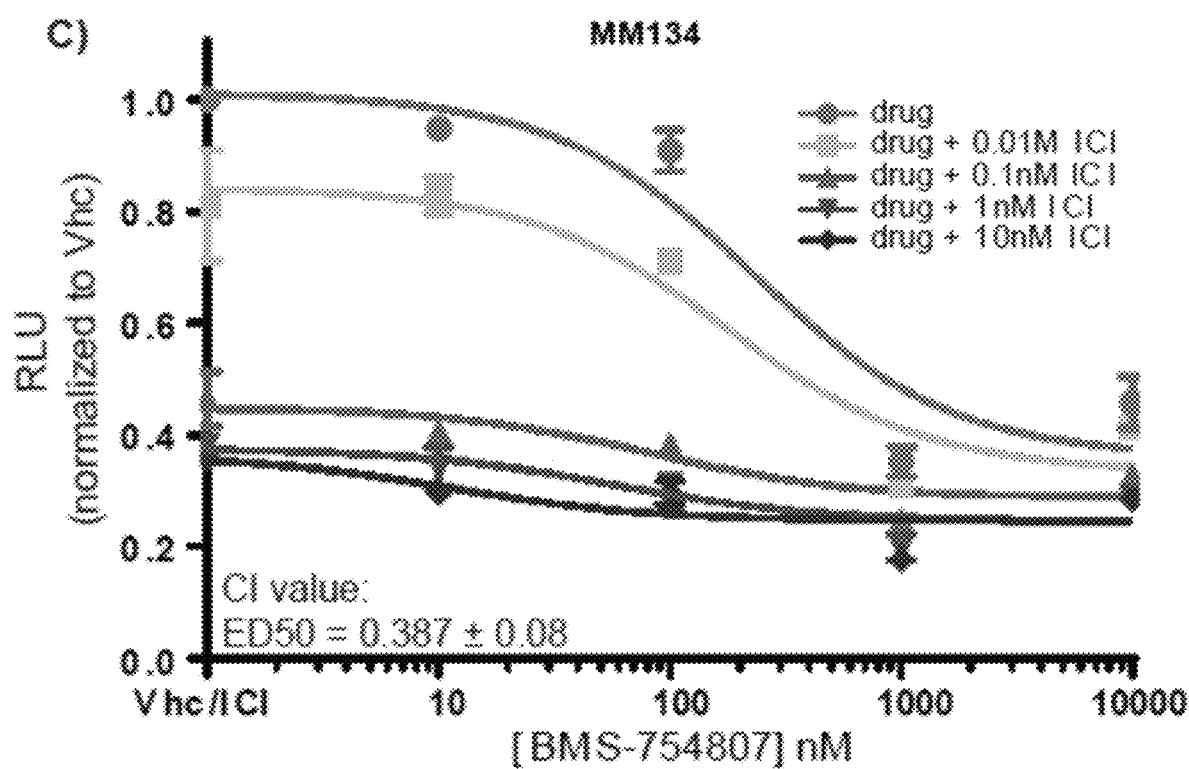
Figure 11D:
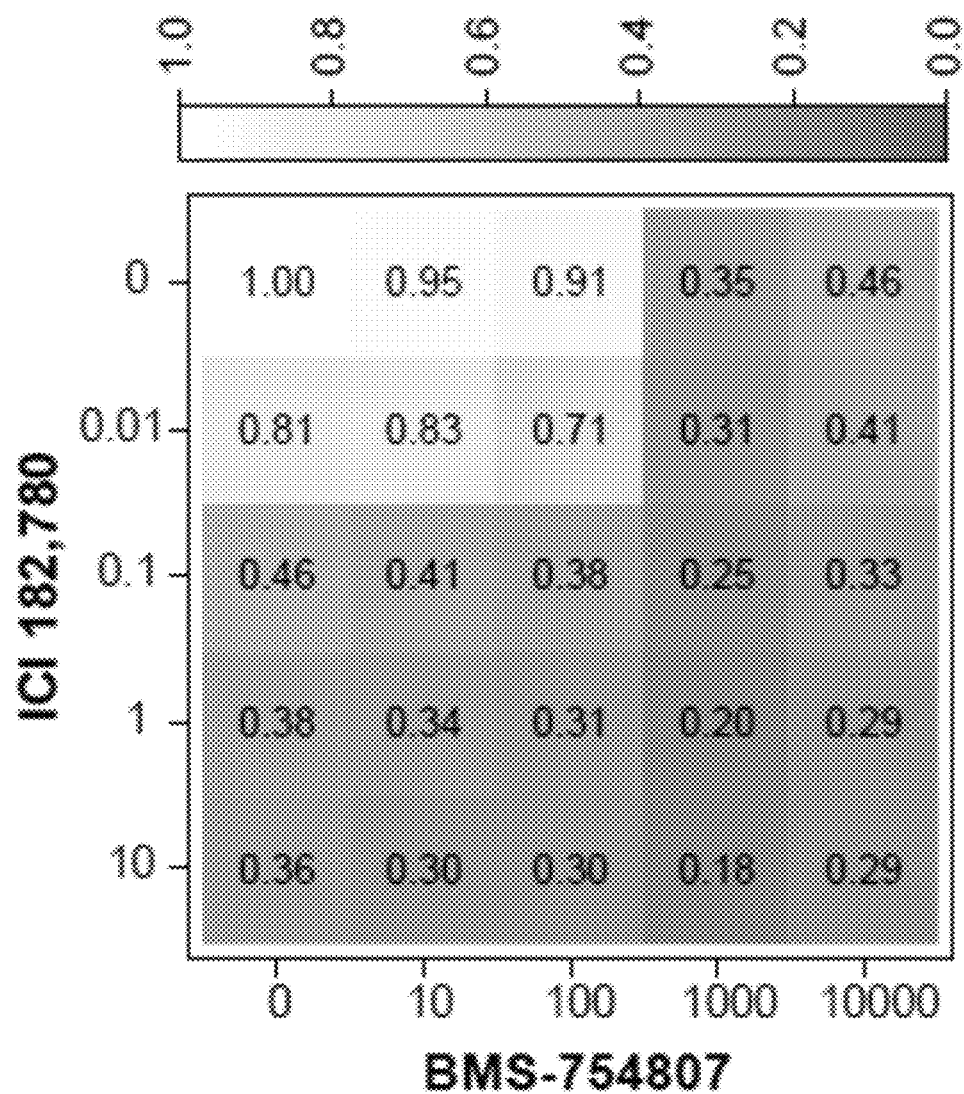
Figure 11E:
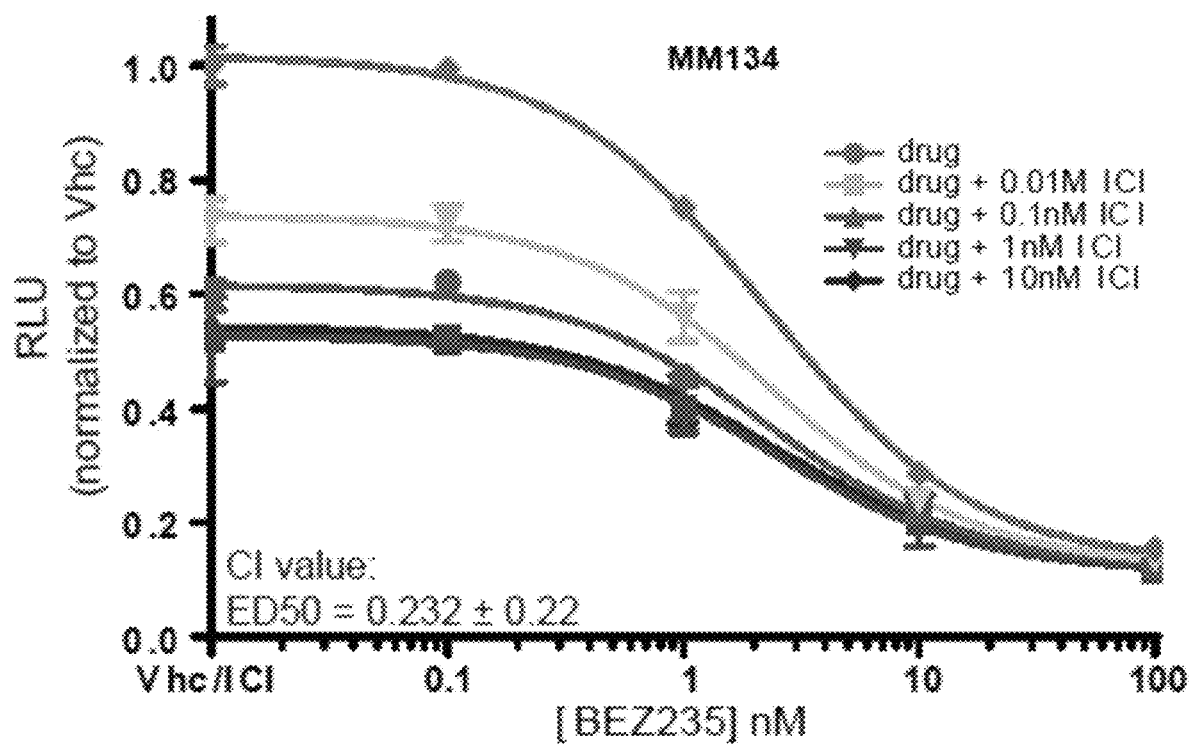
Figure 11F:
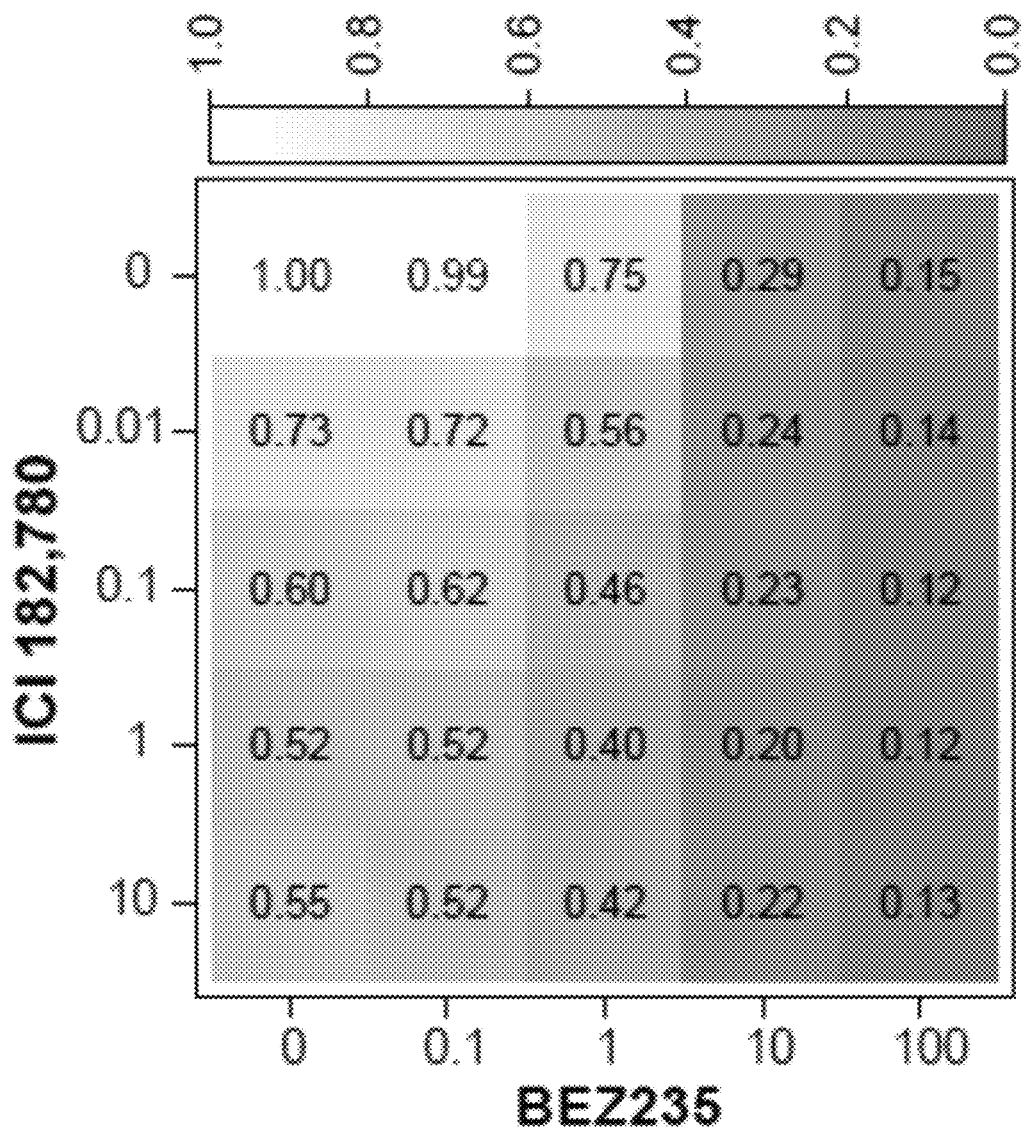

Clinically, patients with ER+ ILC are treated with endocrine therapy targeting ER. However, data from the BIG 1-98 trial showed that ILC tumors demonstrate resistance to tamoxifen, a selective estrogen receptor modulator, compared to IDC. Additionally, results from multiple clinical studies indicate that ILC patients have a poorer prognosis with more frequent late recurrences compared to IDC. This highlights the need to improve therapeutic options in ILC patients based on uniquely activated pathways. Thus, efficacy of IGF1R pathway inhibitors were evaluated in ER+ ILC cell lines in combination with endocrine therapy. Tamoxifen can act as a partial ER agonist activating ER activity in some ILC cell lines, rather than as a pure antagonist as in IDC cells, in line with BIG 1-98 results. Therefore, efficacy of the selective estrogen receptor down-regulator, ICI 182,780 (ICI), was tested in combination with the two IGF1R pathway inhibitors used in FIG. 4 (OSI and BMS) and the PI3K/mTOR inhibitor BEZ235 (BEZ). ER+ ILC cell lines SUM44PE and MM134 were treated with increasing doses of OSI (FIGS. 10A-B; FIGS. 11A-B), BMS (FIGS. 10C-D; FIGS. 11C-D), and BEZ (FIGS. 10E-F; FIGS. 11E-F) in combination with increasing doses of ICI. With all three IGF1R pathway inhibitors, decreased cell viability was observed with the addition of increasing doses of ICI. Formal synergy testing of the drug combinations using the Median-Effect Principle and Combination-Index Isobologram Theorem, commonly referred to as the Chou-Talalay method revealed combination index (CI) values less than 1 for drug interactions at the ED50, ED75, and ED90, indicating an unexpected and surprisingly high level of synergy for the three sets of inhibitor combinations (FIG. 10, FIG. 11, Table 1). The lowest CI values were observed for the BMS+ICI drug combination in SUM44PE cells (ED50=0.127, ED75=0.081, ED90=0.099). Additionally, a minimum dose reduction index (DRI) for ICI of 8-fold for all drug combinations in SUM44PE cells and 2-fold in MM134 cells at the EC50 was seen. These data show that adding an IGF1R pathway inhibitor in combination with ICI synergistically reduces the concentration of ICI necessary to achieve that same inhibitory effect as ICI alone.

TABLE 1

| Cell Line | Drug + ICI | CI: ED50 | CI: ED75 | CI: ED90 |
| --- | --- | --- | --- | --- |
| SUM44PE | OSI-906 | 0.198 ± 0.06 | 0.250 ± 0.10 | 0.398 ± 0.22 |
| SUM44PE | BMS-754807 | 0.127 ± 0.06 | 0.081 ± 0.04 | 0.099 ± 0.04 |
| SUM44PE | BEZ235 | 0.412 ± 0.12 | 0.401 ± 0.12 | 0.425 ± 0.12 |
| MM134 | OSI-906 | 0.490 ± 0.14 | 0.449 ± 0.18 | 0.808 ± 0.48 |
| MM134 | BMS-754807 | 0.387 ± 0.08 | 0.230 ± 0.04 | 0.667 ± 0.15 |
| MM134 | BEZ235 | 0.232 ± 0.22 | 0.547 ± 0.13 | 2.885 ± 1.34 |

Table 1 shows IGF1R pathway inhibitors and ICI 182,780 synergize to inhibit cell growth. Synergy was measured using the Median-Effect Principle and Combination-Index Isoblogram Theorem. The table displays the E50, ED75, and ED90 values from inhibitors OSI-906, BMS-754807, or BEZ235 in combination with ICI 182,780 in two ILC cell lines (SUM44PE and MM134). Values are shown +/−SEM from 3 independent experiments each with n=2 biological replicates. CI values <1 indicate a synergistic drug interaction.

Ex Vivo IGF1R Inhibition Inhibits Proliferation in an ILC Xenograft.

Figure 12A:
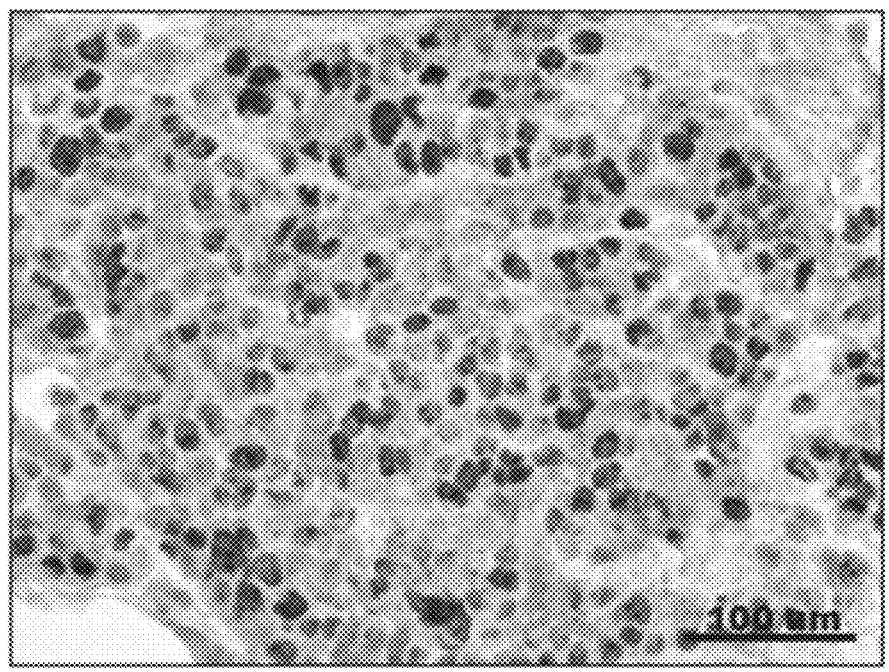
FIGS. 12A, 12B, 12C, 12D, 12E and 12F show IGF1R inhibition reduces Ki67 staining in ILC tumor ex vivo culture. MM134 (FIGS. 12A, 12B, and 12C) and BCK4 (FIGS. 12D, 12E, and 12F) xenograft tumors were harvested from immunocompromised mice, minced into 1-2 mm$^3$ tumor chunks and then plated on gelatin sponges in 12-well plate containing 1.5 mL media. Media was treated with DMSO Vhc (FIGS. 12A and 12D) or 1 µM BMS-75807 (FIGS. 12B and 12E) for 72 hours. Tumor pieces were harvested by FFPE and stained for Ki67 as a marker of proliferation. Staining was quantified for MM134 (FIG. 12C) and BCK4 (FIG. 12F) cells by counting all clearly defined nuclei in 20× images. Statistical difference was assessed using a Student's t-test (p<0.05; n=3-6).
Figure 12B:
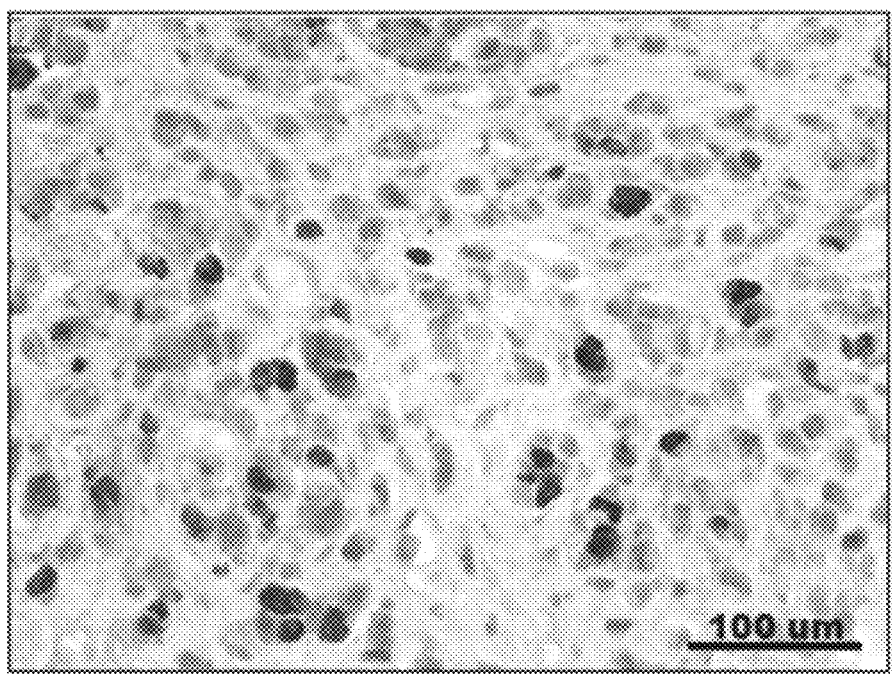
Figure 12C:
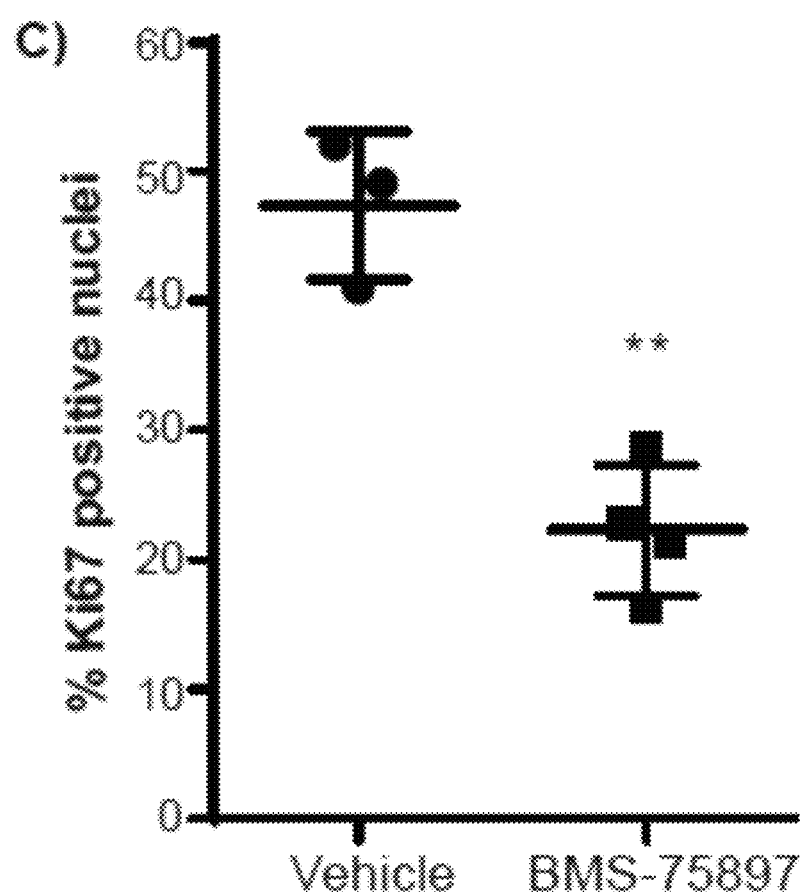
Figure 12D:
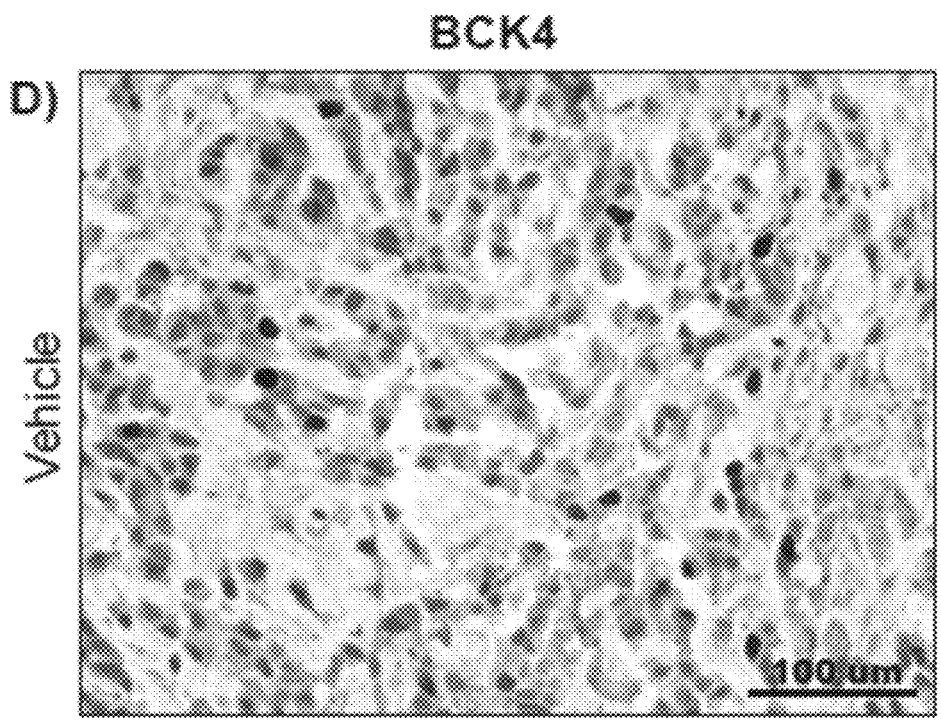
Figure 12E:
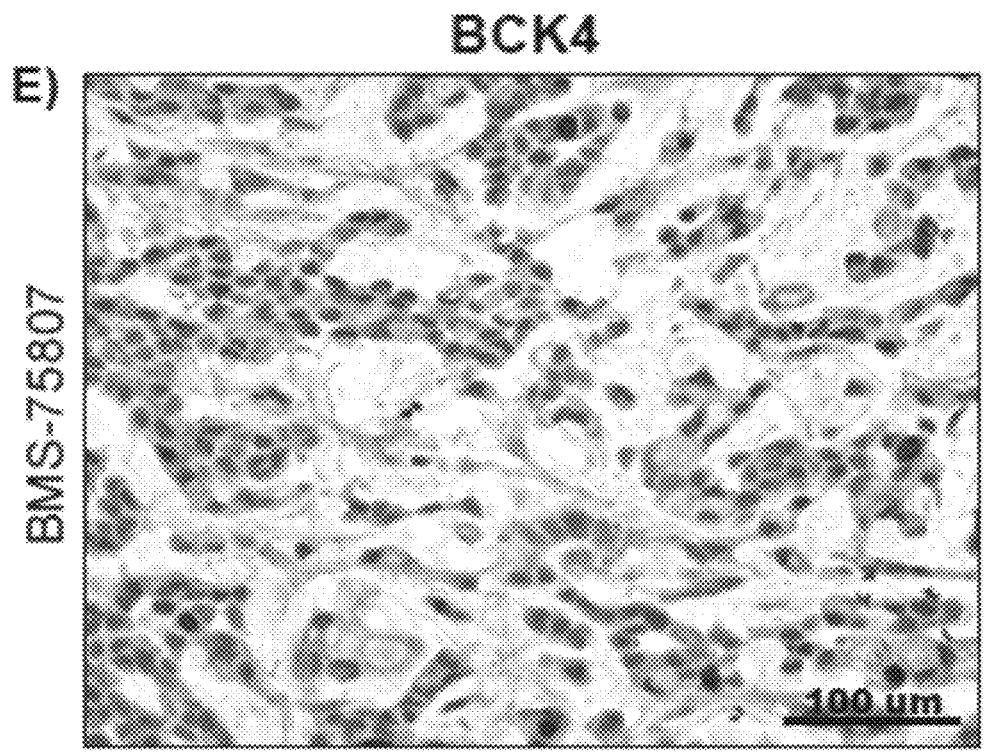
Figure 12F:
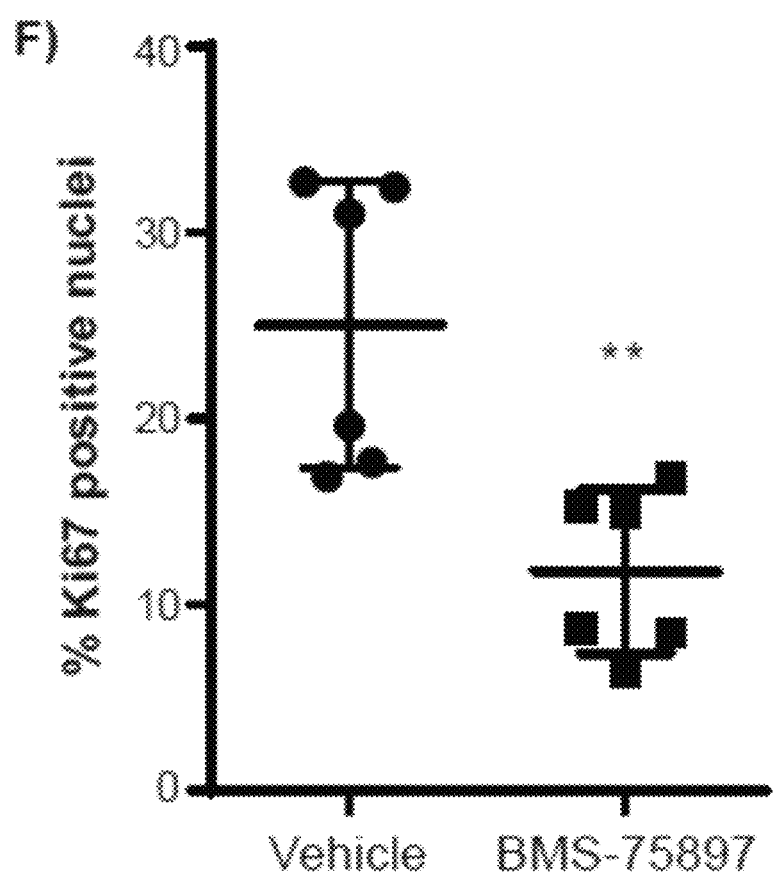

Finally, the efficacy of an IGF1R pathway inhibitor was evaluated in ILC tumors. However, there are a limited number of ILC patient-derived xenograft (PDX) and cell line xenograft models, and their slow growth rates makes large scale in vivo studies challenging. Thus, two ILC cell line xenografts were treated ex vivo as explant cultures, as previously described. The advantages of this technique include less tissue requirement for the assay compared to an in vivo study and rapid understanding of the therapeutic efficacy of the inhibitor. Additionally, there is a high concordance between ex vivo and in vivo tumor response to drug treatment. MM134 and BCK4 cells (a weakly ER responsive ILC cell line, not used for synergy experiments due to slow growth in vitro) were grown as xenografts, harvested and plated as explant culture, and treated with vehicle or BMS (1 μM) for 72 hours. The tissue was collected and stained for Ki67 as a marker of proliferation. A significant decrease occurred in Ki67 positive nuclei in both tumor models treated with BMS (FIG. 12). In the MM134 tumor, Ki67 positive nuclei significantly decreased (p=0.002) from 47% in the vehicle to 22% in the BMS treated tumor tissue (n=3 or 4; FIG. 12A-C). Similarly, in the BCK4 tumor Ki67 positive nuclei significantly decreased (p=0.005) from 25% in the vehicle to 11% in the BMS treated tumor tissue (n=6; FIG. 12D-F). These data demonstrate that targeting IGF1R in ILC tumors is a useful strategy to inhibit cell proliferation.

Discussion

Despite a large body of preclinical evidence supporting the use of IGF1R inhibitors for the treatment of breast cancer, the outcomes of clinical trials testing the efficacy of these drugs in patients thus far have been disappointing. However, these trials proceeded with a lack of appropriate biomarkers for predicting positive therapeutic efficacy and little to no understanding of which tumor types would benefit from those therapies. In response, the field has in recent years emphasized the need to understand and identify gene expression or proteomic biomarkers that predict a positive response to targeted therapy. A gene expression signature used to identify tumors that are IGF1 responsive was previously reported. In this study, investigations were focused on one protein, E-cadherin, demonstrated herein to be a proteomic biomarker for therapeutic responsiveness to IGF1R pathway inhibitors. It is known that constitutive IGF1R activation drives E-cadherin transcriptional repression through EMT, however, the reverse regulation of IGF1R by E-cadherin has not been previously characterized. This study shows that loss of E-cadherin in breast tumors, specifically in ILC, highlights a subset of tumors that are responsive to IGF1R inhibition. This study further describes the mechanisms by which this regulation occurs.

In breast cancer cells, IGF1R is endogenously localized to cell-cell contacts, similar to data published in MCF-7 cells overexpressing IGF1R and in corneal epithelial cells. A direct, endogenous interaction between IGF1R and E-cadherin is shown using in situ proximity ligation assay (PLA). PLA data clearly demonstrate this interaction using a technique having higher specificity and sensitivity compared to prior experiments such as immunoprecipitation (IP), which requires intense cell manipulation (e.g. lysis and scraping) and often results in pull-down of entire protein complexes. These results show IGF1R is likely recruited to adherens junctions by E-cadherin, possibly resulting in receptor sequestration and signaling repression. This process is similar to the sequestration of EGFR into the adherens junction and loss of receptor mobility, a well characterized mechanism of EGFR signaling repression. However, other studies suggest that the latter action is mediated through the tumor suppressor, Merlin, responsible for coordinating stabilization of the adherens junction and thereby regulating contact-inhibition growth. Although IGF1R signaling is controlled in a contact-dependent manner (FIG. 1E), other studies showed IGF1 activity is not regulated by Merlin, indicating that IGF1R regulation by E-cadherin likely occurs independent of this factor. It is shown herein that E-cadherin plays a role in coordinating the recruitment and sequestration of IGF1R within the adherens junction to repress IGF1R signaling. When E-cadherin is lost, repressed, or nonfunctional and junction formation is disrupted (such as in ILC cells), IGF1R is released and re-localizes to the entirety of the cell membrane where signaling is more easily initiated upon IGF1 ligand binding.

Supporting this concept, knockdown of E-cadherin in three ER+ breast cancer cell lines not only enhanced IGF1-induced signaling via IGF1R but also increased sensitivity of the cells to the ligand. This is similar to the relationship reported between EGF-EGFR and IGF1-IGF1R upon adherens junction disruption via calcium-depletion. Because of the increased IGF1R pathway activation associated with the loss of E-cadherin, the knockdown cells in turn became more sensitive to IGF1R inhibition.

IGF1R signaling is thus particularly important in ILC, an understudied subtype of breast cancer, due to the complete loss of E-cadherin protein and/or adherens junction formation. In this subtype, the loss of E-cadherin may serve as a biomarker of IGF1 activity. Indeed, as compared to IDC, ILC have increased IGF1R pathway activation, as shown by increased IGF1 ligand expression and phosphorylated IGF1R (pIGF1R) levels. Consistent with this, ILC cell lines are susceptible to IGF1R inhibition. Further, and very importantly and unexpectedly, IGF1R pathway inhibitors (OSI, BMS, BEZ) synergize with a standard of care endocrine therapy (ICI), resulting in further reduced cell growth. This data is especially important given that there is an increased prevalence of late recurrences in ER+ ILC compared to ER+ IDC tumors treated with endocrine therapy, highlighting the need for improved therapy options for patients with ILC.

Use of a PI3K pathway inhibitor, such as BEZ235, may be mutually beneficial in targeting both the PI3K/Akt signaling pathway, known to have a high prevalence of PIK3CA/PTEN alterations, and the enhanced IGF1R pathway activation observed in ILC tumors. Interestingly, Cantley et al. recently reported that high levels of insulin promote resistance to PI3K inhibitors in tumors with PIK3CA mutations, and therefore there may also be a role for combinatorial IGF1R and PI3K inhibition.

In summary, loss of E-cadherin enhances IGF1R pathway activity and sensitivity to IGF1R therapy, particularly in ILC. IGF1R and E-cadherin directly interact, which leads to sequestration and potential repression of IGF1R within the adherens junction. Overall, this study demonstrates a therapeutic strategy of exploiting IGF1R pathway activity in ILC tumors and describes the mechanism of IGF1R regulation by E-cadherin.

REFERENCES

1. Pollak, M. N. Insulin-like growth factors and neoplasia. *Nat. Rev. Cancer* 262, 84-107-268 (2004).
2. Becker, M. a, Ibrahim, Y. H., Cui, X., Lee, A. V & Yee, D. The IGF pathway regulates ERα through a S6K1-dependent mechanism in breast cancer cells. *Mol. Endocrinol.* 25, 516-28 (2011).
3. Hawsawi, Y., El-Gendy, R., Twelves, C., Speirs, V. & Beattie, J. Insulin-like growth factor—oestradiol crosstalk and mammary gland tumourigenesis. *Biochim. Biophys. Acta* 1836, 345-53 (2013).
4. Yee, D. & Lee, A. V. Crosstalk between the insulin-like growth factors and estrogens in breast cancer. *J. Mammary Gland Biol. Neoplasia* 5, 107-15 (2000).
5. Baserga, R., Peruzzi, F. & Reiss, K. The IGF-1 receptor in cancer biology. *Int. J. Cancer* 107, 873-877 (2003).
6. Kim, H.-J. et al. Constitutively active type I insulin-like growth factor receptor causes transformation and xenograft growth of immortalized mammary epithelial cells and is accompanied by an epithelial-to-mesenchymal transition mediated by NF-kappaB and snail. *Mol. Cell. Biol.* 27, 3165-75 (2007).
7. Litzenburger, B. C. et al. BMS-536924 Reverses IGF-IR-induced Transformation of Mammary Epithelial Cells and Causes Growth Inhibition and Polarization of MCF7 Cells. *Clin Cancer Res* 15, 1-23 (2009).
8. Carboni, J. M. et al. Tumor Development by Transgenic Expression of a Constitutively Active Insulin-Like Growth Factor I Receptor. 3781-3788 (2005).
9. Sachdev, D., Hartell, J. S., Lee, A. V, Zhang, X. & Yee, D. A Dominant Negative Type I Insulin-like Growth Factor Receptor Inhibits Metastasis of Human Cancer Cells. *J. Biol. Chem.* 279, 5017-5024 (2004).
10. Cox, 0. T. et al. IGF-1 Receptor and Adhesion Signaling: An Important Axis in Determining Cancer Cell Phenotype and Therapy Resistance. *Front. Endocrinol.* (*Lausanne*). 6, 106 (2015).
11. Farabaugh, S. M., Boone, D. N. & Lee, A. V. Role of IGF1R in Breast Cancer Subtypes, Stemness, and Lineage Differentiation. *Front. Endocrinol.* (*Lausanne*). 6, 59 (2015).
12. Crudden, C., Girnita, A. & Girnita, L. Targeting the IGF-1R: The Tale of the Tortoise and the Hare. *Front. Endocrinol.* (*Lausanne*). 6, 64 (2015).
13. Boone, D. N. & Lee, A. V. Targeting the Insulin-like Growth Factor Receptor: Developing Biomarkers from Gene Expression Profiling. *Crit Rev Oncog* 17, 161-173 (2012).

14. Singh, P., Alex, J. M. & Bast, F. Insulin receptor (IR) and insulin-like growth factor receptor 1 (IGF-1R) signaling systems: novel treatment strategies for cancer. *Med. Oncol.* 31, 805 (2014).
15. Ekyalongo, R. C. & Yee, D. Revisiting the IGF-1R as a breast cancer target. *npj Precis. Oncol.* 1, 14 (2017).
16. Creighton, C. J. et al. Insulin-like growth factor-I activates gene transcription programs strongly associated with poor breast cancer prognosis. *J. Clin. Oncol.* 26, 4078-85 (2008).
17. Erdem, C. et al. Proteomic Screening and Lasso Regression Reveal Differential Signaling in Insulin and Insulin-like Growth Factor I (IGF1) Pathways. *Mol. Cell. Proteomics* 15, 3045-3057 (2016).
18. Onder, T. T. et al. Loss of E-cadherin promotes metastasis via multiple downstream transcriptional pathways. *Cancer Res.* 68, 3645-3654 (2008).
19. Hanahan, D. & Weinberg, R. A. Hallmarks of cancer: The next generation. *Cell* 144, 646-674 (2011).
20. Mauro, L. et al. Role of the IGF-I receptor in the regulation of cell-cell adhesion: Implications in cancer development and progression. *J. Cell. Physiol.* 194, 108-116 (2003).
21. Friedl, P. & Alexander, S. Cancer invasion and the microenvironment: Plasticity and reciprocity. *Cell* 147, 992-1009 (2011).
22. Roxanis, I. Occurrence and significance of epithelial-mesenchymal transition in breast cancer. *J. Clin. Pathol.* 66, 517-21 (2013).
23. Ciriello, G. et al. Comprehensive Molecular Portraits of Invasive Lobular Breast Cancer. *Cell* 163, 506-519 (2015).
24. Barroso-Sousa, R. & Metzger-Filho, O. Differences between invasive lobular and invasive ductal carcinoma of the breast: results and therapeutic implications. *Ther. Adv. Med. Oncol.* 8, 261-266 (2016).
25. Rakha, E. A. et al. Clinical and biological significance of E-cadherin protein expression in invasive lobular carcinoma of the breast. *Am J Surg Pathol* 34, 1472-1479 (2010).
26. Jambal, P. et al. Estrogen switches pure mucinous breast cancer to invasive lobular carcinoma with mucinous features. *Breast Cancer Res. Treat.* 137, 431-448 (2013).
27. Chou, T. C. & Talalay, P. Quantitative analysis of dose-effect relationships: the combined effects of multiple drugs or enzyme inhibitors. *Adv. Enzyme Regul.* 22, 27-55 (1984).
28. Derksen, P. W. B. et al. Somatic inactivation of E-cadherin and p53 in mice leads to metastatic lobular mammary carcinoma through induction of anoikis resistance and angiogenesis. *Cancer Cell* 10, 437-449 (2006).
29. Filho, O. M. et al. Relative effectiveness of letrozole compared with tamoxifen for patients with lobular carcinoma in the BIG 1-98 Trial. *J. Clin. Oncol.* 33, 2772-2778 (2015).
30. Pestalozzi, B. C. et al. Distinct clinical and prognostic features of infiltrating lobular carcinoma of the breast: Combined results of 15 International Breast Cancer Study Group clinical trials. *J. Clin. Oncol.* 26, 3006-3014 (2008).
31. Chen, Z. et al. Invasive lobular carcinoma of the breast: A special histological type compared with invasive ductal carcinoma. *PLoS One* 12, 1-17 (2017).
32. Adachi, Y. et al. Comparison of clinical outcomes between luminal invasive ductal carcinoma and luminal invasive lobular carcinoma. *BMC Cancer* 16, 1-9 (2016).
33. Sikora, M. J. et al. Invasive lobular carcinoma cell lines are characterized by unique estrogen-mediated gene expression patterns and altered tamoxifen response. *Cancer Res.* 74, 1463-1474 (2014).
34. Andersen, C. L. et al. Active estrogen receptor-alpha signaling in ovarian cancer models and clinical specimens. *Clin. Cancer Res.* clincanres.1501.2016 (2017). doi:10.1158/1078-0432.CCR-16-1501
35. Centenera, M. M., Raj, G. V, Knudsen, K. E., Tilley, W. D. & Butler, L. M. Ex vivo culture of human prostate tissue and drug development. *Nat. Rev. Urol.* 10, 483-487 (2013).
36. Dean, J. L. et al. Therapeutic response to CDK4/6 inhibition in breast cancer defined by ex vivo analyses of human tumors. *Cell Cycle* 11, 2756-2761 (2012).
37. Majumder, B. et al. Predicting clinical response to anticancer drugs using an ex vivo platform that captures tumour heterogeneity. *Nat. Commun.* 6, 6169 (2015).
38. Gualberto, a & Pollak, M. Emerging role of insulin-like growth factor receptor inhibitors in oncology: early clinical trial results and future directions. *Oncogene* 28, 3009-3021 (2009).
39. Guvakova, M. a & Surmacz, E. Overexpressed IGF-I receptors reduce estrogen growth requirements, enhance survival, and promote E-cadherin-mediated cell-cell adhesion in human breast cancer cells. *Exp. Cell Res.* 231, 149-62 (1997).
40. Robertson, D. M., Zhu, M. & Wu, Y.-C. Cellular distribution of the IGF-1R in corneal epithelial cells. *Exp. Eye Res.* 94, 179-86 (2012).
41. Qian, X., Karpova, T., Sheppard, A. M., McNally, J. & Lowy, D. R. E-cadherin-mediated adhesion inhibits ligand-dependent activation of diverse receptor tyrosine kinases. *EMBO J.* 23, 1739-1784 (2004).
42. de-Freitas-Junior, J. C. M. et al. Insulin/IGF-I Signaling Pathways Enhances Tumor Cell Invasion through Bisecting GlcNAc N-glycans Modulation. An Interplay with E-Cadherin. *PLoS One* 8, e81579 (2013).
43. Curto, M., Cole, B. K., Lallemand, D., Liu, C. H. & McClatchey, A. I. Contact-dependent inhibition of EGFR signaling by Nf2/Merlin. *J. Cell Biol.* 177, 893-903 (2007).
44. Nakagawa, S. et al. Tumor microenvironment in invasive lobular carcinoma: possible therapeutic targets. *Breast Cancer Res. Treat.* 155, 65-75 (2016).
45. Bertucci, F. et al. Lobular and ductal carcinomas of the breast have distinct genomic and expression profiles. *Oncogene* 27, 5359-5372 (2008).
46. Shah, V. et al. PIK3CA mutations are common in lobular carcinoma in situ, but are not a biomarker of progression. *Breast Cancer Res.* 19, 7 (2017).
47. Wang, L. et al. PI3K pathway activation results in low efficacy of both trastuzumab and lapatinib. *BMC Cancer* 11, 11:248 (2011).
48. Lewis Cantley. PI 3-kinase links obesity, insulin resistance, and cancer. in (AACR-NCI-EORTC Molecular Targets and Cancer Therapeutics Meeting, 2017).

Example 2. Sequences

```
An E-cadherin amino acid sequence..
SEQ ID NO: 1
MGPWSRSLSALLLLLQVSSWLCQEPEPCHPGFDAESYTFTVPRRHLERGRVLGRVN

FEDCTGRQRTAYFSLDTRFKVGTDGVITVKRPLRFHNPQIHFLVYAWDSTYRKFST

KVTLNTVGHEIHRPPPHQASVSGIQAELLTFPNSSPGLRRQKRDWVIPPISCPENEKG

PFPKNLVQIKSNKDKEGKVFYSITGQGADTPPVGVFBERETGWLKVTEPLDRERIAT

YTLFSHAVSSNGNAVEDPMEILITVTDQNDNKPEFTQEVFKGSVMEGALPGTSVME

VTATDADDDVNTYNAAIAYTILSQDPELPDKNMFTINRNTGVISVVTTGLDRESFPT

YTLVVQAADLQGEGLSTTATAVITVTDTNDNPPIFNPTTYKGQVPENEANVVITTLK

VTDADAPNTPAWEAVYTILNDDGGQFVVTTNPVNNDGILKTAKGLDFEAKQQYIL

HVAVTNVVPFEVSLTTSTATVTVDVLDVNEAPIFVPPEKRVEVSEDFGVGQEITSYT

AQEPDTFMEQKITYRIWRDTANWLEINPDTGAISTRAELDREDFEHVKNSTYTALII

ATDNGSPVATGTGTLLLILSDVNDNAPIPEPRTIFFCERNPKPQVINIIDADLPPNTSPF

TAELTHGASANWTIQYNDPTQESIILKPKMALEVGDYKINLKLMDNQNKDQVTTLE

VSVCDCEGAAGVCRKAQPVEAGLQIPAILGILGGILALLILILLLLLFLRRRAVVKEP

LLPPEDDTRDNVYYYDEEGGGEEDQDFDLSQLHRGLDARPEVTRNDVAPTLMSVP

RYLPRPANPDEIGNFIDENLKAADTDPTAPPYDSLLVFDYEGSGSEAASLSSLNSSES

DKDQDYDYLNEWGNRFKKLADMYGGGEDD

An E-cadherin (cdh1) nucleic acid sequence..
                                              SEQ ID NO: 2
GGAAAGCACCTGTGAGCTTGGCAAGTCAGTTCAGAGCTCCAGCCCGCTCCAGCC

CGGCCCGACCCGACCGCACCCGGCGCCTGCCTCGCTCGGGCTCCCCGGCCAGCC

ATGGGCCCTTGGAGCCGCAGCCTCTCGGGCCTGCTGCTGCTGCTGAGGTCTCCT

CTTGGCTCTCAGGAGCGGAGCCCTCCTCCCTGTTTGACGCGAGAGCTACACGTT

CACGGTGCCCCGGCGCCACCTGAGAAGAGGCCGCGTCTGGGCAGAGTGAATTT

TGAAGATTGCACCGGTCGACAAAGGACAGCTATTTTCCTGACACCGATTCCGAA

AGTGGGCACAGATGGTGTGATTACAGTCAAAAGGCCTCTACGGTTTCATAACCC

AACAGATCCATTTCTTGGTCTACGCTGGGACTCCACCTACAGAAAGTTTTCCAC

CAAAGTCACGCTGAATACAGTGGGGCACCACCACCGCCCCCCGCCCCATCAGG

CCTCCGTTTCTGGAATCCAAGCAGAATTGCTCACATTTCCCAACTCCTCTCCTGG

CCTCAGAAGACAGAAGAGAGACTGGGTTATTCCTCCCATCAGCTGCCCAGAAA

ATGAAAAAGGCCCATTTCCTAAAAACCTGGTTCAGATCAAATCCAACAAAGAC

AAAGAAGGCAAGGTTTTCTACAGCATCACTGGCCAAGGAGCTGACACACCCCC

TGTTGGTGTCTTTATTATTGAAAGAGAAACAGGATGGCTGAAGGTGACAGAGCC

TCTGGATAGAGAACGCATTGCCACATACACTCTCTTCTCTCACGCTGTGTCATCC

AACGGGAATGCAGTTGAGGATCCAATGGAGATTTTGATCACGGTAACCGATCA

GAATGACAACAAGCCCGAATTCACCCAGGAGGTCTTTAAGGGGTCTGTCATGG

AAGGTGCTCTTCCAGGAACCTCTGTGATGGAGGTCACAGCCACAGACGCGGAC

GATGATGTGAACACCTACAATGCCGCCATCGCTTACACCATCCTCAGCCAAGAT

CCTGAGCTCCCTGACAAAAATATGTTCACCATTAACAGGAACACAGGAGTCATC

AGTGTGGTCACCACTGGGCTGGACCGAGAGAGTTTCCCTACGTATACCCTGGTG
```

-continued
```
GTTCAAGCTGCTGACCTTCAAGGTGAGGGGTTAAGCACAACAGCAACAGCTGT
GATCACAGTCACTGACACCAACGATAATCCTCCGATCTTCAATCCCACCACGTA
CAAGGGTCAGGTGCCTGAGAACGAGGCTAACGTCGTAATCACCACACTGAAAG
TGACTGATGCTGATGCCCCCAATACCCCAGCGTGGGAGGCTGTATACACCATAT
TGAATGATGATGGTGGACAATTTGTCGTCACCACAAATCCAGTGAACAACGATG
GCATTTTGAAAACAGCAAAGGGCTTGGATTTTGAGGCCAAGCAGCAGTACATTC
TACACGTAGCAGTGACGAATGTGGTACCTTTTGAGGTCTCTCTCACCACCTCCA
CAGCCACCGTCACCGTGGATGTGCTGGATGTGAATGAAGGCCCCATCTTTGTGC
CTCCTGAAAAGAGAGTGGAAGTGTCCGAGGACTTTGGCGTGGGCCAGGAAATC
ACATCCTACACTGCCCAGGAGCCAGACACATTTATGGAACAGAAAATAACATA
TCGGATTTGGAGAGACACTCGCAACTGGCTGGAGATTAATCCGGACACTGGTGC
CATTTCCACTCGGGCTGAGCTGGACAGGGAGGATTTTGAGCACGTGAAGAACA
GCACGTACACAGCCCTAATCATAGCTACAGACAATGGTTCTCCAGTTGCTACTG
GAACAGGGACACTTCTGCTGATCCTGTCTGATGTGAATGACAACGCCCCCATAC
CAGAACCTCGAACTATATTCTTCTGTGAGAGGAATCCAAAGCCTCAGGTCATAA
ACATTCATGATGCAGACCTTCCTCCCAATACATCTCCCTTCACAGCAGAACTAA
CACACGGGCGAGTGCCCAACTGGACCATTCAGTACAACGACCCAACCCAAGAA
TCTATCATTTTGAAGCCAAAGATGGCCTTAGAGGTGGGTGACTACAAAATCAAT
CTCAAGCTCATGGATAACCAGAATAAAGACCAAGTGACCACCTTAGAGGTCAG
CGTGTGTGACTGTGAAGGGGCCGCCGGCGTCTGTAGGAAGGCACAGCCTGTCG
AAGCAGGATTGCAAATTCCTGCCATTCTGGGGATTCTTGGAGGAATTCTTGCTT
TGCTAATTCTGATTCTGCTGCTCTTGCTGTTTCTTCGGAGGAGAGCGGTGGTCAA
AGAGCCCTTACTGCCCCCAGAGGATGACACCCGGGACAACGTTTATTACTATGA
TGAAGAAGGAGGCGGAGAAGAGGACCAGGACTTTGACTTGAGCCAGCTGCACA
GGGGCCTGGACGCTCGGCCTGAAGTGACTCGTAACGACGTTGCACCAACCCTCA
TGAGTGTCCCCCGGTATCTTCCCCGCCCTGCCAATCCCGATGAAATTGGAAATT
TTATTGATGAAAATCTGAAAGCGGCTGATACTGACCCCACAGCCCCGCCTTATG
ATTCTCTGCTCGTGTTTGACTATGAAGGAAGCGGTTCCGAAGCTGCTAGTCTGA
GCTCCCTGAACTCCTCAGAGTCAGACAAAGACCAGGACTATGACTACTTGAACG
AATGGGGCAATCCGTTCAAGAAGCTGGCTGACATGTACGGAGGCGGCGAGGAC
CACTAGGGGACTCGAGAGAGGCGGCCCAGACCATGTGCAGAAATGCAGAAATC
AGCGTTCTGGTGTTTT
```
An IGFR1 amino acid sequence.. SEQ ID NO: 3
```
MKSGSGGGSP TSLWGLLFLS AALSLWPTSG EICGPGIDIR NDYQQLKRLE
NCTVIEGYLH ILLISKAEDY RSYRFPKLTV ITEYLLLFRV AGLESLGDLF
PNLTVIRGWK LFYNYALVIF EMTNLKDIGL YNLRNITRGA IRIEKNADLC
YLSTVDWSLI LDAVSNNYIV GNKPPKECGD LCPGTMEEKP MCEKTTINNE
YNYRCWTTNR CQKMCPSTCG KRACTENNEC CHPECLGSCS APDNDTACVA
CRHYYYAGVC VPACPPNTYR FEGWRCVDRD FCANILSAES SDSEGFVIHD
GECMQECPSG FIRNGSQSMY CIPCEGPCPK VCEEEKKTKT IDSVTSAQML
QGCTIFKGNL LINIRRGNNI ASELENFMGL IEVVTGYVKI RHSHALVSLS
```

-continued

```
FLKNLRLILG EEQLEGNYSF YVLDNQNLQQ LWDWDHRNLT IKAGKMYFAF

NPKLCVSEIY RMEEVTGTKG RQSKGDINTR NNGERASCES DVLHFTSTTT

SKNRIIITWH RYRPPDYRDL ISFTVYYKEA PFKNVTEYDG QDACGSNSWN

MVDVDLPPNK DVEPGILLHG LKPWTQYAVY VKAVTLTMVE NDHIRGAKSE

ILYIRTNASV PSIPLDVLSA SNSSSQLIVK WNPPSLPNGN LSYYIVRWQR

QPQDGYLYRH NYCSKDKIPI RKYADGTIDI EEVTENPKTE VCGGEKGPCC

ACPKTEAEKQ AEKEEAEYRK VFENFLHNSI FVPRPERKRR DVMQVANTTM

SSRSRNTTAA DTYNITDPEE LETEYPFFES RVDNKERTVI SNLRPFTLYR

IDIHSCNHEA EKLGCSASNF VFARTMPAEG ADDIPGPVTW EPRPENSIFL

KWPEPENPNG LILMYEIKYG SQVEDQRECV SRQEYRKYGG AKLNRLNPGN

YTARIQATSL SGNGSWTDPV FFYVQAKTGY ENFIHLIIAL PVAVLLIVGG

LVIMLYVFHR KRNNSRLGNG VLYASVNPEY FSAADVYVPD EWEVAREKIT

MSRELGQGSF GMVYEGVAKG VVKDEPETRV AIKTVNEAAS MRERIEFLNE

ASVMKEFNCH HVVRLLGVVS QGQPTLVIME LMTRGDLKSY LRSLRPEMEN

NPVLAPPSLS KMIQMAGEIA DGMAYLNANK FVHRDLAARN CMVAEDFTVK

IGDFGMTRDI YETDYYRKGG KGLLPVRWMS PESLKDGVFT TYSDVWSFGV

VLWEIATLAE QPYQGLSNEQ VLRFVMEGGL LDKPDNCPDM LFELMRMCWQ

YNPKMRPSFL EIISSIKEEM EPGFREVSFY YSEENKLPEP EELDLEPENM

ESVPLDPSAS SSSLPLPDRH SGHKAENGPG PGVLVLRASF DERQPYAHMN

GGRKNERALP LPQSSTC

A control short hairpin RNA (shRNA) sequence..
                                                          SEQ ID NO: 4
5' TGCTGTTGACAGTGAGCGCAGGAATTATAATGCTTATCTATAGTGAAGCCACA
GATGTATAGATAAGCATTATAATTCCTATGCCTACTGCCTCGGA An anti-cdh1 shRNA sequence..
                                                          SEQ ID NO: 5
5' TGCTGTTGACAGTGAGCGCAAGTGTGTTCATTAATGTTTATAGTGAAGCC
ACAGATGTATAAACATTAATGAACACACTTATGCCTACTGCCTCGGA An anti-cdh1 shRNA sequence..
                                                          SEQ ID NO: 6
5' TGCTGTTGACAGTGAGCGACCGGGACAACGTTTATTACTATAGTGAAGCCAC
AGATGTATAGTAATAAACGTTGTCCCGGGTGCCTACTGCCTCGGA
```

Publications cited herein are hereby specifically incorporated by reference in their entireties and at least for the material for which they are cited.

It should be understood that while the present disclosure has been provided in detail with respect to certain illustrative and specific aspects thereof, it should not be considered limited to such, as numerous modifications are possible without departing from the broad spirit and scope of the present disclosure as defined in the appended claims. It is, therefore, intended that the appended claims cover all such equivalent variations as fall within the true spirit and scope of the invention.

What is claimed is:

1. A method of treating a subject with a cancer comprising:
   a) obtaining a sample of the cancer from the subject;
   b) determining a level of E-cadherin in the sample is reduced compared to a control; and
   c) administering a therapeutically effective amount of an IGF1R pathway inhibitor and an endocrine therapeutic.

2. The method of claim 1, wherein the cancer comprises an estrogen receptor-positive (ER+) breast cancer.

3. The method of claim 2, wherein the control comprises one or more non-cancerous mammary epithelial cells of the subject.

4. The method of claim 2, wherein the ER+ breast cancer comprises an invasive lobular breast cancer (ILC).

5. The method of claim 1, wherein the IGF1R pathway inhibitor comprises MEDI-573, OSI-906, BMS-754807, BEZ235, xentuzumab, or a combination thereof.

6. The method of claim 1, wherein the endocrine therapeutic comprises tamoxifen, ICI 182,780, or a combination thereof.

7. The method of claim 1, wherein the level of E-cadherin is reduced by at least 50% compared to the control.

8. The method of claim 1, wherein the determining step comprises determining a level of E-cadherin polypeptide expression.

9. A method of treating a cancer in a subject comprising administering a therapeutically effective amount of an IGF1R pathway inhibitor and an E-cadherin inhibitor.

10. The method of claim 9, wherein the cancer in the subject comprises a level of E-cadherin which is not reduced compared to a control.

11. The method of claim 9, wherein the IGF1R pathway inhibitor comprises MEDI-573, OSI-906, BMS-754807, BEZ235, xentuzumab, or a combination thereof.

12. The method of claim 9, wherein the E-cadherin inhibitor comprises a small interfering RNA (siRNA), a short hairpin RNA (shRNA), or a combination thereof.

13. The method of claim 9, wherein the cancer comprises a breast cancer.

14. The method of claim 9, further comprising obtaining a cancerous tissue sample from the subject and detecting the level of E-cadherin in the sample.

15. The method of claim 14, wherein the cancer comprises an invasive ductal breast carcinoma (IDC).

16. The method of claim 14, wherein the level of E-cadherin is the level of E-cadherin polypeptide expression.

17. The method of claim 10, wherein the control comprises one or more non-cancerous cells of the subject which are of a same cell type as a cell of the sample.

18. A method of increasing the sensitivity of a cancer in a subject to an IGF1 pathway inhibitor comprising
   a) obtaining a sample of the cancer from the subject;
   b) determining a level of E-cadherin in the sample is not reduced compared to a control; and
   c) administering to the subject a therapeutically effective amount of an E-cadherin inhibitor.

19. The method of claim 18, wherein the E-cadherin inhibitor comprises a small interfering RNA (siRNA), a short hairpin RNA (shRNA), or a combination thereof.

20. The method of claim 18, wherein the E-cadherin inhibitor comprises a small interfering RNA (siRNA).

21. The method of claim 9, wherein the E-cadherin inhibitor comprises a small interfering RNA (siRNA).

22. The method of claim 9, wherein the IGF1R pathway inhibitor comprises xentuzumab.

23. The method of claim 1, wherein the IGF1R pathway inhibitor comprises xentuzumab.

24. The method of claim 1, wherein the endocrine therapeutic comprises tamoxifen.

* * * * *